United States Patent
Faridmoayer

(10) Patent No.: US 11,285,200 B2
(45) Date of Patent: Mar. 29, 2022

(54) MODIFIED HOST CELLS AND HYBRID OLIGOSACCHARIDES FOR USE IN BIOCONJUGATE PRODUCTION

(71) Applicant: GLAXOSMITHKLINE BIOLOGICALS, S.A., Rixensart (BE)

(72) Inventor: Amirreza Faridmoayer, Schlieren (CH)

(73) Assignee: GLAXOSMITHKLINE BIOLOGICALS SA

(*) Notice: Subject to any disclaimer, the term of this patent is extended or adjusted under 35 U.S.C. 154(b) by 0 days.

(21) Appl. No.: 16/386,036

(22) Filed: Apr. 16, 2019

(65) Prior Publication Data

US 2019/0282682 A1    Sep. 19, 2019

Related U.S. Application Data

(62) Division of application No. 15/502,748, filed as application No. PCT/EP2015/068203 on Aug. 6, 2015, now Pat. No. 10,307,474.

(60) Provisional application No. 62/035,360, filed on Aug. 8, 2014.

(51) Int. Cl.
| | |
|---|---|
| *A61K 39/09* | (2006.01) |
| *A61K 47/64* | (2017.01) |
| *C07K 14/195* | (2006.01) |
| *C12N 9/10* | (2006.01) |
| *C12P 19/28* | (2006.01) |
| *C12P 21/00* | (2006.01) |
| *C12N 9/12* | (2006.01) |
| *C08B 37/00* | (2006.01) |
| *C07K 14/705* | (2006.01) |
| *A61K 39/00* | (2006.01) |

(52) U.S. Cl.
CPC .......... *A61K 39/092* (2013.01); *A61K 47/646* (2017.08); *A61K 47/6415* (2017.08); *C07K 14/195* (2013.01); *C07K 14/70575* (2013.01); *C08B 37/006* (2013.01); *C12N 9/10* (2013.01); *C12N 9/1048* (2013.01); *C12N 9/1051* (2013.01); *C12N 9/1081* (2013.01); *C12N 9/1241* (2013.01); *C12N 9/1288* (2013.01); *C12P 19/28* (2013.01); *C12P 21/005* (2013.01); *C12Y 204/01* (2013.01); *C12Y 204/99* (2013.01); *C12Y 204/99018* (2015.07); *C12Y 207/08033* (2013.01); *A61K 2039/6031* (2013.01); *A61K 2039/64* (2013.01); *C12N 2501/815* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,057,540 A | 10/1991 | Kensil et al. | |
| 7,449,308 B2 | 11/2008 | Gerngross et al. | |
| 10,307,474 B2 | 6/2019 | Faridmoayer | |
| 2015/0273043 A1* | 10/2015 | Wacker | C12N 15/70 530/395 |

FOREIGN PATENT DOCUMENTS

| | | |
|---|---|---|
| GB | 2220211 A | 1/1990 |
| WO | 91/18911 A2 | 12/1991 |
| WO | 91/18911 A2 | 12/1991 |
| WO | 2003/074687 A1 | 9/2003 |
| WO | 2003/094961 A1 | 11/2003 |
| WO | 2004/002495 A1 | 1/2004 |
| WO | 2004/002495 A1 | 1/2004 |
| WO | 2005/003775 A2 | 1/2005 |
| WO | 2005/003775 A2 | 1/2005 |
| WO | 2006/119987 A2 | 11/2006 |
| WO | 2007/109812 A2 | 9/2007 |
| WO | 2007/109813 A1 | 9/2007 |
| WO | 2007/125089 A2 | 11/2007 |
| WO | 2007/125089 A2 | 11/2007 |
| WO | 2011/023764 A1 | 3/2011 |
| WO | 2011/027116 A1 | 3/2011 |
| WO | 2011/041003 A2 | 4/2011 |
| WO | 2011/138361 A1 | 11/2011 |
| WO | 2014/013375 A1 | 1/2014 |
| WO | 2014/037585 A1 | 3/2014 |
| WO | 2014/072405 A1 | 5/2014 |
| WO | 2014/095771 A1 | 6/2014 |

OTHER PUBLICATIONS

Garcia-Quintanilla et al. Frontiers in Microbiology Jul. 29, 2014, 5:381, pp. 1-10.*
V. S. Terra et al: "Recent developments in bacterial protein glycan coupling technology and glycoconjugate vaccine design", Journal of Medical Microbiology, vol. 61, Pt 7. Apr. 19, 2012 (Apr. 19, 2012), pp. 919-926.
European Patent Office as International Searching Authority, nternational Search Report and Written Opinion for application No. PCT/EP2015/068203 dated Feb. 19, 2016, 22 pages.
European Patent Office as International Preliminary Report on Patentability for application No. PCT/EP2015/068203 dated Nov. 2, 2016, 34 pages.
Wacker et al., "Substrate specificity of bacterial oligosaccharyltransferase suggests a common transfer mechanism for the bacterial and eukaryotic systems", Proceedings of the National Academy of Sciences of the United States of America, May 2006, vol. 103, No. 18, pp. 7088-7093.

(Continued)

*Primary Examiner* — Oluwatosin A Ogunbiyi
(74) *Attorney, Agent, or Firm* — Dana L. Broughton

(57) ABSTRACT

Provided herein are host cells capable of producing hybrid oligosaccharides and polysaccharides, wherein said hybrid oligosaccharides and polysaccharides do not comprise a hexose at the reducing end of their first repeat unit. Also provided herein are hybrid oligosaccharides or polysaccharides and bioconjugates which can be produced by the host cells described herein, wherein said bioconjugates comprise a carrier protein linked to a hybrid oligosaccharide or polysaccharide that does not comprise a hexose at the reducing end of its first repeat unit.

17 Claims, 35 Drawing Sheets

(56) References Cited

OTHER PUBLICATIONS

Xu et al., "Biochemical Characterization of UDP-Gal:GlcNAc-Pyrophosphate-Lipid β-1,4-Galactosyltransferase WfeD, a New Enzyme from Shigella boydii Type 14 That Catalyzes the Second Step in O-Antigen Repeating-Unit Synthesis" Journal of Bacteriology., 2011, vol. 193, No. 2, pp. 449-459.

Whitfield et al.,"Structure, assembly and regulation of expression of capsules in Escherichia coli" Molecular Microbiology, 1999, vol. 31, No. 5, pp. 1307-1319.

Whitfield et al., "Biosynthesis and Assembly of Capsular Polysaccharides in Escherichia coli", Annual Review of Biochemistry, 2006, vol. 75, pp. 39-68.

Brown et al, "Wall Teichoic Acids of Gram-Positive Bacteria", Annual Review of Microbiology, 2013, vol. 67, pp. 313-336.

Ren et al., "Characterization of Escherichia coli O3 and O21 O antigen gene clusters and development of serogroup-specific PCR assays", Journal of Microbiological Methods, 2008, vol. 75, No. 2, pp. 329-334.

Rush et al., "A Novel Epimerase That Converts GlcNAc-P-P-undecaprenol to GalNAc-P-P-undecaprenol in Escherichia coli O157", Journal of Biological Chemistry 2010, vol. 285 No. 3, pp. 1671-1680.

Bentley et al., "Genetic Analysis of the Capsular Biosynthetic Locus from all 90 Pneumococcal Serotypes", PLoS Genetics 2006, vol. 2 Issue 3 e31, pp. 0262-0269.

Stevenson et al., "Organization of the Escherichia coli K-12 Gene Cluster Responsible for Production of the Extracellular Polysaccharide Colanic Acid", J. of Bacteriology 1996, vol. 178 No. 16, pp. 4885-4893.

Feldman et al., "Engineering N-linked protein glycosylation with diverse O antigen lipopolysaccharide structures in Escherichia coli", PNAS 2005, vol. 102 No. 8, pp. 3016-3021.

Ihssen et al., "Production of glycoprotein vaccines in Escherichia coli", Microbiol. Cell Factories 2010, 9(61): 1-13.

Wacker et al., "N-Linked Glycosylation in Campylobacter jejuni and its Functional Transfer into E.coli", Science 2002, vol. 298, pp. 1790-1793.

UniProtKB Accession No. O86154 entitled "WlaF protein", submitted Sep. 14, 2005, available at https://www.ncbi.nim.nih.gov/protein/O86154.

NCBI Gene ID No. 7410986 entitled "CLA_RS06255 undecaprenyl-diphosphooligosaccharide-protein glycotransferase [Campylobacter lari RM2100]", created Feb. 5, 2009, available at https://www.ncbi.nlm.nih.gov/gene/?term=7410986.

NCBI Gene ID No. 3231775 entitled "pgIB general glycosylation pathway protein [Campylobacter jejuni RM1221]", created Jan. 13, 2005, available at https://www.ncbi.nlm.nih.gov/gene/3231775.

Kensil et al., "Structural and Immunological Characterization of the Vaccine Adjuvant QS-21" Chapter 22 in Vaccine Design: The Subunit and Adjuvant Approach at pp. 525-541 (eds. Powell and Newman, Plenum Press NY 1995), 17 total pages.

Stoute et al., "A Preliminary Evaluation of a Recombinant Circumsporozoite Protein Vaccine Against Plasmodium Falciparum Malaria," J. of New England Med. 1997, vol. 336 No. 2, pp. 86-91.

Lee et al., "Gene doctoring: a method for recombineering in laboratory and pathogenic Escherichia coli strains," BMC Microbiology 2009, vol. 9 No. 252, 14 pages.

Hug and Feldman, "Analogies and homologies in lipopolysaccharide and glycoprotein biosynthesis in bacteria," Glycobiology 2011, vol. 21 No. 2, pp. 138-151.

Linnerborg et al., "Structural studies of the O-antigenic polysaccharide from Escherichia coli O167," Eru. J. Biochem. 1997, vol. 246, pp. 565-573.

Castronuovo et al., "Thermodynamics of the interaction of α-cyclodextrin with monocarboxylic acids in aqueous solutions: a calorimetric study at 25° C.," Carbohydrate Research 1996, vol. 287, pp. 127-138.

Passwell, Justen H, et al., "Safety and immunogenicity of improved Shigella O-specific polysaccharide-protein conjugate vaccines in adults in Israel." Infection and Immunity; 2001; vol. 69 (3); pp. 1351-1357.

Pavliakova, Danka, et al., "Treatment with succinic anhydride improves the immunogenicity of Shigella flexneri type 2a O-specific polysaccharide-protein conjugates in mice." Infection and Immunity; 1999; vol. 67(10); pp. 5526-5529.

Polotsky, Vsevolod Y et al. "Comparison of conjugates composed of lipopolysaccharide from Shigella flexneri type 2a detoxified by two methods and bound to tetanus toxoid." Infection and Immunity; 1994; vol. 62(1); pp. 210-214.

Taylor, D. N. et al., "Synthesis, characterization and clinical evaluation of conjugate vaccines composed of the O-specific polysaccharides of shigella dysenteriae Type 1, Shigella flexneri type 2a and Shigella sonnei (Plesiomonas shigelloides) bound to bacterial toxoids." Infection and Immunity; American Society of Microbiology, Washington DC, US; 1993; vol. 61(9); pp. 3678-3687.

Qianqian et al. The research progress of expression of N type glycoprotein in C. jejuni, Proceedings of the 2010 Biochemical and Biotechnology Drug Thrombosis Symposium, Aug. 1, 2010.

* cited by examiner

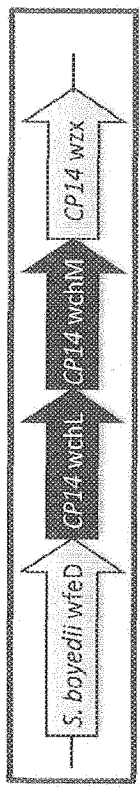
FIG. 4A
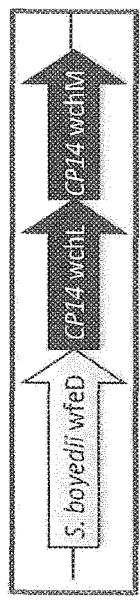
FIG. 4C
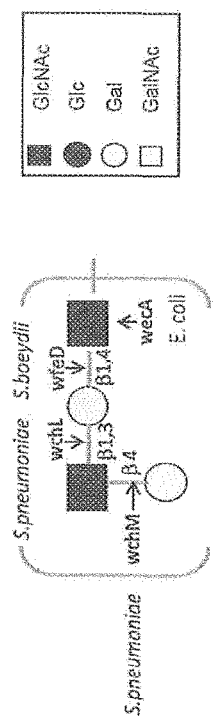
FIG. 4B
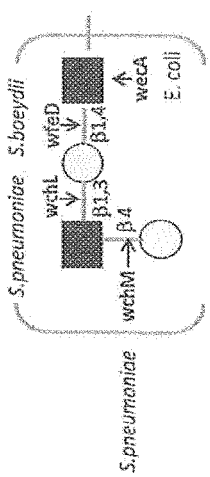
FIG. 4D
FIG. 4.

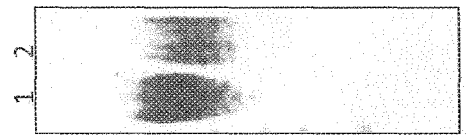
FIG. 13
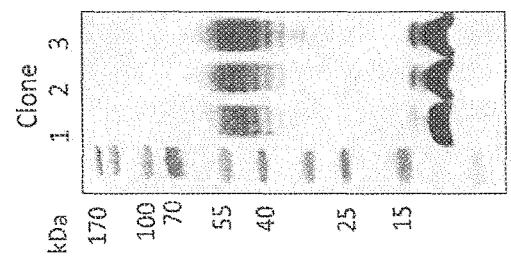

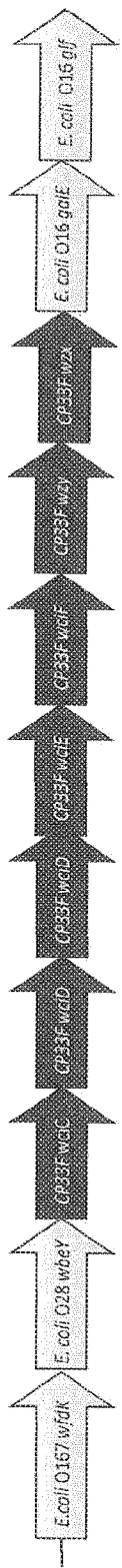
FIG. 14A
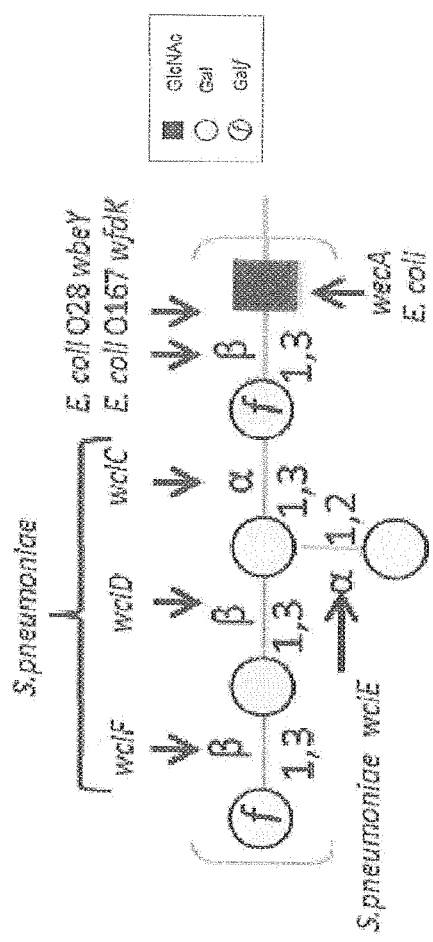
FIG. 14B
FIG. 14

FIG. 15A Silver stained

FIG. 15B α-CP33F

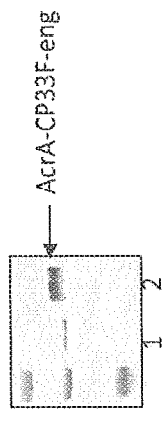
FIG. 17A
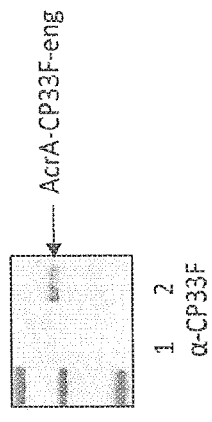
FIG. 17B
FIG. 17

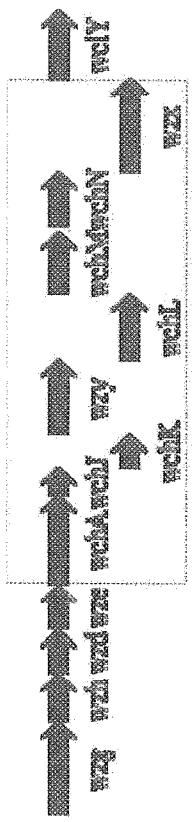
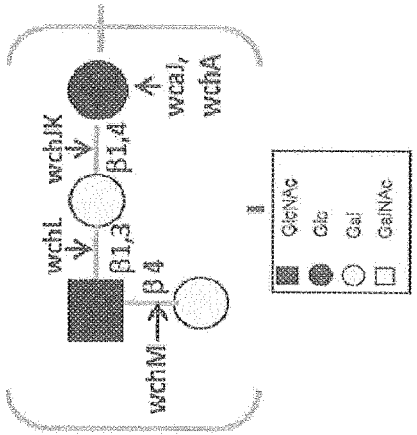
wzg:    Regulatory
wzh:    Regulatory
wzd:    Regulatory
wze:    Regulatory
wchA:   Glc-1-P transferase
wchJ:   Galactosyltransferase transferase
wchK:   Galactosyltransferase transferase
wzy:    Polymerase
wchL:   GlcNAc transferase
wchM:   Galactosyltransferase transferase
wchN:   No assigned function
wzx:    flippase
wclY:   transcription terminator
FIG. 19A
FIG. 19B
FIG. 19

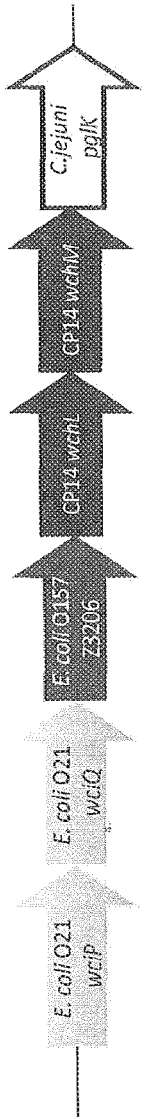
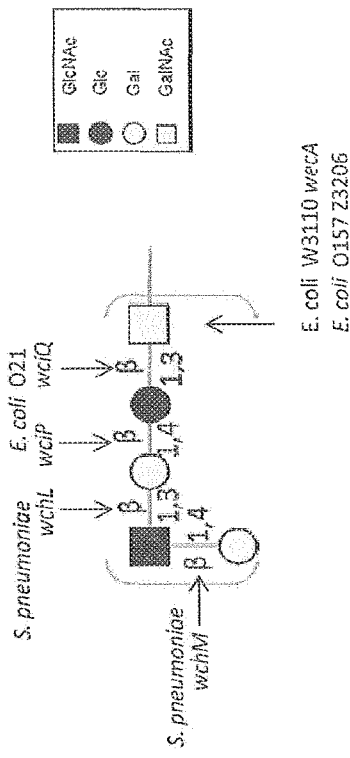
FIG. 20A
FIG. 20B
FIG. 20

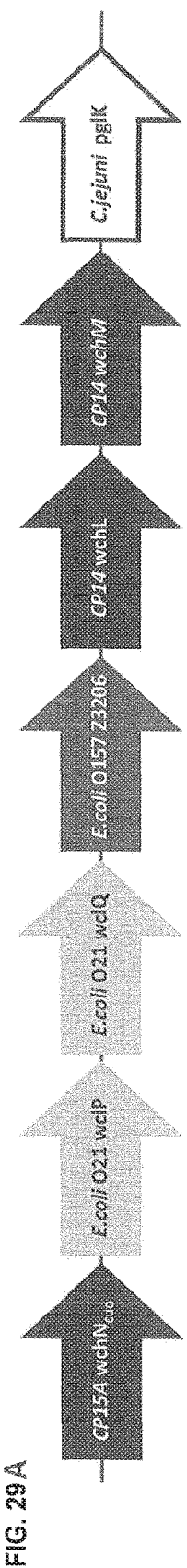
FIG. 29A
CP15A engineering plasmid pGVXN3058:
Genetic organization and sugar structure
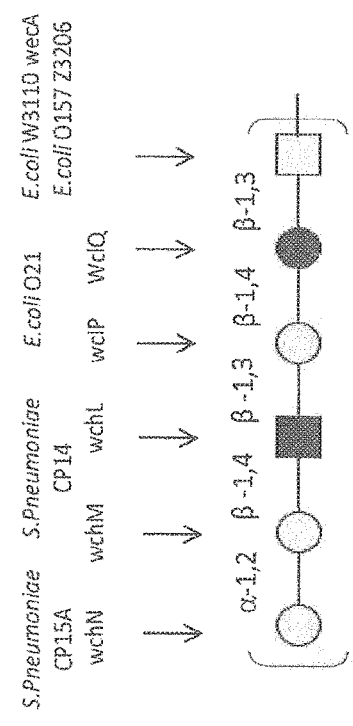
FIG. 29B
FIG. 29

MODIFIED HOST CELLS AND HYBRID OLIGOSACCHARIDES FOR USE IN BIOCONJUGATE PRODUCTION

INTRODUCTION

Provided herein are host cells capable of producing hybrid oligosaccharides and polysaccharides, wherein said hybrid oligosaccharides and polysaccharides do not comprise a hexose at the reducing end of their first repeat unit. Also provided herein are hybrid oligosaccharides and polysaccharides and bioconjugates which can be produced by the host cells described herein, wherein said bioconjugates comprise a carrier protein linked to a hybrid oligosaccharide or polysaccharide that does not comprise a hexose at the reducing end of its first repeat unit.

BACKGROUND

Glycosylation is a process by which carbohydrate molecules or sugars (monosaccharides, disaccharides, oligosaccharides, or polysaccharides) are attached to the side chains of different amino acid residues in a protein or polypeptide to generate a glycoprotein.

N-linked protein glycosylation (N-glycosylation)—the most common type of post-translational modification occurring in the endoplasmic reticulum of eukaryotic organisms—is the addition of carbohydrate molecules to an asparagine residue in the polypeptide chain of a target protein. The process is accomplished by the enzymatic oligosaccharyltransferase complex (OST) responsible for the transfer of a preassembled oligosaccharide from a lipid carrier (dolichol phosphate) to an asparagine residue of a nascent protein within the conserved sequence Asn-X-Ser/Thr (where X is any amino acid except proline) in the endoplasmic reticulum. The saccharide chain is then subjected to other modifications in the Golgi apparatus. In nature, N-linked glycosylation occurs in eukaryotes and archaea, but rarely in bacteria.

O-linked glycosylation is a form of glycosylation that occurs in eukaryotes, archaea, and bacteria. It consists of the attachment of a sugar molecule to an oxygen atom in an amino acid residue in the protein target.

Use of host cells to produce bioconjugates comprising carrier proteins linked (e.g., N-linked) to carbohydrate molecules or sugars is known in the art. However, despite advances in production of bioconjugates using prokaryotic host cells, there remains a need for improved methods of bioconjugate production in host cells.

SUMMARY OF THE INVENTION

It is known in the art that oligosaccharyltransferases from *C. jejuni* (PglB) have a low affinity toward glycans (oligosaccharides or polysaccharides) that comprise a hexose monosaccharide at the reducing end of the first repeat unit (Proc Natl Acad Sci USA. 2006 May 2; 103(18):7088-93). Accordingly, use of host cell systems to produce bioconjugates has typically been limited to production of bioconjugates composed of carrier protein linked to oligosaccharides or polysaccharides that do not comprise a hexose monosaccharide at the reducing end of the first repeat unit. However, because many bacterial oligosaccharide/polysaccharide antigens contain hexose monosaccharides (e.g., glucose) at the reducing end of the first repeat unit, host cell bioconjugate production systems known in the art are insufficient for production of bioconjugates comprising such oligosaccharide/polysaccharide antigens.

The inventor of this application has identified novel approaches for modifying host cell that render the host cells capable of producing hybrid oligosaccharides or polysaccharides that are derived from donor oligosaccharides or polysaccharides. The donor oligosaccharides or polysaccharides are those oligosaccharides or polysaccharides that comprise a hexose monosaccharides (e.g., glucose) at the reducing end of the first repeat unit, whereas the hybrid oligosaccharides or polysaccharides do not comprise a hexose at the reducing end of the first repeat unit, but instead comprise a hexose monosaccharide derivative. Such hexose monosaccharide derivatives are proper substrates for PglB, and thus in the appropriate host cell background can be linked to a carrier protein so as to generate a bioconjugate useful in, e.g., treatment of bacterial disease/infection and/or vaccination against bacterial disease/infection. Importantly, the inventor of this application has surprisingly discovered that translocation and polymerization of the hybrid oligosaccharides and polysaccharides described herein can be accomplished in host cells comprising heterlogous glycosylation machinery (e.g., flippases, polymerases), due to relaxed specificity of polymerase (wzy) and flippase (wzx) enzymes. Together, the discoveries described herein allow for the generation of modified host cells capable of producing high yields of bioconjugates that could not be produced at high yields before the inventor's discoveries.

The invention is summarized by the embodiments presented below.

Embodiment 1: A prokaryotic host cell comprising:
a) nucleic acids that encode glycosyltransferases that produce an oligosaccharide or polysaccharide repeat unit, wherein said repeat unit does not comprise a hexose at the reducing end, and wherein said oligosaccharide or polysaccharide repeat unit is derived from a donor oligosaccharide or polysaccharide repeat unit that comprises a hexose at the reducing end;
b) a nucleic acid that encodes a carrier protein comprising an N-glycosylation consensus sequence; and
c) a nucleic acid that encodes an oligosaccharyl transferase.

Embodiment 2: A prokaryotic host cell comprising:
a) nucleic acids that encode glycosyltransferases that produce an oligosaccharide or polysaccharide repeat unit, wherein said repeat unit does not comprise a hexose at the reducing end, and wherein said oligosaccharide or polysaccharide repeat unit is derived from a donor oligosaccharide or polysaccharide repeat unit that comprises a hexose at the reducing end;
b) a nucleic acid that encodes a carrier protein comprising an N-glycosylation consensus sequence;
c) a nucleic acid that encodes an oligosaccharyl transferase; and
d) a nucleic acid that encodes a polymerase (wzy), wherein the polymerase catalyzes the production of a hybrid oligosaccharide or polysaccharide, wherein the hybrid oligosaccharide or polysaccharide (i) comprises a hexose monosaccharide derivative at the reducing end of the first repeat unit and (ii) comprises hexose monosaccharides at the reducing end of all other repeat units.

Embodiment 3: The host cell of embodiment 1 or 2, wherein said host cell comprises glycosyltransferases sufficient for synthesis of the donor oligosaccharide or polysaccharide repeat unit.

Embodiment 4: The host cell of embodiment 3, wherein said glycosyltransferases sufficient for synthesis of the repeat units of the donor oligosaccharide or polysaccharide are present in the host cell as an operon or gene cluster, or portion thereof.

Embodiment 5: The host cell of any one of embodiments 1-4, wherein said host cell is capable of producing a hybrid oligosaccharide or polysaccharide, wherein said hybrid oligosaccharide or polysaccharide is identical to the donor oligosaccharide or polysaccharide, with the exception that said hybrid oligosaccharide or polysaccharide comprises a hexose monosaccharide derivative at the reducing end of the first repeat unit in place of the hexose monosaccharide normally present at the reducing end of the first repeat unit of the donor oligosaccharide or polysaccharide.

Embodiment 6: The host cell of any one of embodiments 1-4, wherein said host cell is capable of producing a hybrid oligosaccharide or polysaccharide, wherein said hybrid oligosaccharide or polysaccharide is identical to the donor oligosaccharide or polysaccharide, with the exception of the fact that said hybrid oligosaccharide or polysaccharide comprises a hexose monosaccharide derivative at the reducing end of the first repeat unit in addition to comprising all of the monosaccharides of the donor oligosaccharide or polysaccharide.

Embodiment 7: The host cell of any one of embodiments 1-4, wherein said host cell comprises (i) a glycosyltransferase that assembles a hexose monosaccharide derivative onto undecaprenyl pyrophosphate (UND-PP) and (ii) one or more glycosyltransferases capable of adding a monosaccharide to the hexose monosaccharide derivative assembled on UND-PP.

Embodiment 8: The host cell of embodiment 7, wherein said hexose monosaccharide derivative is any monosaccharide which C-2 position is modified with acetamido group such as N-acetylglucosamine (GlcNAc), N-acetylgalactoseamine (GalNAc), 2,4-Diacetamido-2,4,6-trideoxyhexose (DATDH). N-acetylfucoseamine (FucNAc), N-acetylquinovosamine (QuiNAc); or the host cell of embodiment 7, wherein said hexose monosaccharide derivative is N-acetylglucosamine (GlcNAc).

Embodiment 9: The host cell of embodiment 7 or 8, wherein said glycosyltransferase that assembles a hexose monosaccharide derivative onto UND-PP is heterologous to the host cell and/or heterologous to the genes that catalyze the donor oligosaccharide repeat unit.

Embodiment 10: The host cell of any one of embodiments 7-9, wherein said glycosyltransferase that assembles a hexose monosaccharide derivative onto UND-PP is from *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species.

Embodiment 11: The host cell of any one of embodiments 7-10, wherein said glycosyltransferase that assembles a hexose monosaccharide derivative onto UND-PP is wecA.

Embodiment 12: The host cell of embodiment 11, wherein said wecA is from *E. coli*.

Embodiment 13: The host cell of any one of embodiments 7-12, wherein said hexose monosaccharide is galactose (Gal).

Embodiment 14: The host cell of any one of embodiments 7-13, wherein said one or more glycosyltransferases capable of adding a monosaccharide to the hexose monosaccharide derivative is the galactosyltransferase (wfeD) from *Shigella boyedii*.

Embodiment 15: The host cell of any one of embodiments 7-13, wherein said one or more glycosyltransferases capable of adding a monosaccharide to the hexose monosaccharide derivative is the galactofuranosyltransferase (WbeY) from *E. coli* O28.

Embodiment 16: The host cell of any one of embodiments 7-13, wherein said one or more glycosyltransferases capable of adding a monosaccharide to the hexose monosaccharide derivative is the galactofuranosyltransferase (WfdK) from *E. coli* O167.

Embodiment 17: The host cell of any one of embodiments 7-13, wherein said one or more glycosyltransferases capable of adding a monosaccharide to the hexose monosaccharide derivative are the galactofuranosyltransferase (WbeY) from *E. coli* O28 and the galactofuranosyltransferase (WfdK) from *E. coli* O167.

Embodiment 18: The host cell of any one of embodiments 3, 4, or 6-17, wherein said glycosyltransferases sufficient for synthesis of the repeat units of the donor oligosaccharide or polysaccharide comprise WchL (N-acetylglucosaminetransferase) and WchM (galactosyltransferase) from *S. pneumoniae* CP14

Embodiment 19: The host cell of embodiment 18, wherein said host cell is capable of producing a hybrid oligosaccharide or polysaccharide, wherein said hybrid oligosaccharide or polysaccharide is identical to *S. pneumoniae* CP14, with the exception of the fact that said hybrid oligosaccharide or polysaccharide comprises a hexose monosaccharide derivative at the reducing end of the first repeat unit in place of the hexose monosaccharide normally present at the reducing end of the first repeat unit of *S. pneumoniae* CP14.

Embodiment 20: The host cell of any one of embodiments 3, 4, or 6-17, wherein said glycosyltransferases sufficient for synthesis of the repeat units of the donor oligosaccharide or polysaccharide comprise WciB, WciC, WciD, WciE, and WciF from *S. pneumoniae* CP33F.

Embodiment 21: The host cell of embodiment 20, wherein said host cell is capable of producing a hybrid oligosaccharide or polysaccharide, wherein said hybrid oligosaccharide or polysaccharide is identical to *S. pneumoniae* CP33F, with the exception of the fact that said hybrid oligosaccharide or polysaccharide comprises a hexose monosaccharide derivative at the reducing end of the first repeat unit in place of the hexose monosaccharide normally present at the reducing end of the first repeat unit of *S. pneumoniae* CP33F.

Embodiment 22: The host cell of any one of embodiments 1-4, wherein said host cell comprises (i) a glycosyltransferase that assembles a hexose monosaccharide derivative onto undecaprenyl pyrophosphate (UND-PP) and (ii) glycosyltransferases that assemble the donor oligosaccharide or polysaccharide repeat unit onto the hexose monosaccharide derivative.

Embodiment 23: The host cell of embodiment 22, wherein said hexose monosaccharide derivative is N-Acetylglucosamine (GlcNAc); alternatively said hexose monosaccharide derivative is any monosaccharide which C-2 position is modified with acetamido group such as N-acetylglucosamine (GlcNAc), N-acetylgalactoseamine (GalNAc), 2,4-Diacetamido-2,4,6-trideoxyhexose (DATDH). N-acetylfucoseamine (FucNAc), N-acetylquinovosamine (QuiNAc).

Embodiment 24: The host cell of embodiment 22 or 23, wherein said glycosyltransferase that assembles a hexose monosaccharide derivative onto UND-PP is heterologous to the host cell.

Embodiment 25: The host cell of any one of embodiments 22-24, wherein said glycosyltransferase that assembles a hexose monosaccharide derivative onto UND-PP is from *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species.

Embodiment 26: The host cell of any one of embodiments 22-25, wherein said glycosyltransferase that assembles a hexose monosaccharide derivative onto UND-PP is wecA.

Embodiment 27: The host cell of embodiment 26, wherein said wecA is from *E. coli*.

Embodiment 28: The host cell of any one of embodiments 22-27, wherein the glycosyltransferases that assemble the donor oligosaccharide or polysaccharide repeat unit onto the hexose monosaccharide derivative comprise a glycosyltransferase that is capable of adding the hexose monosaccharide present at the reducing end of the first repeat unit of the donor oligosaccharide or polysaccharide to the hexose monosaccharide derivative linked to Undecaprenyl phosphate.

Embodiment 29: The host cell of embodiment 28, wherein said glycosyltransferase that is capable of adding said hexose monosaccharide present at the reducing end of the first repeat unit of the donor oligosaccharide or polysaccharide to the monosaccharide linked to Undecprenyl phosphate is a glucosyltransferase such as WciQ, WfaM, WfaP, WeiL, WelO, WffJ, WfgD, WbdN, WcmM.

Embodiment 30: The host cell of embodiment 29, wherein said glucosyltransferase are WciQ from *E. coli* O21, WfaM from *E. coli* O24, WfaP from *E. coli* O56, WeiL from *E. coli* O61, WelO from *E. coli* O102, WffJ from *E. coli* O130, WfgD from *E. coli* O152, WbdN from *E. coli* O157, and WcmM from *E. coli* O173.

Embodiment 31: The host cell of any one of embodiments 28-30, wherein the glycosyltransferases that assemble the donor oligosaccharide or polysaccharide repeat unit onto the hexose monosaccharide derivative comprise a glycosyltransferase that is capable of adding the monosaccharide that is adjacent to the hexose monosaccharide present at the reducing end of the first repeat unit of the donor oligosaccharide or polysaccharide to the hexose monosaccharide present at the reducing end of the first repeat unit of the donor oligosaccharide or polysaccharide.

Embodiment 32: The host cell of embodiment 31, wherein said glycosyltransferase that is capable of adding the monosaccharide that is adjacent to the hexose monosaccharide present at the reducing end of the first repeat unit of the donor oligosaccharide or polysaccharide to the hexose monosaccharide present at the reducing end of the first repeat unit of the donor oligosaccharide or polysaccharide is a glucosyltransferase (such as WciP or wciQ).

Embodiment 33: The host cell of embodiment 32, glucosyltransferase is wciQ from *E. coli* O21 or the galactosyltransferase WciQ from *E. coli* O21.

Embodiment 34: The host cell of any one of embodiments 32-33, wherein said host cell further comprises an enzyme capable modifying a monosaccharide.

Embodiment 35: The host cell of embodiment 34, wherein enzyme is an epimerase or a racemase.

Embodiment 36: The host cell of embodiment 35, wherein said epimerase is from *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species.

Embodiment 37: The host cell of embodiment 36, wherein said epimerase is from *E. coli*.

Embodiment 38: The host cell of embodiment 37, wherein said epimerase is Z3206 from *E. coli* O157.

Embodiment 39: The host cell of any one of embodiments 22-38, wherein said glycosyltransferases sufficient for synthesis of the repeat units of the donor oligosaccharide or polysaccharide comprise wchL and wchM from *S. pneumoniae* CP14.

Embodiment 40: The host cell of embodiment 39, wherein said host cell is capable of producing a hybrid oligosaccharide or polysaccharide, wherein said hybrid oligosaccharide or polysaccharide is identical to *S. pneumoniae* CP14, with the exception of the fact that said hybrid oligosaccharide or polysaccharide comprises a hexose monosaccharide derivative at the reducing end of the first repeat unit in addition to comprising all of the monosaccharide residues of *S. pneumoniae* CP14.

Embodiment 41: The host cell of any one of embodiments 1-40, wherein said non-hexose monosaccharide or said hexose monosaccharide derivative is a monosaccharide comprising an acetamido group at position 2.

Embodiment 42: The host cell of embodiment 41, wherein said non-hexose monosaccharide or said hexose monosaccharide derivative is GlcNAc, HexNAc, deoxy HexNAc, FucNAc, GalNAc, QuiNAc, ManNAc, or 2,4-diacetamido-2,4,6-trideoxyhexose.

Embodiment 43: The host cell of any one of embodiments 1-42, wherein said host cell comprises a nucleic acid that encodes a capsular polysaccharide polymerase (wzy) or an O antigen polymerase (wzy).

Embodiment 44: The host cell of embodiment 43, wherein said polymerase is heterologous to the host cell and/or said polymerase is heterologous to the gene cluster encoding the enzymes for synthesis of the donor oligosaccharide or polysaccharide repeat unit.

Embodiment 45: The host cell of embodiment 43-44, wherein said polymerase is from *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species.

Embodiment 46: The host cell of embodiment 45, wherein said polymerase is from *Streptococcus pneumoniae*.

Embodiment 47: The host cell of embodiment 46, wherein said polymerase is from *S. pneumoniae* CP1, CP2, CP3, CP4, CP5, CP6 (A and B), CP7 (A,B, C), CP8, CP9 (A, L,N, V), CP10 (A,B,C,F), CP11 (A, B,C,D,F), CP12(A,B,F), CP13, CP14 CP15(A,B,C,F), CP16(A,F), CP17(A,F), CP18 (A,B,C,F), CP19(A,B,C,F), CP20,CP21, CP22(A,F), CP23 (A,B,F), CP24(A,B,F), CP25(A,F), CP26, CP27,CP28(A, F), CP29, CP31, CP32(A,F), CP33(A,B,C,D,F), CP34, CP35(A,B,C,D,F), CP36, CP37, CP38, CP39, CP40, CP41 (A,F), CP42, CP43, CP44, CP45, CP46, CP47(A,F), or CP48.

Embodiment 48: The host cell of any one of embodiments 1-47, wherein said host cell comprises a nucleic acid that encodes a flippase (wzx).

Embodiment 49: host cell of embodiment 48, wherein said flippase is heterologous to the host cell and/or said flippase is heterologous to the gene cluster encoding the enzymes for synthesis of the donor oligosaccharide or polysaccharide repeat unit.

Embodiment 50: The host cell of embodiment 48-49, wherein said flippase is from *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species.

Embodiment 51: The host cell of embodiment 50, wherein said flippase is from *Streptococcus pneumoniae*.

Embodiment 52: The host cell of embodiment 51, wherein said flippase is from *S. pneumoniae* CP1, CP2, CP3, CP4, CP5, CP6 (A and B), CP7 (A,B, C), CP8, CP9 (A, L,N, V), CP10 (A,B,C,F), CP11 (A, B,C,D,F), CP12(A,B,F), CP13, CP14 CP15(A,B,C,F), CP16(A,F), CP17(A,F), CP18(A,B,C,F), CP19(A,B,C,F), CP20,CP21, CP22(A,F), CP23(A,B,F), CP24(A,B,F), CP25(A,F), CP26, CP27,CP28(A,F), CP29, CP31, CP32(A,F), CP33(A,B,C,D,F), CP34, CP35 (A,B,C,D,F), CP36, CP37, CP38, CP39, CP40, CP41(A,F), CP42, CP43, CP44, CP45, CP46, CP47(A,F), or CP48.

Embodiment 53: The host cell of any one of embodiments 1-52, wherein said oligosaccharide or polysaccharide is from *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species.

Embodiment 54: The host cell of any one of embodiments 1-53, wherein said polysaccharide is a capsular polysaccharide (CP).

Embodiment 55: The host cell of embodiment 54, wherein said capsular polysaccharide is from *Streptococcus pneumoniae*.

Embodiment 56: The host cell of embodiment 45, wherein said *S. pneumoniae* capsular polysaccharide is CP1, CP2, CP3, CP4, CP5, CP6 (A, B), CP7 (A, B, C), CP8, CP9 (A, L, N, V), CP10 (A, B, C, F), CP11 (A, B, C, D, F), CP12(A, B, F), CP13, CP14, CP15 (A, B, C, F), CP16 (A, F), CP17 (A, F), CP18 (A, B, C, F), CP19 (A, B, C, F), CP20, CP21, CP22 (A, F), CP23 (A, B, F), CP24 (A, B, F), CP25 (A, F), CP 26, CP27, CP28 (A, F), CP29, CP31, CP32 (A, F), CP33 (A, B, C, D, F), CP34, CP35 (A, B, C, D, F), CP36, CP37, CP38, CP39, CP40, CP41 (A, F), CP42, CP43, CP44, CP45, CP46, CP47 (A, F), or CP48.

Embodiment 57: The host cell of embodiment 56, wherein said *S. pneumoniae* capsular polysaccharide is CP8, CP15A, CP16F, CP22F, CP23A, CP24F, CP31, CP33F, CP35B, or CP38.

Embodiment 58: The host cell of embodiment 56, wherein said *S. pneumoniae* capsular polysaccharide is CP14.

Embodiment 59: The host cell of embodiment 56, wherein said *S. pneumoniae* capsular polysaccharide is CP33F.

Embodiment 60: The host cell of embodiment 54, wherein said capsular polysaccharide is from *Staphylococcus aureus*.

Embodiment 61: The host cell of embodiment 60, wherein said *S. aureus* capsular polysaccharide is CP5 or CP8.

Embodiment 62: The host cell of embodiment 54, wherein said capsular polysaccharide is from *Streptococcus agalactiae* (GBS).

Embodiment 63: The host cell of embodiment 62, wherein said *Streptococcus agalactiae* capsular polysaccharide is *S. agalactiae* (group B, GBS) CPIa, CPIb, CPII, CPIII, CPIV, CPV, CPVI, CPVII, or CPVIII.

Embodiment 64: The host cell of embodiment 54, wherein said capsular polysaccharide is from *Enterococcus faecalis*.

Embodiment 65: The host cell of embodiment 64, wherein said *Enterococcus faecalis* capsular polysaccharide is CPA, CPB, CPC, or CPD.

Embodiment 66: The host cell of embodiment 1-65, wherein at least one of said glycosyltransferases that produce an oligosaccharide or polysaccharide that does not comprise a hexose at the reducing end of the first repeat unit are heterologous to the host cell.

Embodiment 67: The host cell of embodiment 1-66, wherein said carrier protein is heterologous to the host cell.

Embodiment 68: The host cell of any one of embodiments 1-67, wherein said oligosaccharyl transferase is heterologous to the host cell.

Embodiment 69: The host cell of embodiment 1-65, wherein at least one of said glycosyltransferases that produce an oligosaccharide or polysaccharide that does not comprise a hexose at the reducing end of the first repeat unit, said oligosaccharyl transferase, and said carrier protein are heterologous to the host cell.

Embodiment 70: The host cell of any one of embodiments 1-69, wherein said oligosaccharyl transferase from *Campylobacter jejuni*.

Embodiment 71: The host cell of embodiment 70, wherein said oligosaccharyl transferase is the pglB gene of *C. jejuni*.

Embodiment 72: The host cell of embodiment 71, wherein said pglB gene of *C. jejuni* is integrated into the host cell genome.

Embodiment 73: The host cell of any one of embodiments 1-72, wherein said oligosaccharyl transferase is derived from a eukaryotic organism or an Archaea organism.

Embodiment 74: The host cell of any one of embodiments 3-73, wherein said glycosyltransferases sufficient for synthesis of the repeat units of the donor oligosaccharide or polysaccharide are integrated into the host cell genome.

Embodiment 75: The host cell of any one of embodiments 1-74, wherein said carrier protein is detoxified Exotoxin A of *P. aeruginosa* (EPA), CRM197, maltose binding protein (MBP), Diphtheria toxoid, Tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* polyhistidine triad protein D (PhtD), *Streptococcus pneumoniae* Pneumolysin and detoxified variants thereof (dPly), *C. jejuni* AcrA, a *C. jejuni* natural glycoprotein, PcrV (aka LcrV,EspA, SseB), PopB (YopB, YopD, FliC), or OprF, OprI.

Embodiment 76: The host cell of any one of embodiments 1-75, wherein at least one gene of the host cell has been functionally inactivated or deleted.

Embodiment 77: The host cell of embodiment 76, wherein the waaL gene of the host cell has been functionally inactivated or deleted.

Embodiment 78: The host cell of embodiment 77, wherein the waaL gene of the host cell has been replaced by a nucleic acid encoding an oligosaccharyltransferase.

Embodiment 79: The host cell of embodiment 78, wherein the waaL gene of the host cell has been replaced by C. jejuni pglB.

Embodiment 80: The host cell of any one of embodiments 1-79, wherein said host cell is E. coli.

Embodiment 81: The host cell of any one of embodiments 1-80, wherein as a result of comprising glycosyltransferases that produce an oligosaccharide or polysaccharide that does not comprise a hexose at the reducing end of the first repeat unit, said host cell is capable of producing a higher yield of bioconjugates comprising the carrier protein N-linked to the oligosaccharide or polysaccharide than a host cell of the same phenotype but that comprises the donor oligosaccharide or polysaccharide.

Embodiment 82: The host cell of embodiment 81, wherein said host cell produces at least or about 10%, 20%, 30%, 40%, 50%, 60%, 70%, 80%, 90%, 100%, 200%, 300%, 400%, or 500% more bioconjugates than a host cell of the same phenotype but that comprises the donor oligosaccharide or polysaccharide, wherein said bioconjugates comprise the carrier protein N-linked to the oligosaccharide or polysaccharide.

Embodiment 83: The host cell of embodiment 81, wherein said host cell produces at least or about 5-fold, 10-fold, 20-fold, 30-fold, 40-fold, 50-fold, 60-fold, 70-fold, 80-fold, 90-fold, or 100-fold more bioconjugates than a host cell of the same phenotype but that comprises the donor oligosaccharide or polysaccharide, wherein said bioconjugates comprise the carrier protein N-linked to the oligosaccharide or polysaccharide.

Embodiment 84: A method of producing a bioconjugate comprising a carrier protein N-linked to an oligosaccharide or polysaccharide that does not comprise a hexose at the reducing end of the first repeat unit, said method comprising (i) culturing the host cell of any one of embodiments 1-83 under conditions suitable for the production of proteins and (ii) isolating said bioconjugate.

Embodiment 85: A bioconjugate produced by the method of embodiment 84.

Embodiment 86: The bioconjugate of embodiment 85, comprising a carrier protein linked to a capsular polysaccharide (CP).

Embodiment 87: The bioconjugate of embodiment 86, wherein said capsular polysaccharide is from Streptococcus pneumoniae.

Embodiment 88: The bioconjugate of embodiment 87, wherein said S. pneumoniae capsular polysaccharide is CP1, CP2, CP3, CP4, CP5, CP6 (A, B), CP7 (A, B, C), CP8, CP9 (A, L, N, V), CP10 (A, B, C, F), CP11 (A, B, C, D, F), CP12(A, B, F), CP13, CP14, CP15 (A, B, C, F), CP16 (A, F), CP17 (A, F), CP18 (A, B, C, F), CP19 (A, B, C, F), CP20, CP21, CP22 (A, F), CP23 (A, B, F), CP24 (A, B, F), CP25 (A, F), CP 26, CP27, CP28 (A, F), CP29, CP31, CP32 (A, F), CP33 (A, B, C, D, F), CP34, CP35 (A, B, C, D, F), CP36, CP37, CP38, CP39, CP40, CP41 (A, F), CP42, CP43, CP44, CP45, CP46, CP47 (A, F), or CP48.

Embodiment 89: The bioconjugate of embodiment 88, wherein said S. pneumoniae capsular polysaccharide is CP8, CP15A, CP16F, CP22F, CP23A, CP24F, CP31, CP33F, CP35B, or CP38.

Embodiment 90: The bioconjugate of embodiment 88, wherein said S. pneumoniae capsular polysaccharide is CP14.

Embodiment 91: The bioconjugate of embodiment 88, wherein said S. pneumoniae capsular polysaccharide is CP33F.

Embodiment 92: The bioconjugate of embodiment 86, wherein said capsular polysaccharide is from Staphylococcus aureus.

Embodiment 93: The bioconjugate of embodiment 92, wherein said S. aureus capsular polysaccharide is CP5 or CP8.

Embodiment 94: The bioconjugate of embodiment 86, wherein said capsular polysaccharide is from Streptococcus agalactiae (GBS).

Embodiment 95: The bioconjugate of embodiment 94, wherein said Streptococcus agalactiae capsular polysaccharide is S. agalactiae (group B, GBS) CPIa, CPIb, CPII, CPIII, CPIV, CPV, CPVI, CPVII, or CPVIII.

Embodiment 96: The bioconjugate of embodiment 86, wherein said capsular polysaccharide is from Enterococcus faecalis.

Embodiment 97: The bioconjugate of embodiment 96, wherein said Enterococcus faecalis capsular polysaccharide is CPA, CPB, CPC, or CPD.

Embodiment 98: A composition comprising the bioconjugate of any one of embodiments 85-97.

Embodiment 99: A method of treating or preventing a bacterial infection in a subject, comprising administering to the subject the composition of embodiment 98.

Embodiment 100: A method of inducing an immune response against a bacterial strain in a subject, comprising administering to the subject the composition of embodiment 98.

Embodiment 101: The method of embodiment 99 or 100, wherein the subject is a human.

Embodiment 102: A method of synthesizing an oligosaccharide or a polysaccharide of the structure $$(B)_n - A \rightarrow$$

wherein A is an oligosaccharide repeat unit with a hexose monosaccharide derivative at the reducing end (indicated by arrow);

wherein B is an oligosaccharide repeat unit;

wherein A and B are different oligosaccharide repeat units; and wherein n is at least 1, 2, 3, 4, 5, 6, 7, 8, 9, 10, 11, 12, 13, 14, 15, 16, 17, 18, 19, or at least 20;

said method comprising: incubating A and B with a polysaccharide polymerase.

Embodiment 103: The method of embodiment 102 wherein said contacting step is performed in vitro.

Embodiment 104: The method of embodiment 102 wherein said contacting step is performed in a prokaryotic cell.

Embodiment 105: The method of embodiment 102 wherein said contacting step is performed in the periplasm of a prokaryotic cell.

Embodiment 106: The method of embodiment 102 wherein said polysaccharide polymerase is a wzy polysaccharide polymerase.

Embodiment 107: The method of embodiment 102 wherein A has a hexose monosaccharide derivative at the reducing end (indicated by arrow) and B has a hexose at the reducing end, and wherein A and B are otherwise identical.

Embodiment 108: The method of any one of embodiments 102 to107, wherein said non-hexose monosaccharide or said hexose monosaccharide derivative is GlcNAc, GalNAc. FucNAc, QuiNAc, ManNAc, HexNAc, deoxy HexNAc, or 2,4-diacetamido-2,4,6-trideoxyhexose.

Embodiment 109: The method of embodiment 102 wherein A has the same structure as B with the one difference that A has an additional monosaccharide at the reducing end.

Embodiment 110: The method of embodiment 109 wherein the additional monosaccharide is a hexose monosaccharide derivative.

Embodiment 111: The method of any one of embodiments 109 to 110 wherein the additional monosaccharide is GlcNAc, HexNAc, deoxy HexNAc, or 2,4-diacetamido-2,4,6-trideoxyhexose.

Embodiment 112: The method of any one of embodiments 102 to 111, wherein said polymerase is from *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species.

Embodiment 113: The method of any one of embodiments 102 to 111, wherein said donor oligosaccharide or polysaccharide repeat unit is a repeat unit of *S. pneumoniae* capsular polysaccharide CP1, CP2, CP3, CP4, CP5, CP6 (A, B), CP7 (A, B, C), CP8, CP9 (A, L, N, V), CP10 (A, B, C, F), CP11 (A, B, C, D, F), CP12(A, B, F), CP13, CP14, CP15 (A, B, C, F), CP16 (A, F), CP17 (A, F), CP18 (A, B, C, F), CP19 (A, B, C, F), CP20, CP21, CP22 (A, F), CP23 (A, B, F), CP24 (A, B, F), CP25 (A, F), CP 26, CP27, CP28 (A, F), CP29, CP31, CP32 (A, F), CP33 (A, B, C, D, F), CP34, CP35 (A, B, C, D, F), CP36, CP37, CP38, CP39, CP40, CP41 (A, F), CP42, CP43, CP44, CP45, CP46, CP47 (A, F), or CP48.

Embodiment 114: A pharmaceutical composition comprising an oligosaccharide or a polysaccharide synthesized by the method of any one of embodiments 102 to 111.

Embodiment 115: A bioconjugate comprising a carrier protein N-linked to a hybrid oligosaccharide or polysaccharide, wherein said hydrid oligosaccharide or polysaccharide is identical to a donor oligosaccharide or polysaccharide, with the exception of the fact that the hybrid oligosaccharide or polysaccharide comprises a hexose monosaccharide derivative at the reducing end of the first repeat unit in addition to comprising all of the monosaccharides of the donor oligosaccharide or polysaccharide.

Embodiment 116: The bioconjugate of embodiment 115 wherein the hexose monosaccharide derivative is any monosaccharide in which C-2 position is modified with an acetamido group such as N-acetylglucosamine (GlcNAc), N-acetylgalactoseamine (GalNAc), 2,4-Diacetamido-2,4,6-trideoxyhexose (DATDH). N-acetylfucoseamine (FucNAc), or N-acetylquinovosamine (QuiNAc).

Embodiment 117: The bioconjugate of embodiment 116 in which the hexose monosaccharide derivative is N-acetylglucoamine (GlcNAc).

Embodiment 118: The bioconjugate of embodiment 115 or 116 or 117 wherein the hybrid oligosaccharide or polysaccharide is identical to a Gram positive bacterial capsular saccharide, with the exception of the fact that the hybrid oligosaccharide or polysaccharide comprises a hexose monosaccharide derivative at the reducing end of the first repeat unit in place of the hexose monosaccharide normally present at the reducing end of the first repeat of said Gram positive bacterial capsular saccharide.

Embodiment 119: The bioconjugate of embodiment 118 wherein the Gram positive bacterial capsular saccharide is a Group A streptococcus capsular saccharide, a Group B streptococcus capsular saccharide, a *Streptocuccus pneumoniae* capsular saccharide, Enterococcal capsular saccharide or a *Staphylococcus aureus* capsular saccharide.

Embodiment 120: The bioconjugate of embodiment 119 wherein the Gram positive bacterial capsular saccharide is a *Streptococcus pneumoniae* serotype 1, 2, 3, 4, 5, 6A, 6B, 7A, 7B, 7C, 8, 9A, 9L, 9N, 9V, 10A, 10B, 10C, 10F, 11A, 11B, 11C, 11D, 11F, 12A, 12B, 13, 14, 15A, 15B, 15C, 15F, 16A, 16F, 17A, 17F, 18A, 18B, 18C, 18F, 19A, 19B, 19C, 19F, 20, 21, 22A, 22F, 23A, 23B, 23F, 24A, 24B, 24F, 25A, 25F, 26, 27, 28A, 28F, 29, 31, 32A, 32F, 33A, 33B, 33C, 33D, 33F, 34, 35A, 35B, 35C, 35D, 35F, 36, 37, 38, 39, 40, 41A, 41F, 42, 43, 44, 45, 46, 47A, 47F or 48 capsular saccharide.

Embodiment 121: The bioconjugate of embodiment 120, wherein the Gram positive bacterial capsular saccharide is a *Streptococcus pneumoniae* serotype 8, 14, 15A, 16F, 22F, 23A, 24F, 31, 33F, 35B or 38 capsular saccharide.

Embodiment 122: The bioconjugate of embodiment 118 wherein the Gram positive bacterial capsular saccharide is a *S. aureus* serotype 5 or 8 capsular saccharide.

Embodiment 123: The bioconjugate of embodiment 118 wherein the Gram positive bacterial capsular saccharide is a *Streptococcus agalactiae* (Goup B Streptococcus) serotype Ia, Ib, II, III, IV, V, VI, VII or VIII capsular saccharide.

Embodiment 124: The bioconjugate of embodiment 118 wherein the Gram positive bacterial capsular saccharide is a *Enterococcus faecalis* serotype A, B, C or D capsular saccharide.

Embodiment 125: The bioconjugate of any one of embodiments 115-124 wherein the carrier protein is detoxified Exotoxin A of *P. aeruginosa* (EPA), CRM197, maltose binding protein (MBP), Diphtheria toxoid, Tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin and detoxified variants thereof, *C. jejuni* AcrA, a *C. jejuni* natural glycoprotein, PcrV (aka LcrV,EspA, SseB), PopB (YopB, YopD, FliC), or OprF, OprI.

Embodiment 126: A hybrid oligosaccharide or polysaccharide having a structure $(B)_n\text{-}A\rightarrow$ wherein A is an oligosaccharide repeat unit containing at least 2, 3, 4, 5, 6, 7 or 8 monosaccharides, with a hexose monosaccharide derivative at the reducing end (indicated by arrow);

wherein B is an oligosaccharide repeat unit containing at least 2, 3, 4, 5, 6, 7 or 8 monosaccharides;

wherein A and B are different oligosaccharide repeat units; and wherein n is at least 1, 2, 3, 4, 5, 6, 7, 8, 9, 10, 11, 12, 13, 14, 15, 16, 17, 18, 19, or at least 20.

Embodiment 127: The hybrid oligosaccharide or polysaccharide of embodiment 126 wherein the B oligosaccharide repeat contains a hexose monosaccharide at the reducing end of the repeat.

Embodiment 128: The hybrid oligosaccharide or polysaccharide of embodiment 127 wherein the hexose monosaccharide at the reducing end of the repeat is selected from the group consisting of glucose, galactose, rhamnose, arabinotol, fucose and mannose.

Embodiment 129: The hybrid oligosaccharide or polysaccharide of any one of embodiments 126-128 wherein the oligosaccharide repeat unit of A and the oligosaccharide repeat unit of B differ only by containing a different monosaccharide at the reducing end of the repeat.

Embodiment 130: The hybrid oligosaccharide or polysaccharide of any one of embodiments 126-129 wherein the oligosaccharide repeat unit of A is the repeat unit of the capsular saccharide of a Gram positive bacterial capsular saccharide, for example a Group A streptococcus capsular saccharide, a Group B streptococcus capsular saccharide, a *Streptocuccus pneumoniae* capsular saccharide, Enterococcal capsular saccharide or a *Staphylococcus aureus* capsular saccharide.

Embodiment 131: The hybrid oligosaccharide or polysaccharide of any one of embodiments 126-130 wherein the oligosaccharide repeat unit of A is the repeat unit of the capsular saccharide of a *Streptococcus pneumoniae* serotype 1, 2, 3, 4, 5, 6A, 6B, 7A, 7B, 7C, 8, 9A, 9L, 9N, 9V, 10A, 10B, 10C, 10F, 11A, 11B, 11C, 11D, 11F, 12A, 12B, 12F, 13, 14, 15A, 15B, 15C, 15F, 16A, 16F, 17A, 17F, 18A, 18B, 18C, 18F, 19A, 19B, 19C, 19F, 20, 21, 22A, 22F, 23A, 23B, 23F, 24A, 24B, 24F, 25A, 25F, 26, 27, 28A, 28F, 29, 31, 32A, 32F, 33A, 33B, 33C, 33D, 33F, 34, 35A, 35B, 35C, 35D, 35F, 36, 37, 38, 39, 40, 41A, 41F, 42, 43, 44, 45, 46, 47A, 47F or 48; or wherein the oligosaccharide repeat unit of A is the repeat unit of the capsular saccharide of a *Streptococcus pneumoniae* serotype 2, 3, 6A, 6B, 7A, 7B, 7C, 8, 9A, 9L, 9N, 9V, 10A, 10B, 10C, 10F, 11A, 11B, 11C, 11D, 11F, 13, 14, 15A, 15B, 15C, 15F, 16A, 16F, 17A, 17F, 18A, 18B, 18C, 18F, 19A, 19B, 19C, 19F, 20, 21, 22A, 22F, 23A, 23B, 23F, 24A, 24B, 24F, 25A, 25F, 26, 27, 28A, 28F, 29, 31, 32A, 32F, 33A, 33B, 33C, 33D, 33F, 34, 35A, 35B, 35C, 35D, 35F, 36, 37, 38, 39, 40, 41A, 41F, 42, 43, 44, 45, 46, 47A, 47F or 48.

Embodiment 132: A bioconjugate comprising a carrier protein linked to the hybrid oligosaccharide or polysaccharide of any one of embodiments 126-131.

3.1 Terminology

OPS: O polysaccharide; the O antigen of Gram-negative bacteria. OPS also are referred to herein as O antigen.

CP: Capsular polysaccharide

LPS: lipopolysaccharide.

waaL: the O antigen ligase gene encoding a membrane bound enzyme with an active site located in the periplasm. The encoded enzyme transfers undecaprenylphosphate (UPP)-bound O antigen to the lipid A core, forming lipopolysaccharide.

RU: repeat unit. As used herein, the RU is set equal to the biological repeat unit, BRU. The BRU describes the RU of an O antigen as it is synthesized in vivo.

Und-PP: undecaprenyl pyrophosphate.

LLO: lipid linked oligosaccharide.

As used herein, the term "bioconjugate" refers to conjugate between a protein (e.g., a carrier protein) and an antigen (e.g., an oligosaccharide or polysaccharide) prepared in a host cell background, wherein host cell machinery links the antigen to the protein (e.g., N-links).

The term "about," when used in conjunction with a number, refers to any number within ±1, ±5, or ±10% of the referenced number.

As used herein, the term "effective amount," in the context of administering a therapy (e.g., a composition described herein) to a subject refers to the amount of a therapy which has a prophylactic and/or therapeutic effect(s). In certain embodiments, an "effective amount" refers to the amount of a therapy which is sufficient to achieve one, two, three, four, or more of the following effects: (i) reduce or ameliorate the severity of a bacterial infection or symptom associated therewith; (ii) reduce the duration of a bacterial infection or symptom associated therewith; (iii) prevent the progression of a bacterial infection or symptom associated therewith; (iv) cause regression of a bacterial infection or symptom associated therewith; (v) prevent the development or onset of a bacterial infection, or symptom associated therewith; (vi) prevent the recurrence of a bacterial infection or symptom associated therewith; (vii) reduce organ failure associated with a bacterial infection; (viii) reduce hospitalization of a subject having a bacterial infection; (ix) reduce hospitalization length of a subject having a bacterial infection; (x) increase the survival of a subject with a bacterial infection; (xi) eliminate a bacterial infection in a subject; (xii) inhibit or reduce a bacterial replication in a subject; and/or (xiii) enhance or improve the prophylactic or therapeutic effect(s) of another therapy.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

As used herein, the term "subject" refers to an animal (e.g., birds, reptiles, and mammals). In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet (e.g., a dog, cat, horse, goat, sheep, pig, donkey, or chicken). In a specific embodiment, a subject is a human. The terms "subject," "individual," and "patient" may be used herein interchangeably.

As used herein, the term "donor oligosaccharide or polysaccharide" refers to an oligosaccharide or polysaccharide from which a oligosaccharide or polysaccharide is derived. Donor oligosaccharides and polysaccharides, as used herein, comprise a hexose monosaccharide (e.g., glucose) at the reducing end of the first repeat unit. Use of the term donor oligosaccharide or polysaccharide is not meant to suggest that an oligosaccharide or polysaccharide is modified in situ. Rather, use of the term donor oligosaccharide or polysaccharide is meant to refer to an oligosaccharide or polysaccharide that, in its wild-type state, is a weak substrate for oligosaccharyl transferase (e.g., PglB) activity or is not a substrate for oligosaccharyl transferase (e.g., PglB) activity. Exemplary donor oligosaccharides or polysaccharides include those from bacteria, including S. pneumoniae CP1, CP2, CP3, CP4, CP5, CP6 (A, B), CP7 (A, B, C), CP8, CP9 (A, L, N, V), CP10 (A, B, C, F), CP11 (A, B, C, D, F), CP12(A, B, F), CP13, CP14, CP15 (A, B, C, F), CP16 (A, F), CP17 (A, F), CP18 (A, B, C, F), CP19 (A, B, C, F), CP20, CP21, CP22 (A, F), CP23 (A, B, F), CP24 (A, B, F), CP25 (A, F), CP 26, CP27, CP28 (A, F), CP29, CP31, CP32 (A, F), CP33 (A, B, C, D, F), CP34, CP35 (A, B, C, D, F), CP36, CP37, CP38, CP39, CP40, CP41 (A, F), CP42, CP43, CP44, CP45, CP46, CP47 (A, F), and CP48. Those of skill in the art will readily be able determine whether an oligosaccharide or polysaccharide comprises a hexose monosaccharide (e.g., glucose) at the reducing end of the first repeat unit, and thus whether such an oligosaccharide or polysaccharide is a donor oligosaccharide or polysaccharide as encompassed herein.

As used herein, the term "hexose monosaccharide derivative" refers to a non-hexose monosaccharide that can be a substrate for oligosaccharyl transferase activity. In general, hexose monosaccharide derivative comprise a monosaccharide comprising an acetamido group at position 2. Exemplary hexose monosaccharide derivatives include GlcNAc, HexNAc, deoxy HexNAc, or 2,4-diacetamido-2,4,6-trideoxyhexose.

As used herein, the term "hybrid oligosaccharide or polysaccharide" refers to an engineered oligosaccharide or polysaccharide that does not comprise a hexose at the reducing end of the first repeat unit, but instead comprises a hexose monosaccharide derivative or a non-hexose monosaccharide at the reducing end of the first repeat unit.

BRIEF DESCRIPTION OF THE FIGURES

FIG. 4. Depicts components suitable for production and translocation of an S. pneumoniae CP14 engineered subunit, as well as data confirming production and translocation. 4A: schematic diagram of glycosyltransferases essential for synthesis of a glycoengineered CP14 subunit: the galactosyltransferase of Shigella boeydii wfeD, the GlcNAc transferase (wchL) of S. pneumoniae CP14, and the galactosyltransferase (wchM) of S. pneumoniae CP14. 4B: schematic diagram of glycosyltransferases that can synthesize a glycoengineered subunit of CP14, same as (A), but with the addition of the flippase gene (wzx) of S. pneumoniae CP14. 4C: silver staining of lipo-oligosaccharide after proteinase K digestion of E. coli SΦ874 transformed with a plasmid ("pGVX1190") comprising the genes of (A) (lane 1) or with a plasmid ("pGVX1366") comprising the genes of (B) (lane 2). Samples were resolved in 4-12% SDS-PAGE gel prior to silver-staining. The depicted results demonstrate that the flippase of S. pneumoniae capsular polysaccharide has relaxed glycan specificity and can translocate an engineered subunit from the cytoplasm into the periplasm. 4D: Structure of the engineered CP14 subunit. Arrows indicate the corresponding glycosyltransferases.

were collected and subjected to MS analysis. In the glycoengineered CP14 polymer, the engineered subunit found in all samples was the first subunit only, and no engineered subunit was identified as a polymer or at the middle of the polymer.

Figure 9:
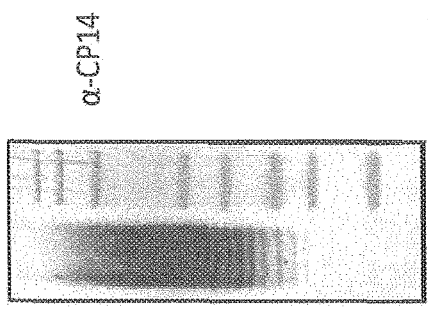
Figure 9:
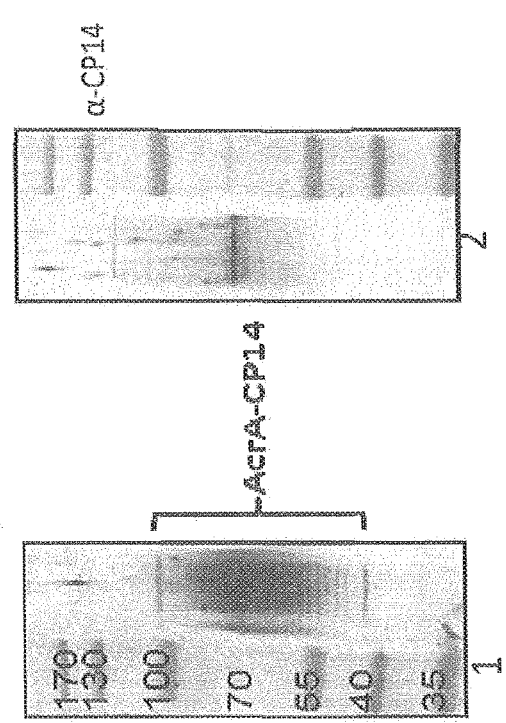

FIG. 9 demonstrates that PglB can transfer the engineered CP14 polymer, but not the wild type CP14 polymer, to a protein carrier. *E. coli* W3110 Colanic acid::CP14 ΔwaaL ΔwecA-wzzE and *E. coli* W3110 colonic acid:CP14 ΔwaaL were transformed with a plasmid comprising RcsA (activator of CP14 synthesis), pGVX970 (expressing PglB), pGVX1 (expressing AcrA the protein carrier); cells were harvested after induction. Western-blot analysis was performed on whole cell proteinase K digested and IMAC enriched periplasmic extracts that were resolved by SDS-PAGE (4-12% gel), electro blotted onto a nitrocellulose membrane, and incubated with a CP14 antibody. 9A: Western blot of proteinase K digested samples of transformed *E. coli* W3110 colanic acid:CP14 ΔwaaL (lane 1) and *E. coli* W3110 colonic acid::CP14 ΔwaaL ΔwecA-wzzE (lane 2). 9B: Western blot analysis of IMAC enriched samples of transformed *E. coli* W3110 colanic acid:CP14 ΔwaaL (lane 1) and *E. coli* W3110 colonic acid::CP14 ΔwaaL ΔwecA-wzzE (lane 2). In panel A all strains produced LLO and were recognized by anti CP14 antibody. However, in panel B, glycoprotein (CP14-AcrA) only was detected in strain *E. coli* W3110 Colanic Acid::CP14, ΔwaaL and not *E. coli* W3110 Colanic Acid::CP14, ΔwaaL, ΔwecA-wzzE, which cannot produce the CP14 engineering subunit due to lack of wecA (encoding priming transferase that adds GlcNAc to UndP) and therefore produces only the wild-type CP14 structure (which is not a substrate for PglB due to the presence of a hexose at the reducing end of the first repeat unit).

Figure 10:
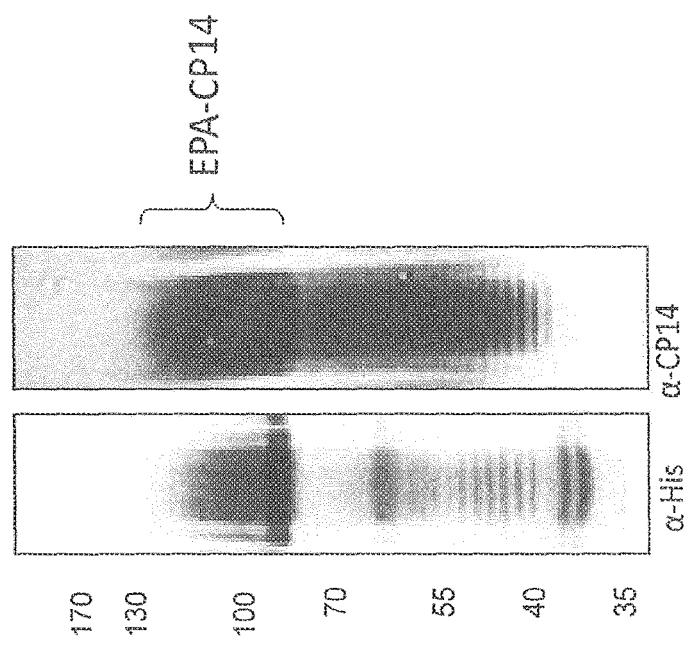

FIG. 10 demonstrates that the engineered CP14 polymer can be transferred by PglB to different carrier proteins. *E. coli* W3110 Colanic Acid::CP14, ΔwaaL was transformed with CP14 engineering plasmid (pGVX1433) and a plasmid for expression of RcsA (pGVX970, expressing PglB) and pGVX538 (expressing carrier protein EPA). All samples were harvested after induction and the protein was extracted from the periplasm and enriched by IMAC. Enriched protein samples were resolved by SDS-PAGE (4-12% gel) and electro blotted onto a nitrocellulose membrane and incubated with an anti-His antibody (10A) or a CP14 antibody (10B) as a primary antibody.

Figure 11:
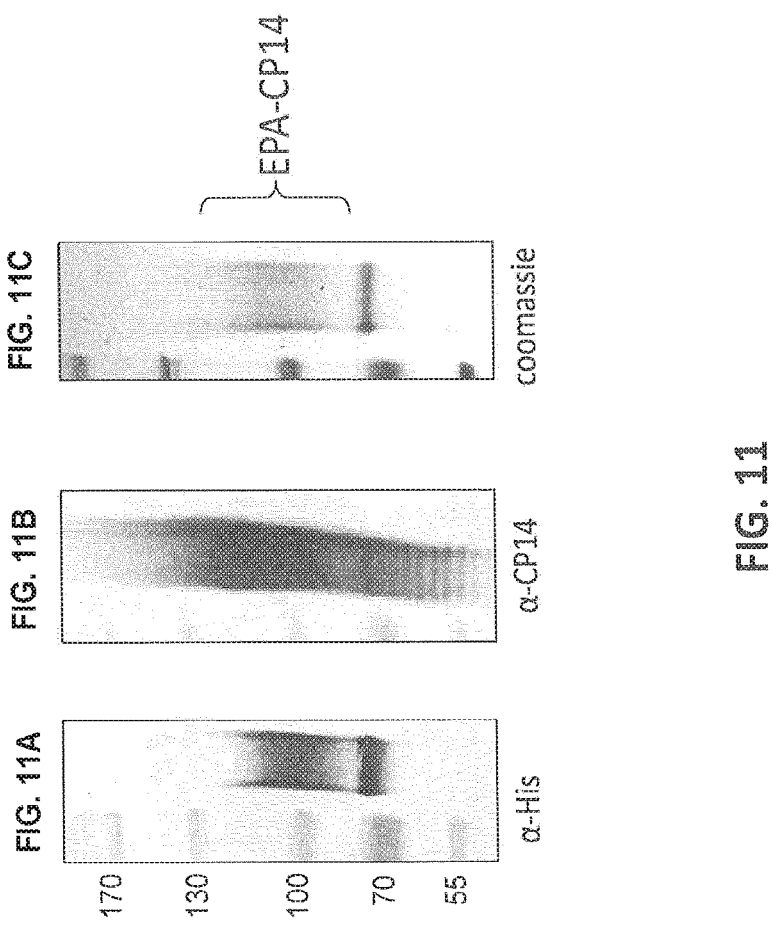

FIG. 11 demonstrates production and purification of EPA glycosylated with the engineered CP14 polymer. *E. coli* W3110 colonic acid::CP14 ΔwaaL was transformed with CP14 engineered plasmid (pGVX1433) and plasmids for expression of PglB (pGVX970) and EPA (pGVX538) and RcsA (for activating CP14 synthesis). The transformed strain was used for fermentation and the biomass was collected. Periplasmic proteins were extracted and subjected to IMAC and lectin affinity chromatography (*Ricinus communis* agglutinin-agarose) to purify the CP14-EPA conjugate to homogeneity. Purified samples were subjected to SDS-PAGE and electroblotted onto nitrocellulose. Western blot analysis was performed using anti-His (11A) or anti-CP14 serotyping antibodies (11B). 11C: a Coomassie stained gel of purified CP14-EPA bioconjugate.

Figure 12:
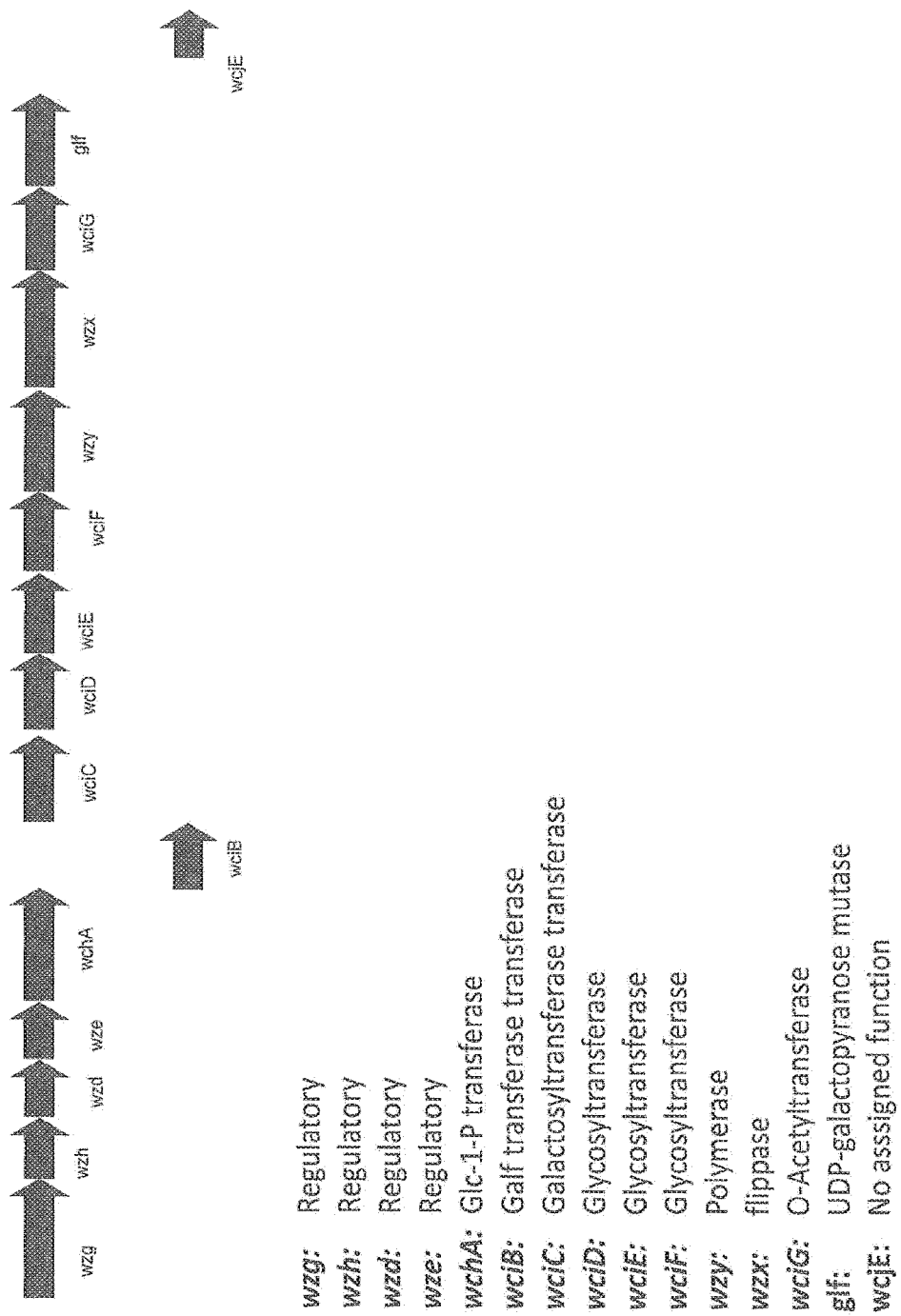

FIG. 12 depicts a schematic diagram of gene organization of the *S. pneumoniae* CP33F wild type cluster and the putative function of each gene. Part of the cluster (the genes except for the regulatory genes) was integrated into *E. coli* W3110 by replacing the colanic acid cluster of *E. coli* W3110.

FIG. 13 demonstrates development of *E. coli* strains expressing the *S. pneumoniae* CP33F capsule. 13A: *E. coli* W3110 colanic acid replaced by CP33F. Western blot analysis of the proteinase K digested whole cell extracts using CP33F typing antibody, all clones expressing CP33F. 13B: The lipopolysaccharide ligase (waaL) of the *E. coli* strain was replaced with pglB to generate *E. coli* W3310 CA:: CP33F waaL::pglB. The transformed strain was used for fermentation and the biomass was collected. Western blot analysis of the proteinase K digested whole cell extracts was performed using a CP33F typing antibody. Two different clones (13A, 13B) were tested.

FIG. 14 depicts a schematic diagram of a synthetic gene cluster that was synthesized for production of an engineered CP33F subunit (incorporated in plasmid pGVX2342). 14A: Arrows indicate genes that were assembled for production of the engineered CP33F subunit in plasmid pGVX81. Grey arrows represent genes from different *E. coli* strains which express Galf-transferases (wfdK and wbeY) that add Galf form UDP-Galf to GlcNAc-P-P-Undecaprenyl and galE (UPD-Galactose epimerase) and glf (UDP-galactopyranose mutase). Black arrows represent necessary *S. pneumoniae* genes for production of the CP33F cluster except for the priming Glc transferase wchA (instead, endogenous *E. coli* wecA acts as the priming transferase that assembles GlcNAc on the undecaprenolpyrophosphate and therefore is not part of the plasmid). 14B: structure of the engineered subunit of CP33F, arrows indicates corresponding glycosyltransferases from different bacteria.

Figure 15:
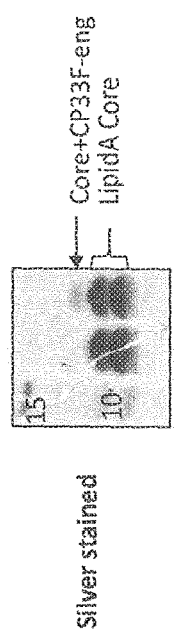
Figure 15:
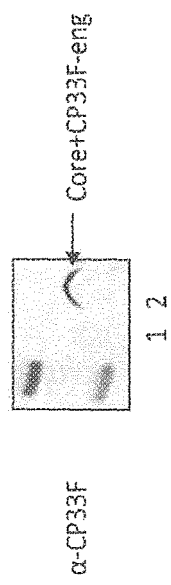

FIG. 15 demonstrates production and translocation of the *S. pneumoniae* CP33F engineered subunit. 15A: Silver staining of lipo-oligosaccharide after proteinase K digestion of *E. coli* W3110 transformed with plasmid pGVX2098, without CP33Fwzx flippase (lane 1) or with pGVX2342, containing CP33Fwzx flippase (lane 2). Samples were resolved in 4-12% SDS-PAGE gel prior to silver-staining or Western blot. 15B: Western blot analysis of the same samples as above using a typing CP33F antibody as the primary antibody. This data demonstrates that the flippase of *S. pneumoniae* capsular polysaccharide has relaxed glycan specificity and can translocate the engineered subunit from the cytoplasm into the periplasm.

Figure 16A:
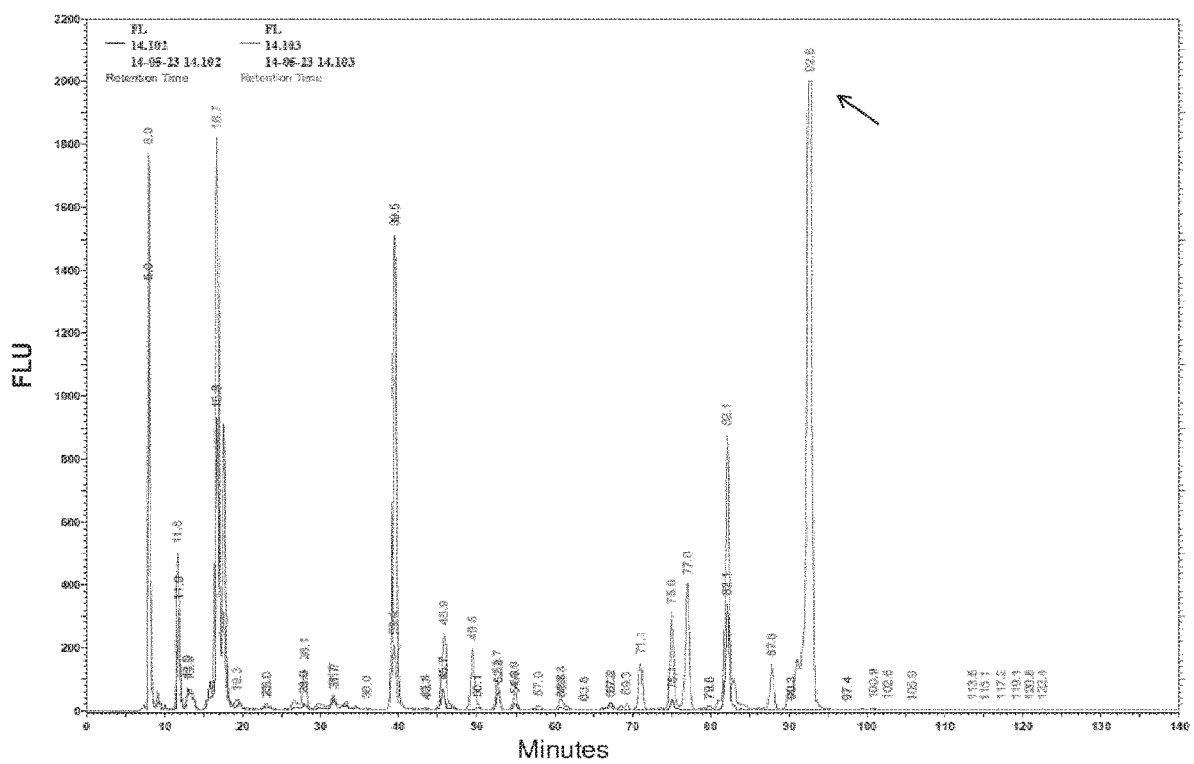
Figure 16B:
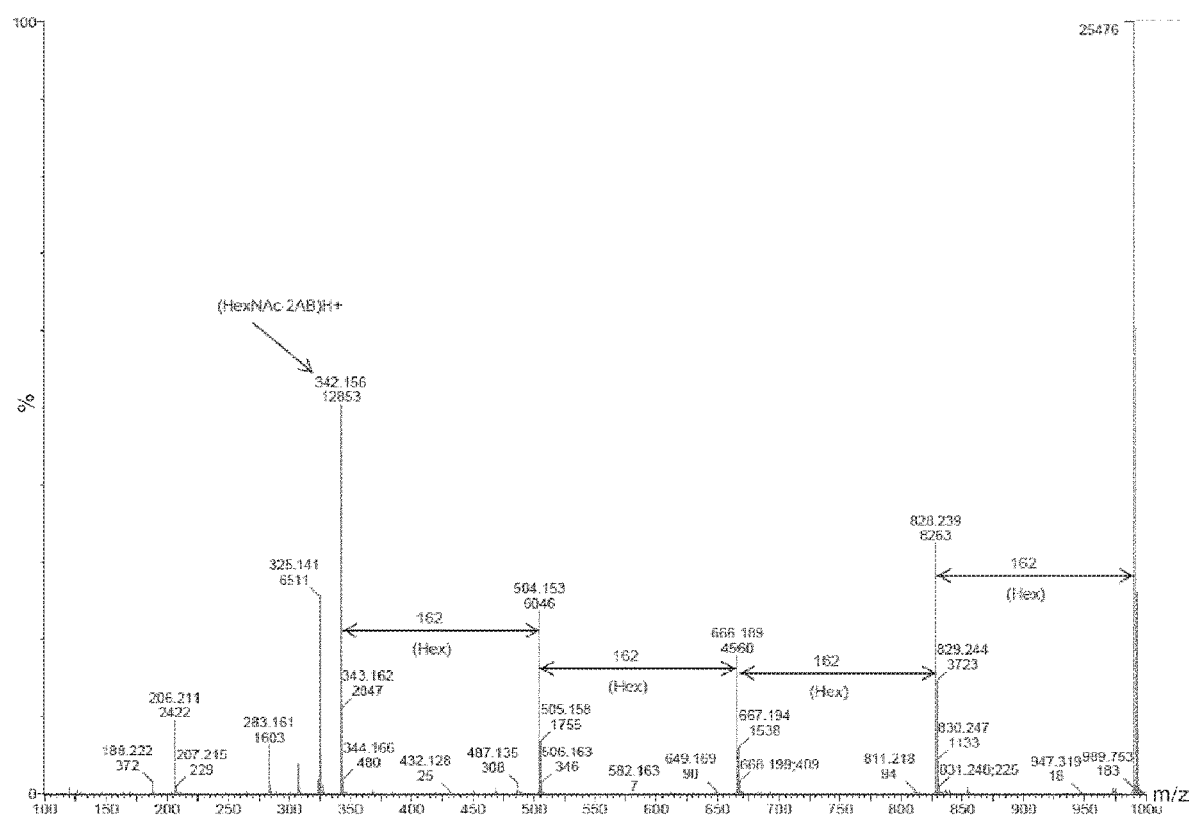

FIG. 16 demonstrates production of engineered CP33F subunit produced in *E. coli*. Lipid linked oligosaccharides (LLO) were extracted and labeled by 2AB and subjected to HPLC coupled with a florescent detector. 16A: HPLC chromatogram of CP33F engineered subunit. LLO were purified from *E. coli* SΦ874 ΔwaaL transformed with eng. CP33F plasmid, pGVX2342 or empty vector. Arrow indicates the peak corresponding to the CP33F engineered subunit that was collected for MS analysis. 16B: MS/MS analysis of the 70.5 min peak. Ion fragments matched with the expected structure of engineered CP33F subunit.

FIG. 17 demonstrates that the engineered CP33F subunit can be transferred by PglB. Western blot analysis of protein samples: *E. coli* W3110 ΔwaaL transformed with PglB expression plasmid (pGVX970), protein carrier AcrA expression plasmid (pGVX1) and empty plasmid (pGVX1387) or plasmid pGVX2306 (expressing engineered subunit of CP33F). Cells were harvested after induction and proteins were extracted from the periplasm, enriched by IMAC and purified samples were subjected to SDS-PAGE (4-12% gel) and electro blotted to a nitrocellulose membrane developed by anti-His (17A), or with a typing CP33F antibody (17B) as a primary antibody. Lane 1, protein sample from *E. coli* strain harboring empty plasmid; lane 2, protein sample from *E. coli* strain harboring engineering CP33F plasmid (pGVX2306).

Figure 18:
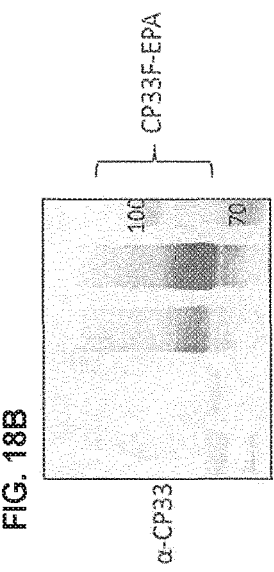
Figure 18:
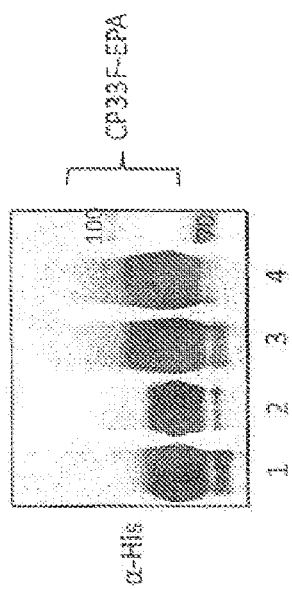
Figure 18:
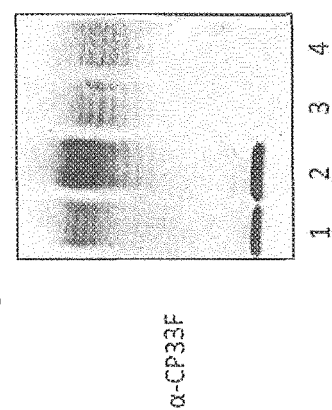

FIG. 18 demonstrates that PglB can transfer engineered CP33F polymer to a protein carrier but cannot transfer wild type CP33F. Western-blot analysis of proteinase K digested whole cells (18A) and IMAC enriched periplasmic extracts (18B and 18C) of *E. coli* W3110 colanic acid::CP33F waaL::PglB transformed with RcsA plasmid (activator of CP33F synthesis) and pGVX2310 expressing EPA (protein carrier) and empty vector (lane 1, 2) or CP33F engineering plasmid (pGVX2346) lane 3 and 4, respectively (Panel A and B). All samples were resolved by SDS-PAGE (4-12% gel), electro blotted onto a nitrocellulose membrane and incubated with typing CP33F antibody (18A and 18B) and with a-His antibody (18C). As shown in panel 18A all strains produced LLO recognized by anti-CP33F antibody; however, glycoprotein (CP33F-EPA) was only detected in the strain expressing CP33F Eng, verifying that PglB only can transfer CP33F modified so as to not to comprise a hexose at the reducing end of the first repeat unit.

FIG. 19. 19A: depicts a schematic diagram of gene organization of the *S. pneumoniae* CP14 wild type cluster and the putative function of each gene. The dotted line box indicates the part of the cluster that was integrated into the *E. coli* W3110 chromosome by replacing the *E. coli* W3110 colanic acid cluster. 19B: structure of one repeating unit (RU) of wild type CP14, with enzymes responsible for assembly indicated.

FIG. 20. 20A: depicts a schematic diagram of the synthetic cluster used for production of the engineered CP14 subunit. Arrows indicate genes that were assembled together for production of the engineered CP14 subunit in an arabinose-inducible plasmid. Light grey arrows represent the wciP (galactosysltransferase that assembles Gal from UDP-Gal to Glc) and wciQ (glucosyltransferase that assembles Glc from UDP-Glc to GalNAc-UndPP) genes from *E. coli* O21. The dark grey arrow represents the Z3206 epimerase that converts GlcNAc-UndPP (product of *E. coli* wecA) to GalNAc-UndPP (Rush J S, Alaimo C, Robbiani R, Wacker M, Waechter C J. J Biol Chem. 2010 Jan. 15; 285(3):1671-80). Black arrows represent wchL (encoding GlcNAc transferase) and wchM (encoding Galctosyltransferase) from *S. pneumoniae* CP14. The white arrow represents the *C. jejuni* flippase, pglK. 20B: structure of one repeating unit (RU) of hybrid CP14, with enzymes responsible for assembly indicated (here, a hexose monosaccharide derivative exists as the monosaccharide at the reducing end, with the complete wild-type CP14 repeat unit assembled onto the hexose monosaccharide derivative).

Figure 21:
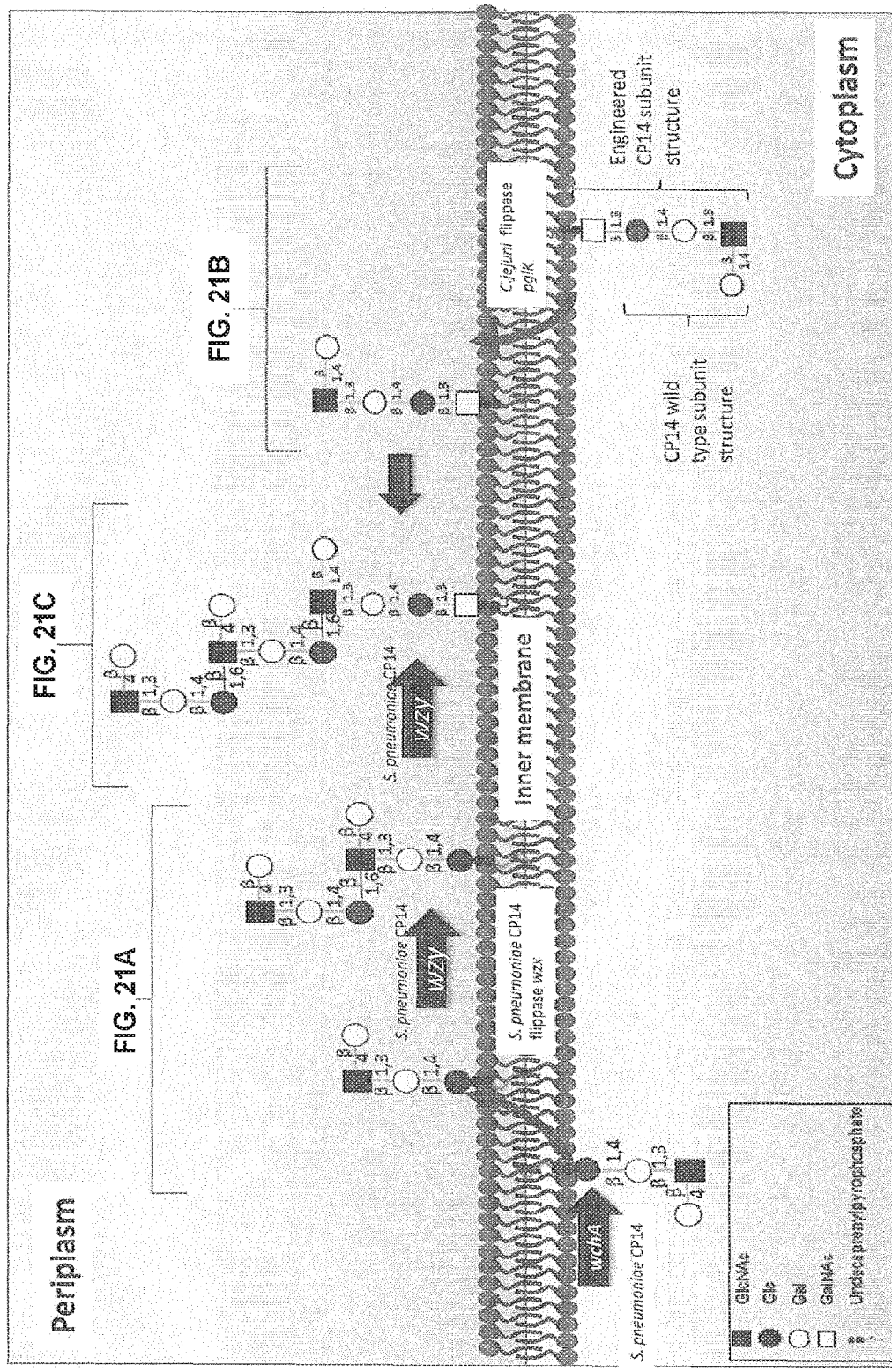

FIG. 21 depicts a schematic diagram that illustrates a method for production of a hybrid CP14 polymer that can be transferred by an oligosaccharyl transferase (e.g., *C. jejuni* PglB). 21A: shows the wild type biosynthetic pathway of CP14 that was incorporated into *E. coli* 21B: illustrates biosynthesis of one engineered subunit of CP14 using different glycosyltransferases to synthesize one complete wild type subunit of CP14 on GalNAc-undecaprenyl pyrophosphate. 21C: shows polymerization of wild type CP14 polysaccharide on top of one engineered subunit. This hybrid polymer is transferred by PglB with the high efficiency.

Figure 22:
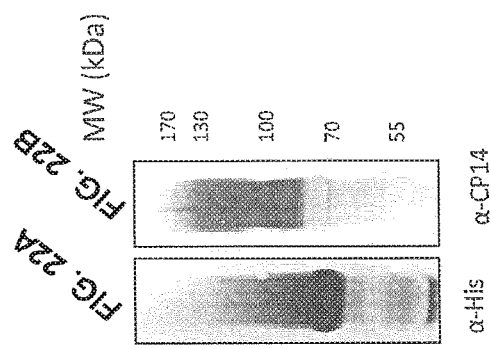

FIG. 22 demonstrates that PglB can transfer the engineered CP14 polymer to a protein carrier. *E. coli* W3110 colanic acid::CP14 ΔwaaL was transformed with RcsA plasmid (activator of CP14 synthesis), plasmid for production of engineered CP14 subunit, plasmid expressing PglB, and plasmid expressing EPA (a protein carrier). Cells were grown and harvested after induction. Periplasmic proteins were extracted and EPA conjugate enriched by affinity chromatography (purified IgG from Goat serum inject with unglycosylated purified EPA protein was coupled to Affi-Gel® from Bior-Rad). Enriched protein samples were resolved by SDS-PAGE (4-12% gel) and electro blotted onto a nitrocellulose membrane. 22A: blot incubated with anti-His monocolonal antibody. 22B: blot incubated with *S. pneumoniae* typing CP14 antibody. In both Western-blot analyses, ladder like bands were visualized which correspond to CP14-EPA conjugates.

Figure 23:
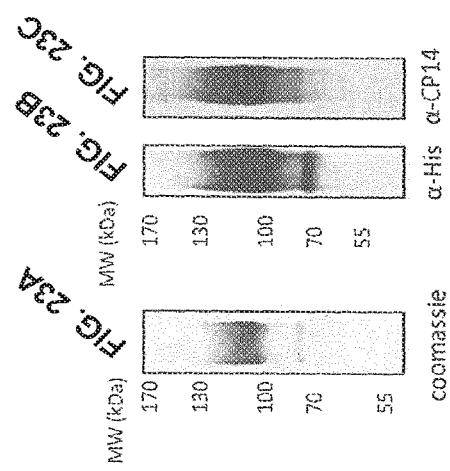

FIG. 23 demonstrates CP14-EPA purification. *E. coli* W3110 colanic acid::CP14ΔwaaL was transformed with plasmids for expression of RcsA (activator of CP14 synthesis), for production of the engineered subunit of CP14, expressing *C. jejuni* PglB (oligosaccharyltransferase), and EPA-6His (protein carrier). Transformed *E. coli* cells were grown in a bioreactor and cells were harvested after induction. Proteins were extracted from the periplasm by osmotic shock and purified with IMAC, lectin affinity chromatography (*Ricinus communis* agglutinin), size exclusion chromatography, and Source Q chromatography. Purified samples were resolved by SDS-PAGE (4-12% gel) and subjected to coomassie staining (23A) or electro-blotted on a nitrocellulose membranes, with ant-His monoclonal antibody as primary antbody (23B) or a typing anti-CP14 antibody used as primary antibody (23C).

Figure 24:
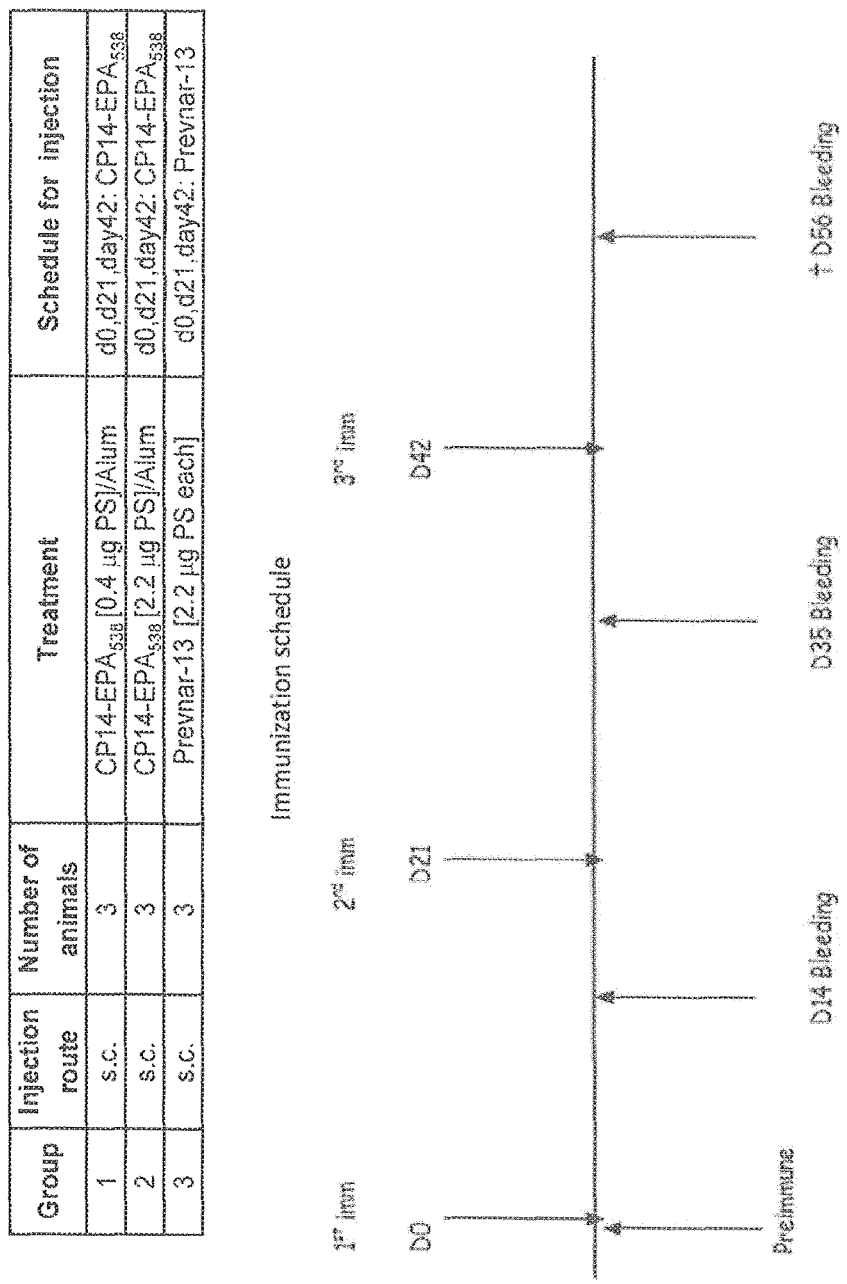

FIG. 24 depicts an experimental design for analysis of the immunogenicity of the CP14-EPA bioconjugates as compared to a known *Streptococcus pneumoniae* vaccine (Prevnar 13; Wyeth/Pfizer).

Figures 25, 25A, 25B:
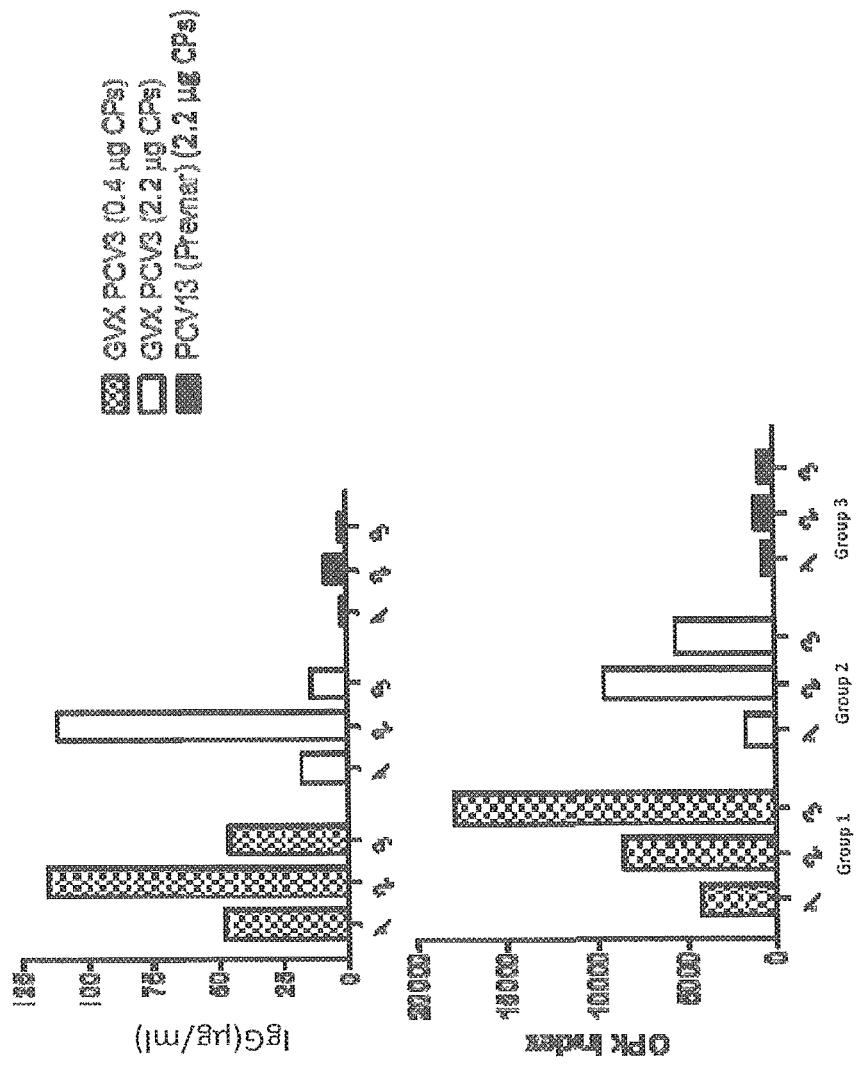

FIG. 25 demonstrates immunogenicity and functionality of antibody raised against the CP14-EPA bioconjugate as compared to Prevnar 13. CP14-EPA conjugate was injected along with aluminum hydroxide (adjuvant) at two dosages: 0.4 µg CP14 and 2.2 µg CP14, respectively to three different rabbits (see FIG. 24). As a control, Prevnar 13 (2.2 µg) was injected into three different rabbits. 25A: shows CP14 specific antibody concentration of rabbit. ELISA was performed using wild type CP14 capsular polysaccharide (normalized based on corresponding human sera). 25B: functionality of corresponding sera to 25A, shown by opsonophagocytosis index.

Figure 26:
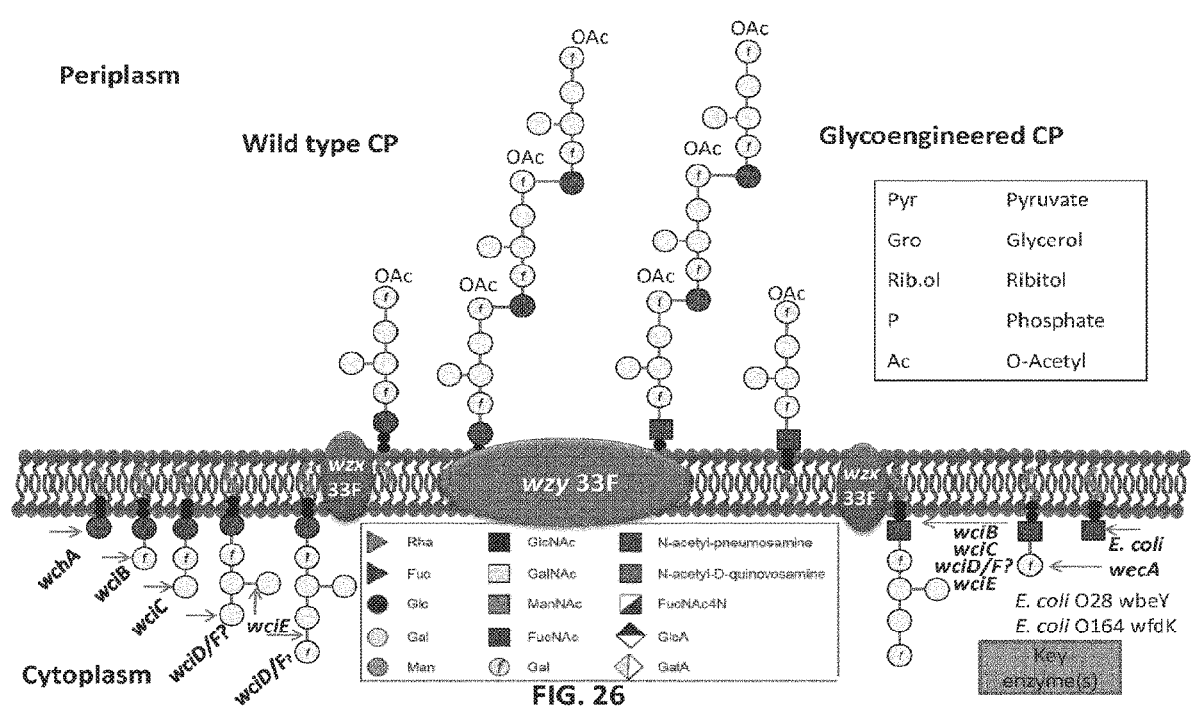

FIG. 26 depicts a cartoon showing the production of a glycoengineered (hybrid) capsular polysaccharide as compared to its wild-type counterpart, which comprises a hexose monosaccharide at the reducing end of the first repeat unit.

Figure 27:
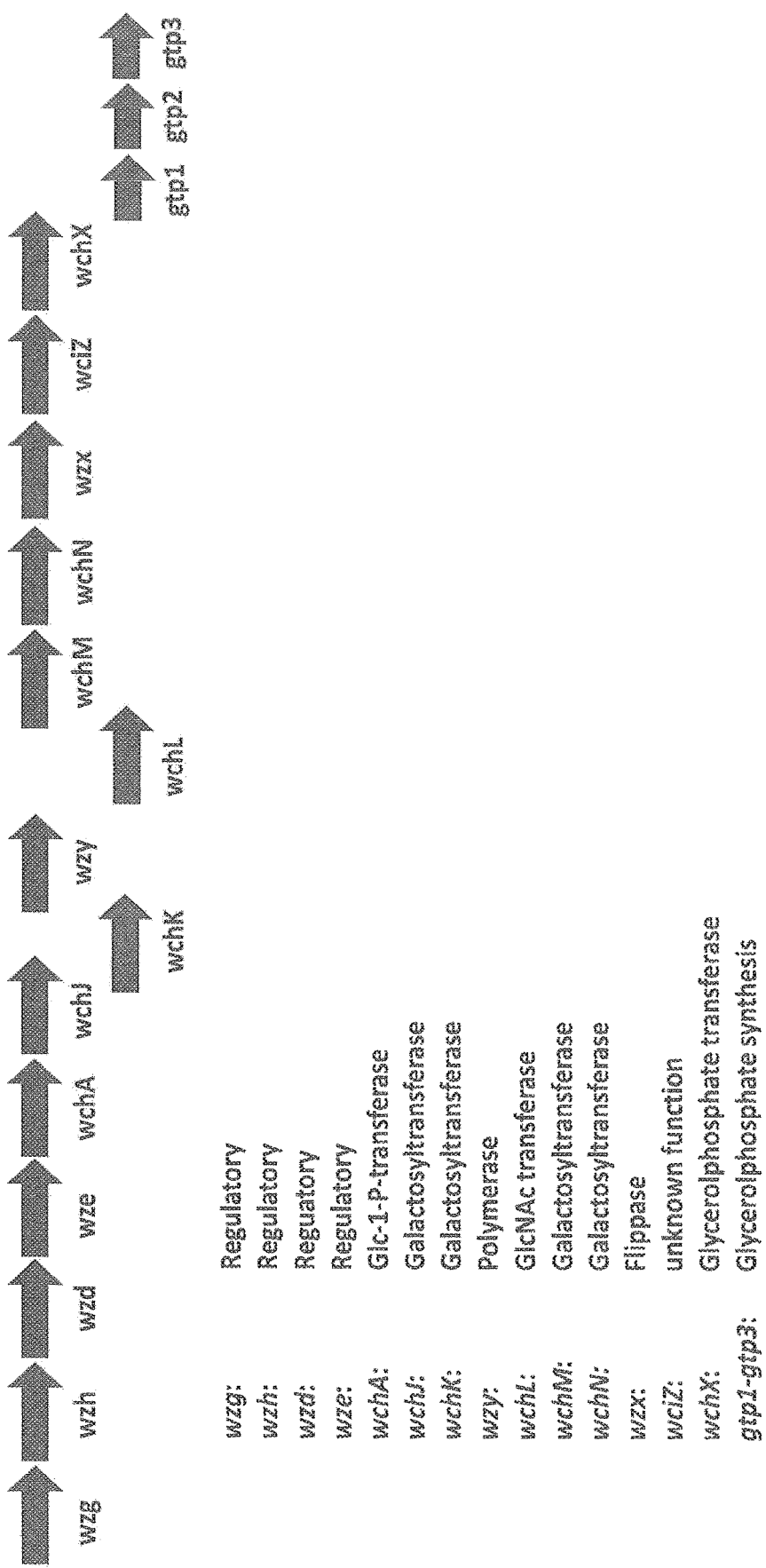

FIG. 27 depicts the *S. pneumoniae* CP15A gene cluster.

Figure 28:
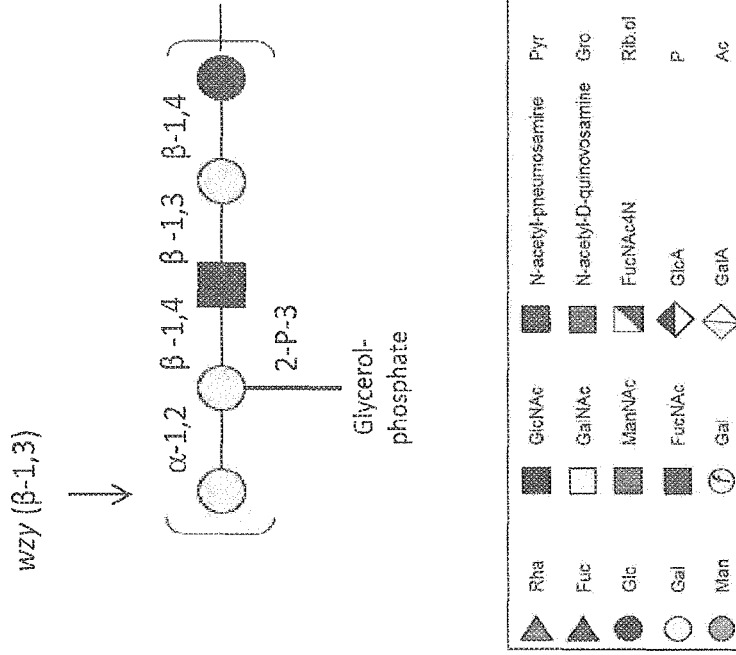

FIG. 28 depicts the repeating unit structure of the *S. pneumoniae* CP15A.

Figure 30:
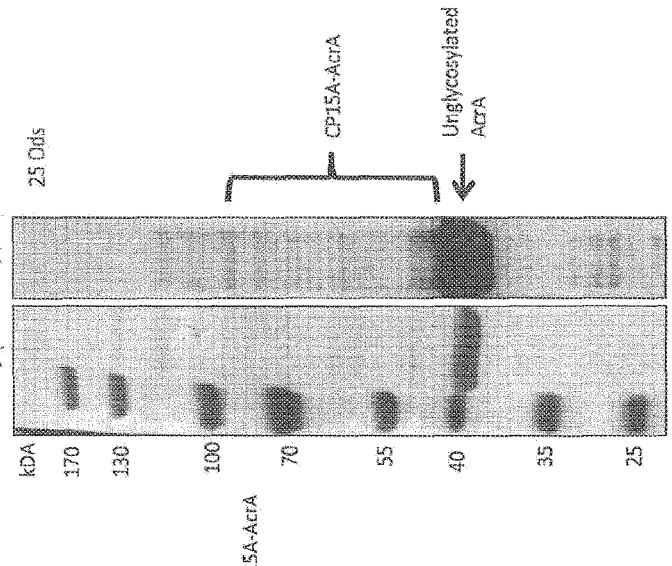
Figure 30:
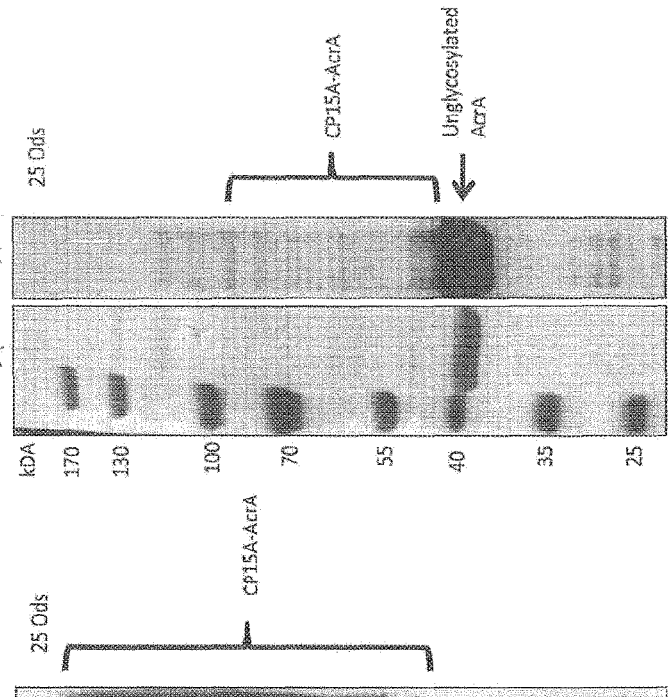
Figure 30:
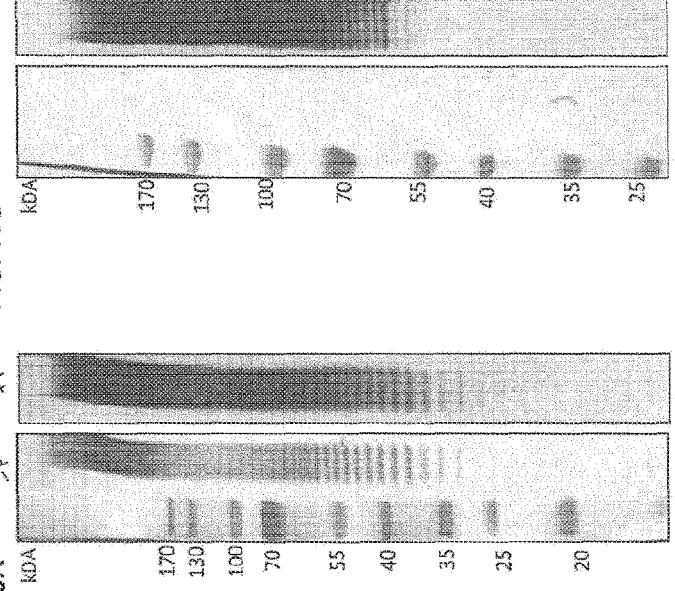

FIG. 29 depicts in A: the genetic organization of plasmid pGVXN3058 used to engineer CP15A and in B: the sugar structure of the engineered CP15A FIG. 30 demonstrates production of a CP15A-AcrA bioconjugate in the presence of the pGVXN3058 (Engineering) vector. 30A: Western blot analysis of whole cell proteinase K digested extracts using an anti-CP15A antibody; 30B: Western blot analysis of protein extracted from the periplasm and enriched by IMAC using an anti-CP15A antibody; 30C: Western blot analysis of protein extracted from the periplasm and enriched by IMAC using an anti His antibody.

DETAILED DESCRIPTION OF THE INVENTION

Pneumococcal capsular polysaccharides are synthetized on carrier lipids by the collaboration of a set of enzymes typically encoded in the CP cluster of *S. pneumoniae* cells (Whitfield C, Roberts I S: Structure, assembly and regulation of expression of capsules in *Escherichia coli*. Mol Microbiol 1999, 31(5):1307-1319). The synthesis of wzy dependent CP starts with the addition of a monosaccharide-phosphate to undecaprenylphosphate (Und-P) at the cytoplasmic side of the membrane. A short oligosaccharide is elongated by sequential addition of monosaccharides from activated sugar nucleotides by different glycosyltransferases and the lipid-linked oligosaccharide is flipped through the membrane by a flippase. The antigen-repeating unit (RU) is polymerized by an enzymatic reaction performed by the protein wzy. The polysaccharide is then transferred to the final acceptor structure. Polymerization and transport to the cell surface is believed to be controlled by a set of 3 to 4 enzymes which are located at the 5' end of the CPCP clusters.

Glycosyltransferases, the polymerase wzy, the flippase wzx, and the monosaccharide-phosphate transferase are encoded in most cases within the dexB to aliA cluster, whereas nucleotide activated monosaccharide biosynthetic pathways are encoded either elsewhere in the genome in the case of general housekeeping activities, and specifically within the CP cluster when the monosaccharides are specific for the CP (Bentley S D, Aanensen D M, Mavroidi A, Saunders D, Rabbinowitsch E, Collins M, Donohoe K, Harris D, Murphy L, Quail M A et al: Genetic analysis of the capsular biosynthetic locus from all 90 pneumococcal serotypes. *PLoS genetics* 2006, 2(3):e31).

Most biosynthetic pathways producing CP use nucleotide diphosphate (NDP) activated monosaccharides as substrates, namely UDP-Glc and UDP-GlcNAc. These NDP sugars are provided in Gram-negative and Gram-positive hosts by housekeeping genes, and thus are available as starting materials for synthesis of specific sugars. Biosynthetic genes for synthesis of specific NDP-sugars or other modifications are almost always encoded in CP clusters.

O antigen synthesis and CP synthesis differ at the last step of biosynthesis. O antigen is added to the Lipid A core by the ligase WaaL and is further transported to the outer membrane, whereas CP are present as a capsular structures on the cells. In average, the final O antigen sugar length is much shorter than CP.

*S. pneumoniae* CP are classified as group I CP due to the specific biochemical pathways leading to its synthesis. Gram-negative bacteria also contain group I CP pathways, which differ from pneumococcal group I clusters by the presence of additional membrane transporter protein genes responsible for outer membrane transport. For example, these are the colanic acid (CA) biosynthetic machinery gene clusters wca, (Stevenson G, Andrianopoulos K, Hobbs M, Reeves P R: Organization of the *Escherichia coli* K-12 gene cluster responsible for production of the extracellular polysaccharide colanic acid. *J Bacteriol* 1996, 178(16):4885-4893) and the K30 CP cluster (Whitfield C: Biosynthesis and assembly of capsular polysaccharides in *Escherichia coli*. Annu Rev Biochem 2006, 75:39-68).

A method for production of wild type capsular polysaccharide of *Streptococcus pneumoniae* via chromosomal integration and genetic modification of *E. coli* has been described. See International Patent Application No. WO2014/072405, incorporated by reference herein in its entirety. However, despite the successful production of wild type Gram-positive capsular polysaccharide, efficient production of pneumococcal CP bioconjugates in *E. coli* using oligosaccharyltransferases (*C. jejuni* PglB) was hampered due to the fact that over 90% of pneumococcal capsular polysaccharides contain hexose (e.g. Glucose) at the reducing end, which is a suboptimal substrate for PglB (Proc Natl Acad Sci USA. 2006 May 2; 103(18):7088-93).

As set forth in Section 3 above, the Examples below, and the appended claims, the inventor of this application has identified novel methods for production of modified oligosaccharides and polysaccharides, including pneumococcal capsular polysaccharides, which allow for biosynthesis of hybrid oligosaccharides and polysaccharides on a reducing monosaccharide attached to undecaprenol-pyrophosphate that is a suitable substrate for PglB. Thus, the methods described herein allow, for the first time, use of modified host cells in the production of high yields of bioconjugates linked to bacterial antigens (oligosaccharides and polysaccharides) that normally are not substrates for oligosaccharyl transferases (or are weak substrates for oligosaccharyl transferases), e.g., PglB (e.g, PglB from *C. jejuni*).

In one embodiment, provided herein is an engineered Gram-negative bacterium for the production of a polysaccharide, wherein the Gram-negative bacterium comprises a pathway of a capsular polysaccharide gene cluster which is integrated in chromosome of a Gram-negative bacterium. In certain embodiments, the Gram-negative bacterium comprises at least 25%, 50%, 75%, 85%, 90%, or at least 95% of the open reading frames of the capsular polysaccharide gene cluster. In certain embodiments, the Gram-negative bacterium comprises a complete capsular polysaccharide gene cluster. In certain embodiments, the polysaccharide comprises an epitope of the capsular polysaccharide.

In one embodiment, provided herein is a Gram-negative bacterium for the production of an engineered subunit, wherein the Gram-negative bacterium comprises a pathway for production of engineered repeating unit of a capsular polysaccharide. In certain embodiments, the Gram-negative bacterium comprises at least 25%, 50%, 75%, 85%, 90%, or at least 95% of the open reading frames of the capsular polysaccharide gene cluster. In certain embodiments, the Gram-negative bacterium comprises several genes encoding glycosyltransferases from different Gram-negative and positive bacteria.

In certain embodiments, the Gram-negative bacterium of the preceding paragraph is selected from the group consisting of *Escherichia* species, *E. coli*, *Shigella* species, *Klebsiella* species, *Salmonella* species, *Yersinia* species, *Neisseria* species, *Vibrio* species, *Proteus* species, *Pseudomonas* species, *Aeromonas* species, and *Proteus* species. In a specific embodiment, the Gram-negative bacterium is *E. coli*.

In certain embodiments, the Gram-positive bacterium of the preceding paragraph is selected from the group consisting of *Streptococcus* species, *Staphylococcus* species, *Bacillus* species, *Enterococcus* species and *Lactococcus* species.

In certain embodiments, capsular polysaccharide gene cluster of a Gram-positive bacterium that is engineered into the Gram-negative bacterium of any one of the preceding paragraphs is *Streptococcus pneumoniae*. In a specific embodiment, the *S. pneumoniae* regulatory gene is from *S. pneumoniae* Type 14. In a specific embodiment, the *S. pneumoniae* regulatory gene is from *S. pneumoniae* Type 33F.

In a specific embodiment of the present invention, the *S. pneumoniae* regulatory genes are from *S. pneumoniae* Type 8, 12F, 15A, 16F, 22F, 23A, 24F, 31, 33F, 35B and 38.

In certain embodiments, the Gram-negative bacterium of any of the preceding paragraphs comprises an oligosaccharyltransferase. In a specific embodiment, the oligosaccharyltransferase is heterologous to the Gram-negative bacterium.

In certain embodiments, the Gram-negative bacterium of any of the preceding paragraphs comprises at least one heterologous glycosyltransferase. In a specific embodiment, the heterologous glycosyltransferase is a prokaryotic glycosyltransferase. In a specific embodiment, the glycosyltransferase is obtained from the same Gram-positive bacterium as the regulatory gene.

In certain embodiments, the Gram-negative bacterium of any of the preceding paragraphs comprises a deletion or inactivation of one or more genes native to the Gram-negative bacterium. In a specific embodiment, the one or more deleted genes comprise the waaL gene. In a specific embodiment, the one or more deleted genes comprise all genes associated with O antigen biosynthesis in the Gram-negative bacterium.

In certain embodiments, the Gram-negative bacterium of any of the preceding paragraphs comprises replacement of one or more genes native to the Gram-negative bacterium. In a specific embodiment, the one or more replaced genes comprise the waaL gene. In a specific embodiment, waaL replaced by an oligosaccharyltransferase. In a specific embodiment, waaL replaced by C. jejuni pglB.

In certain embodiments, the Gram-negative bacterium of any of the preceding paragraphs comprises a nucleic acid encoding a carrier protein comprising a consensus sequence for glycosylation. In a specific embodiment, the nucleic acid encoding the carrier protein is heterologous to the Gram-negative bacterium. In a specific embodiment, the carrier protein is detoxified exotoxin A from *P. aeruginosa*, CRM197, Diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, *C. jejuni* natural glycoproteins, and *S. pneumoniae* pneumolysin. In a specific embodiment, the carrier protein is an *S. pneumoniae* protein, e.g., *S. pneumoniae* pneumolysin, *S. pneumoniae* NOX, *S. pneumoniae* PspA, *S. pneumoniae* PcpA, *S. pneumoniae* PhtD, *S. pneumoniae* PhtE, *S. pneumoniae* Ply, or *S. pneumoniae* LytB. In a specific embodiment, the carrier protein is conjugated to the polysaccharide by an oligosaccharyl transferase.

In certain embodiments, the glycosyltransferases genes engineered into the -negative bacterium to produce one of the following capsular polysaccharide engineered subunit: *S. pneumoniae* CP1, CP2, CP3, CP4, CP5, CP6 (A and B), CP7 (A,B, C), CP8, CP9 (A, L,N, V), CP10 (A,B,C,F), CP11 (A, B,C,D,F), CP12(A,B,F), CP13, CP14, CP15(A,B,C,F), CP16(A,F), CP17(A,F), CP18(A,B,C,F), CP19(A,B,C,F), CP20,CP21, CP22(A,F), CP23(A,B,F), CP24(A,B,F), CP25 (A,F), CP26, CP27,CP28(A,F), CP29, CP31, CP32(A,F), CP33(A,B,C,D,F), CP34, CP35(A,B,C,D,F), CP36, CP37, CP38, CP39, CP40, CP41(A,F), CP42, CP43, CP44, CP45, CP46, CP47(A,F), or CP48; or *Staphylococcus aureus* CP5, or CP8; *Streptococcus agalactiae* (group B, GBS) CPIa, CPIb, CPII, CPIII, CPIV, CPV, CPVI, CPVII, or CPVIII; or *Enterococcus faecalis* CPA, CPB, CPC, or CPD.

In a specific embodiment, the Gram-negative bacterium of the preceding paragraph comprises an oligosaccharyl transferase. In a specific embodiment, the oligosaccharyl transferase is heterologous to the Gram-negative bacterium.

In a specific embodiment, the Gram-negative bacterium of the preceding paragraphs comprises at least one glycosyltransferase that is heterologous to the Gram-negative bacterium. In a specific embodiment, the glycosyltransferase is a prokaryotic glycosyltransferase. In a specific embodiment, the glycosyltransferase is an archaea or eukaryotic glycosyltransferase.

In a specific embodiment, the Gram-negative bacterium of the preceding paragraphs comprises a nucleic acid encoding a carrier protein comprising a consensus sequence for glycosylation. In a specific embodiment, the nucleic acid encoding the carrier protein is heterologous to the Gram-negative bacterium. In a specific embodiment, the carrier protein is detoxified exotoxin A from *P. aeruginosa*, CRM197, Diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, and *C. jejuni* natural glycoproteins. In a specific embodiment, the carrier protein is conjugated to the polysaccharide by the oligosaccharyl transferase.

In a specific embodiment, the polysaccharide of the Gram-positive bacterium of the preceding paragraphs is a capsular polysaccharide of *Streptococcus pneumoniae*.

In a specific embodiment, the polysaccharide of the Gram-negative bacterium of the preceding paragraphs is an O antigen of *E. coli* (O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, O187), *Salmonella* sp (*S. enterica* subsp. *Enterica*, *S. enterica* subsp. *Salamae*, *S. enterica* subsp. *arizonae*, *S. enterica* subsp. *Diarizonae*, *S. enterica* subsp. Houtenae, *S. bongori*, and *S. enterica* subsp. *Indica*, and O types 1-67, *Pseudomonas* sp (*P. aeruginosa* O serotypes 1-20), *Klebsiella* sp. (particularly *K. pneumonia* serotypes O1, O2 (and subserotypes), O3, O4, O5, O6, O7, O8, O9, O10, O11, O12), Acinetobacter O antigens (in particular *A. baumannii* O antigens), *Chlamydia trachomatis* O antigens (serotypes A, B, C, D, E, F, G, H, I J, K, L1, L2, L3), *Vibrio cholera* O antigens O1 to 155, *Listeria* sp., in particular *L. monocytogenes* type 1, 2, 3, 4 and subserotypes thereof, *Legionella pneumophila* serotypes 1 to 15 O antigens, *Bordetella parapertussis* O antigens, *Burkholderia mallei* and *pseudomallei* O antigens, *Francisella tularensis*, *Campylobacter* sp. (*C. jejuni*); Capsular polysaccharides of *Clostridium difficile* (serotypes A, G, H, K, S1, S4, D, Cd-5, and *C. perfringens* serotypes A, B, C, D and E), *Staphylococcus aureus* type 5 and 8, *Streptococcus pyrogenes* (group B streptococcus capsular serotype polysaccharides), *E. coli*, *Streptococcus agalacticae* (group A streptococcal capsular polysaccharides), *Neisseria meningitidis* (serotypes A, B, C, W, Y, X), *Candida albicans*, *Haemophilus influenza*, *Enterococcus faecalis* capsular polysaccharides type I-V; and other surface polysaccharide structures, e.g. the *Borrelia burgdorferi* glycolipids), *Neisseria meningitidis* pilin O glycan and lipooligosaccharide (LOS), *Haemophilus influenza* LOS, Leishmania major lipophosphoglycan, tumor associated carbohydrate antigens, *Malaria glycosyl* phosphatidylinositol, or mycobacterium *Tuberculosis arabinomannan*.

In a specific embodiment, a glycosyltransferase is from polysaccharide gene cluster of the Gram-negative bacterium of the preceding paragraphs is an O antigen of *E. coli* (O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, O187), *Salmonella* sp (*S. enterica* subsp. *Enterica*, *S. enterica* subsp. *Salamae*, *S. enterica* subsp. *arizonae*, *S. enterica* subsp. *Diarizonae*, *S. enterica* subsp. *Houtenae*, *S. bongori*, and *S. enterica* subsp. *Indica*, and O types 1-67, *Pseudomonas* sp (*P. aeruginosa* O serotypes 1-20), *Klebsiella* sp. (particularly K. pneumonia serotypes O1, O2 (and subserotypes), O3, O4, O5, O6, O7, O8, O9, O10, O11, O12), Acinetobacter O antigens (in particular *A. baumannii* O antigens), *Chlamydia trachomatis* O antigens (serotypes A, B, C, D, E, F, G, H, I J, K, L1, L2, L3), *Vibrio cholera* O antigens O1 to 155, *Listeria* sp., in particular *L. monocytogenes* type 1, 2, 3, 4 and subserotypes thereof, *Legionella pneumophila* serotypes 1 to 15 O antigens, *Bordetella parapertussis* O antigens, *Burkholderia mallei* and *pseudomallei* O antigens, *Francisella tularensis*, *Campylobacter* sp. (*C. jejuni*); Capsular polysaccharides of *Clostridium difficile* (serotypes A, G, H, K, S1, S4, D, Cd-5, and *C. perfringens* serotypes A, B, C, D and E), *Staphylococcus aureus* type 5 and 8, *Streptococcus pyogenes* (group B streptococcus capsular serotype polysaccharides), *E. coli*, *Streptococcus agalacticae* (group A streptococcal capsular polysaccharides), *Neisseria meningitidis* (serotypes A, B, C, W, Y, X), *Candida albicans*, *Haemophilus influenza*, *Enterococcus faecalis* capsular polysaccharides type I-V; and other surface polysaccharide structures, e.g. the *Borrelia burgdorferi* glycolipids), *Neisseria meningitidis* pilin O glycan and lipooligosaccharide (LOS), *Haemophilus influenza* LOS, Leishmania major lipophosphoglycan, tumor associated carbohydrate antigens, malaria glycosyl phosphatidylinositol, or mycobacterium Tuberculosis arabinomannan. Teichoic acid and exopolysaccharide from *Staphylococcus aureus, Streptococcus pyogenes, Streptococcus agalacticae, C. perfringens, L. lactis, L. cremoris*.

In specific embodiments, provided herein is a recombinant glycoprotein produced by the Gram-negative bacterium of any one of the preceding paragraphs.

In specific embodiments, provided herein is a method of producing a recombinant glycoprotein comprising culturing the Gram-negative bacterium of any one of the preceding paragraphs under conditions suitable for the production of proteins. In a specific embodiment, the method further comprises purifying the recombinant glycoprotein.

In certain embodiments, different homologous and heterologous glycosyltransferases have been combined in vivo to generate engineering capsular polysaccharides repeating unit of *S. pneumoniae* CP1, CP2, CP3, CP4, CP5, CP6 (A and B), CP7 (A,B, C), CP8, CP9 (A, L,N, V), CP10 (A,B,C,F), CP11 (A, B,C,D,F), CP12(A,B,F), CP13, CP14 CP15(A,B,C,F), CP16(A,F), CP17(A,F), CP18(A,B,C,F), CP19(A,B,C,F), CP20,CP21, CP22(A,F), CP23(A,B,F), CP24(A,B,F), CP25(A,F), CP26, CP27,CP28(A,F), CP29, CP31, CP32(A,F), CP33(A,B,C,D,F), CPS34, CP35(A,B,C, D,F), CP36, CP37, CP38, CP39, CP40, CP41(A,F), CP42, CP43, CP44, CP45, CP46, CP47(A,F), CPS48 and all the additional capsules as mentioned in (Bentley S D, Aanensen D M, Mavroidi A, Saunders D, Rabbinowitsch E, Collins M, Donohoe K, Harris D, Murphy L, Quail M A et al: Genetic analysis of the capsular biosynthetic locus from all 90 pneumococcal serotypes. *PLoS genetics* 2006, 2(3):e31). Specifically, these capsular polysaccharides include *S. pneumoniae* CP14 and CP33F In a specific embodiment of the present invention, a vaccine product comprises engineering capsular polysaccharides repeating unit of *S. pneumoniae* serotypes CP8, CP15A, CP16F, CP22F, CP23A, CP24F, CP31, CP33F, CP35B and CP38.

In other embodiments, capsular polysaccharides of other Gram-positive bacteria with hexose or any other monosaccharide can be modified using the methods of the present invention. Other Gram-positive bacteria include *Staphylococcus aureus* and *Streptococcus agalactiae* (GBS). Examples of such capsular polysaccharides include *S. aureus* CP5, CP8, *S. agalactiae* (group B, GBS) CPIa, CPIb, CPII, CPIII, CPIV, CPV, CPVI, CPVII, CPVIII, *Enterococcus faecalis* CPA, CPB, CPC, CPD.

In certain embodiments, the bacterial host cells described herein and the conjugates produced by such bacterial host cells described herein possess advantageous properties. For example, in certain embodiments, the bacterial host cells described herein, which comprise regulatory genes derived from Gram-positive bacteria, wherein said regulatory genes are involved in oligo- or polysaccharide biosynthesis, are able to produce sugar antigens, e.g., oligo- and/or polysaccharides, of increased length as a result of the presence of said regulatory genes. In addition, the bacterial host cells described herein are able to produce increased amounts of sugar antigens, e.g., oligo- and/or polysaccharides, as compared to Gram-negative bacterial host cells lacking regulatory genes derived from Gram-positive bacteria. Each of these characteristics is advantageous in that the conjugates produced by the bacterial cells have a higher sugar antigen to protein ratio and because the bacterial cells produce a greater number of conjugates.

In certain embodiments, a bacterial host cell described herein produces about 5%, 10%, 15%, 20%, about 25%, about 30%, about 40%, about 50%, or greater than 50% more conjugates than a bacterial host cell having the same properties but lacking a regulatory gene from a Gram positive bacteria that is involved in oligo- or polysaccharide biosynthesis. In certain embodiments, a bacterial host cell described herein produces 5% to 10%, 10% to 20%, 20% to 30%, 30% to 40%, or 40% to 50% more conjugates than a bacterial host cell having the same properties but lacking a regulatory gene from a Gram positive bacteria that is involved in oligo- or polysaccharide biosynthesis.

In certain embodiments, a bacterial host cell described herein produces about 5%, 10%, 15%, 20%, about 25%, about 30%, about 40%, about 50%, or greater than 50% more sugar antigens, e.g., oligo- and/or polysaccharides, than a bacterial host cell having the same properties but lacking a regulatory gene from a Gram positive bacteria that is involved in oligo- or polysaccharide biosynthesis. In certain embodiments, a bacterial host cell described herein produces 5% to 10%, 10% to 20%, 20% to 30%, 30% to 40%, or 40% to 50% more sugar antigens, e.g., oligo- and/or polysaccharides, than a bacterial host cell having the same properties but lacking a regulatory gene from a Gram positive bacteria that is involved in oligo- or polysaccharide biosynthesis.

In certain embodiments, a bacterial host cell described herein produces sugar antigens, e.g., oligo- and/or polysaccharides, that are about 5%, 10%, 15%, 20%, about 25%, about 30%, about 40%, about 50%, or greater than 50% longer than the sugar antigens, e.g., oligo- and/or polysaccharides produced by a bacterial host cell having the same properties but lacking a regulatory gene from a Gram positive bacteria that is involved in oligo- or polysaccharide biosynthesis. In certain embodiments, a bacterial host cell described herein produces sugar antigens, e.g., oligo- and/or polysaccharides, that are 5% to 10%, 10% to 20%, 20% to 30%, 30% to 40%, or 40% to 50% longer than the sugar antigens, e.g., oligo- and/or polysaccharides produced by a bacterial host cell having the same properties but lacking a regulatory gene from a Gram positive bacteria that is involved in oligo- or polysaccharide biosynthesis.

Various assays can be used to characterize the conjugates described herein, e.g., characterize the carrier protein, attached sugar antigen(s) (e.g., oligo- and/or polysaccharide), or both, including, e.g., high performance size exclusion chromatography, isoelectric focusing, SDS-PAGE and Western Blot, molecular weight determination by MS, N terminal sequencing, amino acid analysis, reverse phase liquid chromatography, electrospray mass spectroscopy, tandem mass spectrometry (MS/MS), and peptide mapping by mass spectroscopy after tryptic digestion.

5.1 Host Cells

Any host cells known to those of skill in the art can be used to produce the hybrid oligosaccharides and polysaccharides described herein and bioconjugates comprising the hybrid oligosaccharides and polysaccharides described herein, including archea, prokaryotic host cells, and eukaryotic host cells. Exemplary prokaryotic host cells for use in production of the hybrid oligosaccharides and polysaccharides described herein and bioconjugates comprising the hybrid oligosaccharides and polysaccharides described herein include, without limitation, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species. In a specific embodiment, the host cell used to produce the hybrid oligosaccharides and polysaccharides described herein and bioconjugates hybrid oligosaccharides and polysaccharides described herein is *E. coli*.

In certain embodiments, the host cells used to produce the hybrid oligosaccharides and polysaccharides described herein and bioconjugates described herein are engineered to comprise heterologous nucleic acids, e.g., heterologous nucleic acids that encode one or more carrier proteins and/or heterologous nucleic acids that encode one or more proteins, e.g., genes encoding one or more proteins. In a specific embodiment, heterologous nucleic acids that encode proteins involved in glycosylation pathways (e.g., prokaryotic and/or eukaryotic glycosylation pathways) may be introduced into the host cells described herein. Such nucleic acids may encode proteins including, without limitation, oligosaccharyl transferases, epimerases, flippases, polymerases, and/or glycosyltransferases. Heterologous nucleic acids (e.g., nucleic acids that encode carrier proteins and/or nucleic acids that encode other proteins, e.g., proteins involved in glycosylation) can be introduced into the host cells described herein using any methods known to those of skill in the art, e.g., electroporation, chemical transformation by heat shock, natural transformation, phage transduction, and conjugation. In specific embodiments, heterologous nucleic acids are introduced into the host cells described herein using a plasmid, e.g., the heterologous nucleic acids are expressed in the host cells by a plasmid (e.g., an expression vector). In another specific embodiment, heterologous nucleic acids are introduced into the host cells described herein using the method of insertion described in International Patent application No. PCT/EP2013/068737 (published as WO 14/037585).

In certain embodiments, additional modifications may be introduced (e.g., using recombinant techniques) into the host cells described herein. For example, host cell nucleic acids (e.g., genes) that encode proteins that form part of a possibly competing or interfering glycosylation pathway (e.g., compete or interfere with one or more heterologous genes involved in glycosylation that are recombinantly introduced into the host cell) can be deleted or modified in the host cell background (genome) in a manner that makes them inactive/dysfunctional (i.e., the host cell nucleic acids that are deleted/modified do not encode a functional protein or do not encode a protein whatsoever). In certain embodiments, when nucleic acids are deleted from the genome of the host cells provided herein, they are replaced by a desirable sequence, e.g., a sequence that is useful for glycoprotein production.

Exemplary genes that can be deleted in host cells (and, in some cases, replaced with other desired nucleic acid sequences) include genes of host cells involved in glycolipid biosynthesis, such as waaL (see, e.g., Feldman et al., 2005, PNAS USA 102:3016-3021), the lipid A core biosynthesis cluster (waa), galactose cluster (gal), arabinose cluster (ara), colonic acid cluster (wc), capsular polysaccharide cluster, undecaprenol-p biosynthesis genes (e.g. uppS, uppP), und-P recycling genes, metabolic enzymes involved in nucleotide activated sugar biosynthesis, enterobacterial common antigen cluster, and prophage O antigen modification clusters like the gtrABS cluster

5.2 Carrier Proteins

Any carrier protein suitable for use in the production of conjugate vaccines (e.g., bioconjugates for use in vaccines) can be used herein, e.g., nucleic acids encoding the carrier protein can be introduced into a host cell provided herein for the production of a bioconjugate comprising a carrier protein linked to a hybrid oligosaccharide and polysaccharide. Exemplary carrier proteins include, without limitation, detoxified Exotoxin A of *P. aeruginosa* (EPA; see, e.g., Ihssen, et al., (2010) Microbial cell factories 9, 61), CRM197, maltose binding protein (MBP), Diphtheria toxoid, Tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin and detoxified variants thereof, *C. jejuni* AcrA, and *C. jejuni* natural glycoproteins. For EPA, various detoxified protein variants have been described in literature and could be used as carrier proteins.

In certain embodiments, the carrier proteins used in the generation of the bioconjugates described herein are modified, e.g., modified in such a way that the protein is less toxic and/or more susceptible to glycosylation. In a specific embodiment, the carrier proteins used in the generation of the bioconjugates described herein are modified such that the number of glycosylation sites in the carrier proteins is maximized in a manner that allows for lower concentrations of the protein to be administered, e.g., in an immunogenic composition, in its bioconjugate form.

In certain embodiments, the carrier proteins described herein are modified to include 1, 2, 3, 4, 5, 6, 7, 8, 9, 10, or more glycosylation sites than would normally be associated with the carrier protein (e.g., relative to the number of glycosylation sites associated with the carrier protein in its native/natural, e.g., "wild-type" state). In specific embodiments, introduction of glycosylation sites is accomplished by insertion of glycosylation consensus sequences (e.g., Asn-X-Ser(Thr), wherein X can be any amino acid except Pro; or Asp(Glu)-X-Asn-Z-Ser(Thr), wherein X and Z are independently selected from any natural amino acid except Pro (see WO 2006/119987)) anywhere in the primary structure of the protein. Introduction of such glycosylation sites can be accomplished by, e.g., adding new amino acids to the primary structure of the protein (i.e., the glycosylation sites are added, in full or in part), or by mutating existing amino acids in the protein in order to generate the glycosylation sites (i.e., amino acids are not added to the protein, but selected amino acids of the protein are mutated so as to form glycosylation sites). Those of skill in the art will recognize that the amino acid sequence of a protein can be readily modified using approaches known in the art, e.g., recombinant approaches that include modification of the nucleic acid sequence encoding the protein. In specific embodiments, glycosylation consensus sequences are introduced into specific regions of the carrier protein, e.g., surface structures of the protein, at the N or C termini of the protein, and/or in loops that are stabilized by disulfide bridges at the base of the protein. In certain embodiments, the classical 5 amino acid glycosylation consensus sequence may be extended by lysine residues for more efficient glycosylation, and thus the inserted consensus sequence may encode 5, 6, or 7 amino acids that should be inserted or that replace acceptor protein amino acids. In one particular embodiment a carrier protein is detoxified EPA comprising 4 consensus glycosylation sequences Asp/Glu-X-Asn-Z-Ser/Thr.

In certain embodiments, the carrier proteins used in the generation of the bioconjugates described herein comprise a "tag," i.e., a sequence of amino acids that allows for the isolation and/or identification of the carrier protein. For example, adding a tag to a carrier protein described herein can be useful in the purification of that protein and, hence, the purification of conjugate vaccines comprising the tagged carrier protein. Exemplary tags that can be used herein include, without limitation, histidine (HIS) tags (e.g., hexa histidine-tag, or 6XHis-Tag), FLAG-TAG, and HA tags. In certain embodiments, the tags used herein are removable, e.g., removal by chemical agents or by enzymatic means, once they are no longer needed, e.g., after the protein has been purified.

In certain embodiments, the carrier proteins described herein comprise a signal sequence that targets the carrier protein to the periplasmic space of the host cell that expresses the carrier protein. In a specific embodiment, the signal sequence is from *E. coli* DsbA, *E. coli* outer membrane porin A (OmpA), *E. coli* maltose binding protein (MalE), *Erwinia carotovorans* pectate lyase (PelB), FlgI, NikA, or *Bacillus* sp. endoxylanase (XynA), heat labile *E. coli* enterotoxin LTIIb, *Bacillus* endoxylanase XynA, or *E. coli* flagellin (FlgI).

5.3 Glycosylation Machinery

The host cells provided herein comprise, and/or can be modified to comprise, nucleic acids that encode genetic machinery (e.g., glycosyltransferases, flippases, polymerases, and/or oligosaccharyltransferases) capable of producing hybrid oligosaccharides and/or polysaccharides, as well as genetic machinery capable of linking such hybrid oligosaccharides and/or polysaccharides to carrier proteins.

Glycosyltransferases

The host cells provided herein comprise nucleic acids that encode glycosyltransferases that produce an oligosaccharide or polysaccharide repeat unit, wherein said repeat unit does not comprise a hexose at the reducing end, and wherein said oligosaccharide or polysaccharide repeat unit is derived from a donor oligosaccharide or polysaccharide repeat unit that comprises a hexose at the reducing end. One of skill in the art will readily be able to determine what glycosyltransferases can be engineered into a host cell so as to render the host cell capable of producing a repeat unit of a hybrid oligosaccharide or polysaccharide that is based on a donor oligosaccharide or polysaccharide of interest. Indeed, glycosyltransferases are well-known in the art.

In a specific embodiment, the host cells provided herein comprise a nucleic acid that encodes a glycosyltransferase that assembles a hexose monosaccharide derivative onto undecaprenyl pyrophosphate (UND-PP). Said glycosyltransferase can be derived from, e.g., *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species. In a specific embodiment, said glycosyltransferase is wecA.

In a specific embodiment, the host cells provided herein comprise nucleic acids that encode glycosyltransferases sufficient for synthesis of the donor oligosaccharide or polysaccharide repeat unit. Such glycosyltransferases will be readily apparent to one of skill in the art once the donor oligosaccharide or polysaccharide repeat unit in question has been selected. In a specific embodiment, said glycosyltransferases sufficient for synthesis of the repeat units of the donor oligosaccharide or polysaccharide comprise wchL and/or wchM from *S. pneumoniae* CP14. In a specific embodiment, said glycosyltransferases sufficient for synthesis of the repeat units of the donor oligosaccharide or polysaccharide comprise comprise wciC, wciD, wciE, and/or wciF from *S. pneumoniae* CP33F.

In a specific embodiment, the host cells provided herein comprise nucleic acids that encode one or more glycosyltransferases capable of adding a monosaccharide to the hexose monosaccharide derivative assembled on UND-PP. In a specific embodiment, said one or more glycosyltransferases capable of adding a monosaccharide to the hexose monosaccharide derivative is the galactosyltransferase (wfeD) from *Shigella boyedii*. In another specific embodiment, said one or more glycosyltransferases capable of adding a monosaccharide to the hexose monosaccharide derivative is the galactofuranosyltransferase (wbeY) from *E. coli* O28. In another specific embodiment, said one or more glycosyltransferases capable of adding a monosaccharide to the hexose monosaccharide derivative is the galactofuranosyltransferase (wfdK) from *E. coli* O167. In another specific embodiment, said one or more glycosyltransferases capable of adding a monosaccharide to the hexose monosaccharide derivative are the galactofuranosyltransferase (wbeY) from *E. coli* O28 and the galactofuranosyltransferase (wfdK) from *E. coli* O167.

In another specific embodiment, the host cells provided herein comprise nucleic acids that encode glycosyltransferases that assemble the donor oligosaccharide or polysaccharide repeat unit onto the hexose monosaccharide derivative.

In one embodiment, the glycosyltransferases that assemble the donor oligosaccharide or polysaccharide repeat unit onto the hexose monosaccharide derivative comprise a glycosyltransferase that is capable of adding the hexose monosaccharide present at the reducing end of the first repeat unit of the donor oligosaccharide or polysaccharide to the hexose monosaccharide derivative. Exemplary glycosyltransferases include galactosyltransferases (wciP), e.g., wciP from *E. coli* O21.

In one embodiment, the glycosyltransferases that assemble the donor oligosaccharide or polysaccharide repeat unit onto the hexose monosaccharide derivative comprise a glycosyltransferase that is capable of adding the monosaccharide that is adjacent to the hexose monosaccharide present at the reducing end of the first repeat unit of the donor oligosaccharide or polysaccharide to the hexose monosaccharide present at the reducing end of the first repeat unit of the donor oligosaccharide or polysaccharide. Exemplary glycosyltransferases include glucosyltransferase (wciQ), e.g., wciQ from *E. coli* O21.

Oligosaccharyl Transferases

Oligosaccharyl transferases transfer lipid-linked oligosaccharides to asparagine residues of nascent polypeptide chains that comprise an N-glycoxylation consensus motif, e.g., Asn-X-Ser(Thr), wherein X can be any amino acid except Pro; or Asp(Glu)-X-Asn-Z-Ser(Thr), wherein X and Z are independently selected from any natural amino acid except Pro (see WO 2006/119987). See, e.g., WO 2003/074687 and WO 2006/119987, the disclosures of which are herein incorporated by reference in their entirety.

In certain embodiments, the host cells provided herein comprise a nucleic acid that encodes an oligosaccharyl transferase. The nucleic acid that encodes an oligosaccharyl transferase can be native to the host cell, or can be introduced into the host cell using genetic approaches, as described above. The oligosaccharyl transferase can be from any source known in the art. In a specific embodiment, the oligosaccharyl transferase is an oligosaccharyl transferase from *Campylobacter*. In another specific embodiment, the oligosaccharyl transferase is an oligosaccharyl transferase from *Campylobacter jejuni* (i.e., pglB; see, e.g., Wacker et al., 2002, Science 298:1790-1793; see also, e.g., NCBI Gene ID: 3231775, UniProt Accession No. O86154). In another specific embodiment, the oligosaccharyl transferase is an oligosaccharyl transferase from *Campylobacter lari* (see, e.g., NCBI Gene ID: 7410986).

Flippases

In certain embodiments, a flippase (Wzx) is introduced into a host cell described herein (i.e., the flippase is heterologous to the host cell). Flippases of various organisms (e.g., bacterial flippases) are known in the art. Flippases translocate wild type repeating units and/or their corresponding engineered (hybrid) repeat units from the cytoplasm into the periplam of host cells (e.g., *E. coli*).

In a specific embodiment, a flippase of a capsular polysaccharide biosynthetic pathway is introduced into a host cell described herein.

In another specific embodiment, a flippase of a capsular polysaccharide biosynthetic pathway of *S. pneumoniae* is introduced into a host cell described herein. In certain embodiments, the flippase introduced into the host cells described herein is the wzx gene from a capsular polysaccharide gene cluster of *S. pneumoniae* CP1, CP2, CP3, CP4, CPS, CP6 (A and B), CP7 (A,B, C), CP8, CP9 (A, L,N, V), CP10 (A,B,C,F), CP11 (A, B,C,D,F), CP12(A,B,F), CP13, CP14 CP15(A,B,C,F), CP16(A,F), CP17(A,F), CP18(A,B, C,F), CP19(A,B,C,F), CP20,CP21, CP22(A,F), CP23(A,B, F), CP24(A,B,F), CP25(A,F), CP26, CP27,CP28(A,F), CP29, CP31, CP32(A,F), CP33(A,B,C,D,F), CP34, CP35 (A,B,C,D,F), CP36, CP37, CP38, CP39, CP40, CP41(A,F), CP42, CP43, CP44, CP45, CP46, CP47(A,F), or CP48. In a specific embodiment, the flippase introduced into the host cells described herein is the wzx gene from a capsular polysaccharide gene cluster of CP8, CP15A, CP16F, CP22F, CP23A, CP24F, CP31, CP33F, CP35B, or CP38.

Other flippases that can introduced into the host cells described herein are from *S. pneumoniae* described in Bentley S D, Aanensen D M, Mavroidi A, Saunders D, Rabbinowitsch E, Collins M, Donohoe K, Harris D, Murphy L, Quail M A et al: Genetic analysis of the capsular biosynthetic locus from all 90 pneumococcal serotypes. *PLoS genetics* 2006, 2(3):e31).

In certain embodiments, the flippase introduced into the host cells described herein is *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species.

Polymerases

In certain embodiments, a polymerase (Wzy) is introduced into a host cell described herein (i.e., the polymerase is heterologous to the host cell). Polymerases of various organisms (e.g., bacterial polymerases) are known in the art.

In a specific embodiment, a polymerase of a capsular polysaccharide biosynthetic pathway is introduced into a host cell described herein.

In another specific embodiment, a polymerase of a capsular polysaccharide biosynthetic pathway of *S. pneumoniae* is introduced into a host cell described herein.

In certain embodiments, the polymerase introduced into the host cells described herein is the wzy gene from a capsular polysaccharide gene cluster of *S. pneumoniae* CP1, CP2, CP4, CP5, CP6 (A and B), CP7 (A,B, C), CP8, CP9 (A, L,N, V), CP10 (A,B,C,F), CP11 (A, B,C,D,F), CP12(A,B, F), CP13, CP14 CP15(A,B,C,F), CP16(A,F), CP17(A,F), CP18(A,B,C,F), CP19(A,B,C,F), CP20,CP21, CP22(A,F), CP23(A,B,F), CP24(A,B,F), CP25(A,F), CP26, CP27,CP28 (A,F), CP29, CP31, CP32(A,F), CP33(A,B,C,D,F), CP34, CP35(A,B,C,D,F), CP36, CP37, CP38, CP39, CP40, CP41 (A,F), CP42, CP43, CP44, CP45, CP46, CP47(A,F), or CP48. In a specific embodiment, the polymerase introduced into the host cells described herein is the wzy gene from a capsular polysaccharide gene cluster of CP8, CP15A, CP16F, CP22F, CP23A, CP24F, CP31, CP33F, CP35B, or CP38.

Other polymerases that can introduced into the host cells described herein are from *S. pneumoniae* described in Bentley S D, Aanensen D M, Mavroidi A, Saunders D, Rabbinowitsch E, Collins M, Donohoe K, Harris D, Murphy L, Quail M A et al: Genetic analysis of the capsular biosynthetic locus from all 90 pneumococcal serotypes. PLoS genetics 2006, 2(3):e31).

In certain embodiments, the polymerase introduced into the host cells described herein is from *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species.

Enzymes that Modify Monosaccharides

In certain embodiments, enzymes that are capable of modifying monosaccharides are introduced into a host cell described herein (i.e., the enzymes that are capable of modifying monosaccharides are heterologous to the host cell). Such enzymes include, e.g., epimerases and racemases.

Epimerases and racemases of various organisms (e.g., bacterial epimerases and racemases) are known in the art. In certain embodiments, the epimerases and/or racemases introduced into the host cells described herein are from *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species.

In a specific embodiment, the epimerase Z3206 from *E. coli* O157 is introduced into the host cells described herein.

5.4 Bioconjugates

In certain embodiments, the host cells described herein can be used to produce bioconjugates comprising a hybrid oligosaccharide or polysaccharide described herein linked to a carrier protein. Methods of producing such bioconjugates using host cells are known in the art. See, e.g., WO 2003/074687 and WO 2006/119987, each of which are incorporated by reference herein in their entireties.

Bioconjugates, as described herein, have advantageous properties over chemically produced glycoconjugates, e.g., bioconjugates require less chemicals in manufacture and are more consistent in terms of the final product generated. Thus, bioconjugates are preferred over chemically produced glycoconjugates.

The host cells and methods described herein allow the production of novel hybrid saccharide structures in which the usual repeat unit of a particular saccharide is used for the majority of the final saccharide but the first repeat unit contains a hexose monosaccharide derivative at the reducing end. Such hybrid saccharides have the advantage of retaining the native structure for most of the saccharide so that the usual antigens are retained, but the presence of a hexose monosaccharide derivative at the reducing end of the assembled oligosaccharide or polysaccharide allows this to be a proper substrate for glycosyltransferases such as PglB, allowing increased efficiency in the attachment of such hybrid saccharides to a carrier protein to make a bioconjugate. The features set out below are suitable for either the hybrid oligosaccharides or polysaccharides of the invention or for methods of synethsising oligosaccharides or polysaccharides of the invention.

A further embodiment of the invention is a hybrid oligosaccharide or polysaccharide having a structure

wherein A is an oligosaccharide repeat unit containing at least 2, 3, 4, 5, 6, 7 or 8 monosaccharides, with a hexose monosaccharide derivative at the reducing end (indicated by arrow);

wherein B is an oligosaccharide repeat unit containing at least 2, 3, 4, 5, 6, 7 or 8 monosaccharides;

wherein A and B are different oligosaccharide repeat units; and wherein n is either at least 2, 3, 4, 5, 6, 7, 8, 9, 10, 11, 12, 13, 14, 15, 16, 17, 18, 19, 20, 30, 40, 50, 60, 70, 80, 100 or at least 200: or wherein n is at least 1, 2, 3, 4, 5, 6, 7, 8, 9, 10, 11, 12, 13, 14, 15, 16, 17, 18, 19, 20, 30, 40, 50, 60, 70, 80, 100 or at least 200.

In an embodiment, A is an oligosaccharide containing no more than 20, 15, 12, 10, 9, or 8 monosaccharides. In an embodiment, B is an oligosaccharide containing no more than 20, 15, 12, 10, 9, or 8 monosaccharides. In an embodiment, A and B are oligosaccharides containing no more than 20, 15, 12, 10, 9, or 8 monosaccharides. In an embodiment n is no more than 500, 400, 300, 200, 100, 90, 80, 70, 60, 50, 40, 30, 20, 10 or 5.

In an embodiment, A is an oligosaccharide repeat unit containing at least 3 monosaccharides and B is an oligosaccharide repeat unit containing at least 3 monosaccharides. In an embodiment, A is an oligosaccharide repeat unit containing at least 3 monosaccharides and B is an oligosaccharide repeat unit containing at least 3 monosaccharides and n is at least 5. In an embodiment, A is an oligosaccharide repeat unit containing at least 3 monosaccharides and B is an oligosaccharide repeat unit containing at least 3 monosaccharides and n is at least 20.

In an embodiment, A is an oligosaccharide repeat unit containing at least 4 monosaccharides and B is an oligosaccharide repeat unit containing at least 4 monosaccharides. In an embodiment, A is an oligosaccharide repeat unit containing at least 4 monosaccharides and B is an oligosaccharide repeat unit containing at least 4 monosaccharides and n is at least 5. In an embodiment, A is an oligosaccharide repeat unit containing at least 4 monosaccharides and B is an oligosaccharide repeat unit containing at least 4 monosaccharides and n is at least 20.

In an embodiment, A is an oligosaccharide repeat unit containing at least 5 monosaccharides and B is an oligosaccharide repeat unit containing at least 5 monosaccharides. In an embodiment, A is an oligosaccharide repeat unit containing at least 5 monosaccharides and B is an oligosaccharide repeat unit containing at least 5 monosaccharides and n is at least 5. In an embodiment, A is an oligosaccharide repeat unit containing at least 5 monosaccharides and B is an oligosaccharide repeat unit containing at least 5 monosaccharides and n is at least 20.

In an embodiment, A is an oligosaccharide repeat unit containing at least 6 monosaccharides and B is an oligosaccharide repeat unit containing at least 6 monosaccharides. In an embodiment, A is an oligosaccharide repeat unit containing at least 6 monosaccharides and B is an oligosaccharide repeat unit containing at least 6 monosaccharides and n is at least 5. In an embodiment, A is an oligosaccharide repeat unit containing at least 6 monosaccharides and B is an oligosaccharide repeat unit containing at least 6 monosaccharides and n is at least 20.

In an embodiment, A is an oligosaccharide repeat unit containing 2-8 monosaccharides and B is an oligosaccharide repeat unit containing 2-8 monosaccharides. In an embodiment, A is an oligosaccharide repeat unit containing 2-8 monosaccharides and B is an oligosaccharide repeat unit containing 2-8 monosaccharides and n is at least 5 and no more than 500. In an embodiment, A is an oligosaccharide repeat unit containing 2-8 monosaccharides and B is an oligosaccharide repeat unit containing 2-8 monosaccharides and n is at least 20 and no more than 100.

In an embodiment, A is an oligosaccharide repeat unit containing 2-10 monosaccharides and B is an oligosaccharide repeat unit containing 2-10 monosaccharides. In an embodiment, A is an oligosaccharide repeat unit containing 2-10 monosaccharides and B is an oligosaccharide repeat unit containing 2-10 monosaccharides and n is at least 5 and no more than 500. In an embodiment, A is an oligosaccharide repeat unit containing 2-10 monosaccharides and B is an oligosaccharide repeat unit containing 2-10 monosaccharides and n is at least 20 and no more than 100.

In an embodiment of the hybrid oligosaccharide or polysaccharide, the B oligosaccharide repeat contains a hexose monosaccharide at the reducing end of the repeat. In an embodiment of the hybrid oligosaccharide or polysaccharide, the hexose monosaccharide at the reducing end of the repeat is selected from the group consisting of glucose, galactose, rhamnose, arabinotol, fucose and mannose; suitably the group consists of glucose and galactose.

In an embodiment of the hybrid oligosaccharide or polysaccharide, the oligosaccharide repeat unit of A and the oligosaccharide repeat unit of B differ only by containing a different monosaccharide at the reducing end of the repeat.

In an embodiment of the hybrid oligosaccharide or polysaccharide, the oligosaccharide repeat unit of A is the repeat unit of the capsular saccharide of a Gram positive bacterial capsular saccharide, for example a Group A streptococcus capsular saccharide, a Group B streptococcus capsular saccharide, a *Streptococcus pneumoniae* capsular saccharide, an Enterococcal capsular saccharide or a *Staphylococcus aureus* capsular saccharide; for example the repeat unit of the capsular saccharide of a *Streptococcus pneumoniae* serotype 1, 2, 3, 4, 5, 6A, 6B, 7A, 7B, 7C, 8, 9A, 9L, 9N, 9V, 10A, 10B, 10C, 10F, 11A, 11B, 11C, 11D, 11F, 12A, 12B, 12F, 13, 14, 15A, 15B, 15C, 15F, 16A, 16F, 17A, 17F, 18A, 18B, 18C, 18F, 19A, 19B, 19C, 19F, 20, 21, 22A, 22F, 23A, 23B, 23F, 24A, 24B, 24F, 25A, 25F, 26, 27, 28A, 28F, 29, 31, 32A, 32F, 33A, 33B, 33C, 33D, 33F, 34, 35A, 35B, 35C, 35D, 35F, 36, 37, 38, 39, 40, 41A, 41F, 42, 43, 44, 45, 46, 47A, 47F or 48; suitably of serotypes 8, 12F, 14, 15A, 16F, 22F, 23A, 24F, 31, 33F, 35B or 38; or the repeat unit of the capsular saccharide of a *Streptococcus pneumoniae* serotype 2, 3, 6A, 6B, 7A, 7B, 7C, 8, 9A, 9L, 9N, 9V, 10A, 10B, 10C, 10F, 11A, 11B, 11C, 11D, 11F, 13, 14, 15A, 15B, 15C, 15F, 16A, 16F, 17A, 17F, 18A, 18B, 18C, 18F, 19A, 19B, 19C, 19F, 20, 21, 22A, 22F, 23A, 23B, 23F, 24A, 24B, 24F, 25A, 25F, 26, 27, 28A, 28F, 29, 31, 32A, 32F, 33A, 33B, 33C, 33D, 33F, 34, 35A, 35B, 35C, 35D, 35F, 36, 37, 38, 39, 40, 41A, 41F, 42, 43, 44, 45, 46, 47A, 47F or 48.

In an embodiment, of the hybrid oligosaccharide or polysaccharide, the oligosaccharide repeat unit of A is the repeat unit of the capsular saccharide of a Group B streptococcus capsular saccharide, selected from serotype Ia, Ib, II, III, IV, V, VI, VII or VIII, In an embodiment of the hybrid oligosaccharide or polysaccharide, the oligosaccharide repeat unit of A is the repeat unit of a *Staphylococcus aureus* capsular saccharide of serotype 5 or serotype 8, or of a *Enterococcus faecalis* serotype A, B, C or D.

A further aspect of the invention is a bioconjugate comprising a carrier protein as described herein, linked to the hybrid oligosaccharide or polysaccharides described above.

A further aspect of the invention is a bioconjugate comprising a carrier protein N-linked to a hybrid oligosaccharide or polysaccharide, wherein said hydrid oligosaccharide or polysaccharide is identical to a donor oligosaccharide or polysaccharide, with the exception of the fact that the hybrid oligosaccharide or polysaccharide comprises a hexose monosaccharide derivative at the reducing end of the first repeat unit in addition to comprising all of the monosaccharides of the donor oligosaccharide or polysaccharide. In other words, a bioconjugate comprising a carrier protein containing a Asn-X-Ser/Thr consensus sequence, the asparagine residue of which is linked to a hybrid oligosaccharide or polysaccharide, wherein said hybrid oligosaccharide or polysaccharide contains at least 2, 3, 4, 5, 6, 7, 8, 9, 10, 20, 30, 40 or 50 saccharide repeat units of a donor oligosaccharide or polysaccharide and a further repeat unit N-linked to the carrier protein in which a hexose monosaccharide derivative is at the reducing end of said further repeat unit.

In an embodiment, the hexose monosaccharide derivative is any monosaccharide in which C-2 position is modified with an acetamido group. Suitable hexose monosaccharide derivatives include N-acetylglucosamine (GlcNAc), N-acetylgalactoseamine (GalNAc), HexNAc, deoxy HexNAc, 2,4-Diacetamido-2,4,6-trideoxyhexose (DATDH), N-acetylfucoseamine (FucNAc), or N-acetylquinovosamine (QuiNAc). A suitable hexose monosaccharide derivative is N-acetylglucosamine (GlcNAc).

In an embodiment, the hybrid oligosaccharide or polysaccharide is identical to a Gram positive bacterial capsular saccharide, with the exception of the fact that the hybrid oligosaccharide or polysaccharide comprises a hexose monosaccharide derivative at the reducing end of the first repeat unit in place of the hexose monosaccharide normally present at the reducing end of the first repeat of said Gram positive bacterial capsular saccharide.

In an embodiment the Gram positive bacterial capsular saccharide is a Group A streptococcus capsular saccharide, a Group B streptococcus capsular saccharide, a *Streptococcus pneumoniae* capsular saccharide, Enterococcal capsular saccharide or a *Staphylococcus aureus* capsular saccharide. The term saccharide includes both oligosaccharide and polysaccharide.

In an embodiment, the Gram positive bacterial capsular saccharide is a *Streptococcus pneumoniae* serotype 1, 2, 3, 4, 5, 6A, 6B, 7A, 7B, 7C, 8, 9A, 9L, 9N, 9V, 10A, 10B, 10C, 10F, 11A, 11B, 11C, 11D, 11F, 12A, 12B, 12F, 13, 14, 15A, 15B, 15C, 15F, 16A, 16F, 17A, 17F, 18A, 18B, 18C, 18F, 19A, 19B, 19C, 19F, 20, 21, 22A, 22F, 23A, 23B, 23F, 24A, 24B, 24F, 25A, 25F, 26, 27, 28A, 28F, 29, 31, 32A, 32F, 33A, 33B, 33C, 33D, 33F, 34, 35A, 35B, 35C, 35D, 35F, 36, 37, 38, 39, 40, 41A, 41F, 42, 43, 44, 45, 46, 47A, 47F or 48 capsular saccharide; or the repeat unit of the capsular saccharide of a *Streptococcus pneumoniae* serotype 2, 3, 6A, 6B, 7A, 7B, 7C, 8, 9A, 9L, 9N, 9V, 10A, 10B, 10C, 10F, 11A, 11B, 11C, 11D, 11F, 13, 14, 15A, 15B, 15C, 15F, 16A, 16F, 17A, 17F, 18A, 18B, 18C, 18F, 19A, 19B, 19C, 19F, 20, 21, 22A, 22F, 23A, 23B, 23F, 24A, 24B, 24F, 25A, 25F, 26, 27, 28A, 28F, 29, 31, 32A, 32F, 33A, 33B, 33C, 33D, 33F, 34, 35A, 35B, 35C, 35D, 35F, 36, 37, 38, 39, 40, 41A, 41F, 42, 43, 44, 45, 46, 47A, 47F or 48; or suitably a *Streptococcus pneumoniae* serotype 8, 12F, 14, 15A, 16F, 22F, 23A, 24F, 31, 33F, 35B or 38 capsular saccharide.

In an embodiment, the Gram positive bacterial capsular saccharide is a *S. aureus* serotype 5 or 8 capsular saccharide.

In an embodiment, the Gram positive bacterial capsular saccharide is a *Streptococcus agalactiae* (Goup B Streptococcus) serotype Ia, Ib, II, III, IV, V, VI, VII or VIII capsular saccharide.

In an embodiment, the Gram positive bacterial capsular saccharide is a *Enterococcus faecalis* serotype A, B, C or D capsular saccharide.

In an embodiment, the carrier protein is detoxified Exotoxin A of *P. aeruginosa* (EPA), CRM197, maltose binding protein (MBP), Diphtheria toxoid, Tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin and detoxified variants thereof, *Streptococcus pneumoniae* PhtD protein, *C. jejuni* AcrA, a *C. jejuni* natural glycoprotein, PcrV (aka LcrV,EspA, SseB), PopB (YopB, YopD, FliC), or OprF, OprI. In an embodiment, each carrier protein contains at least 1, 2, 3, 4, 5 or 6 glycosylation consensus sequences (e.g. Asn-X-Ser/Thr, more particularly Asp/Glu-X-Asn-Z-Ser/Thr, wherein X and Z can be any natural amino acid except Pro.

5.5 Compositions

Compositions Comprising Host Cells

In one aspect, provided herein are compositions comprising the host cells described herein. Such compositions can be used in methods for generating the bioconjugates described herein, e.g., the compositions can be cultured under conditions suitable for the production of proteins. Subsequently, bioconjugates can be isolated from said compositions using methods known in the art.

The compositions comprising the host cells provided herein can comprise additional components suitable for maintenance and survival of the host cells described herein, and can additionally comprise additional components required or beneficial to the production of proteins by the host cells, e.g., inducers for inducible promoters, such as arabinose, IPTG.

Compositions Comprising Bioconjugates

In another aspect, provided herein are compositions (e.g., pharmaceutical compositions) comprising one or more of the bioconjugates described herein. In a specific embodiment, a composition provided herein comprises one or more of the bioconjugates described herein. The compositions described herein are useful in the treatment and prevention of bacterial infection of subjects (e.g., human subjects) with bacteria known to have antigenic oligosaccharides and/or polysaccharides.

In a specific embodiment, provided herein is a composition comprising a bioconjugate, wherein said bioconjugate comprises a hybrid *S. pneumoniae* capsular polysaccharide. In another specific embodiment, provided herein is a composition comprising two bioconjugates, wherein said bioconjugates each comprise a different hybrid *S. pneumoniae* capsular polysaccharide (i.e., a bivalent composition). In another specific embodiment, provided herein is a composition comprising three bioconjugates, wherein said bioconjugates each comprise a different hybrid *S. pneumoniae* capsular polysaccharide (i.e., a trivalent composition). In a specific embodiment, said *S. pneumoniae* capsular polysaccharide is CP1, CP2, CP3, CP4, CP5, CP6 (A, B), CP7 (A, B, C), CP8, CP9 (A, L, N, V), CP10 (A, B, C, F), CP11 (A, B, C, D, F), CP12(A, B, F), CP13, CP14, CP15 (A, B, C, F), CP16 (A, F), CP17 (A, F), CP18 (A, B, C, F), CP19 (A, B, C, F), CP20, CP21, CP22 (A, F), CP23 (A, B, F), CP24 (A, B, F), CP25 (A, F), CP 26, CP27, CP28 (A, F), CP29, CP31, CP32 (A, F), CP33 (A, B, C, D, F), CP34, CP35 (A, B, C, D, F), CP36, CP37, CP38, CP39, CP40, CP41 (A, F), CP42, CP43, CP44, CP45, CP46, CP47 (A, F), or CP48. In a specific embodiment, said trivalent composition comprises (i) a bioconjugate comprising a hybrid *S. pneumoniae* CP1 capsular polysaccharide; (ii) (i) a bioconjugate comprising a hybrid *S. pneumoniae* CP4 capsular polysaccharide; and (iii) (i) a bioconjugate comprising a hybrid *S. pneumoniae* CP14 capsular polysaccharide.

In a specific embodiment, provided herein is a composition comprising a bioconjugate, wherein said bioconjugate comprises a hybrid *Staphylococcus aureus* capsular polysaccharide, e.g., *S. aureus* capsular polysaccharide is CP5 or CP8.

In a specific embodiment, provided herein is a composition comprising a bioconjugate, wherein said bioconjugate comprises a hybrid *Streptococcus agalactiae* (GBS) capsular polysaccharide, e.g., *S. agalactiae* (group B, GBS) CPIa, CPIb, CPII, CPIII, CPIV, CPV, CPVI, CPVII, or CPVIII.

In a specific embodiment, provided herein is a composition comprising a bioconjugate, wherein said bioconjugate comprises a hybrid *Enterococcus faecalis* capsular polysaccharide, e.g., *Enterococcus faecalis* capsular polysaccharide CPA, CPB, CPC, or CPD.

In certain embodiments, in addition to comprising a bioconjugate described herein (the compositions (e.g., pharmaceutical compositions) described herein comprise a pharmaceutically acceptable carrier. As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier," as used herein in the context of a pharmaceutically acceptable carrier, refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Examples of suitable pharmaceutical carriers are described in "Remington's Pharmaceutical Sciences" by E. W. Martin.

The compositions comprising the bioconjugates described herein may comprise any additional components suitable for use in pharmaceutical administration. In specific embodiments, the compositions described herein are monovalent formulations. In other embodiments, the compositions described herein are multivalent formulations, e.g., bivalent, trivalent, and tetravalent formulations. For example, a multivalent formulation comprises more than one bioconjugate described herein.

In certain embodiments, the compositions described herein additionally comprise a preservative, e.g., the mercury derivative thimerosal. In a specific embodiment, the pharmaceutical compositions described herein comprise 0.001% to 0.01% thimerosal. In other embodiments, the pharmaceutical compositions described herein do not comprise a preservative.

In certain embodiments, the compositions described herein (e.g., the immunogenic compositions) comprise, or are administered in combination with, an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a bioconjugate, but when the compound is administered alone does not generate an immune response to the bioconjugate. In some embodiments, the adjuvant generates an immune response to the poly bioconjugate peptide and does not produce an allergy or other adverse reaction. Adjuvants can enhance an immune response by several mechanisms including, e.g., lymphocyte recruitment, stimulation of B and/or T cells, and stimulation of macrophages.

Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see United Kingdom Patent GB2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, NY, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998).

In certain embodiments, the compositions described herein are formulated to be suitable for the intended route of administration to a subject. For example, the compositions described herein may be formulated to be suitable for subcutaneous, parenteral, oral, intradermal, transdermal, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration.

In certain embodiments, the compositions described herein additionally comprise one or more buffers, e.g., phosphate buffer and sucrose phosphate glutamate buffer. In other embodiments, the compositions described herein do not comprise buffers.

In certain embodiments, the compositions described herein additionally comprise one or more salts, e.g., sodium chloride, calcium chloride, sodium phosphate, monosodium glutamate, and aluminum salts (e.g., aluminum hydroxide, aluminum phosphate, alum (potassium aluminum sulfate), or a mixture of such aluminum salts). In other embodiments, the compositions described herein do not comprise salts.

The compositions described herein can be included in a container, pack, or dispenser together with instructions for administration.

The compositions described herein can be stored before use, e.g., the compositions can be stored frozen (e.g., at about −20° C. or at about −70° C.); stored in refrigerated conditions (e.g., at about 4° C.); or stored at room temperature.

5.6 Prophylactic and Therapeutic Uses

Provided herein are methods of treating and/or preventing bacterial infections of a subject comprising administering to the subject a bioconjugate described herein or a composition described herein. In a specific embodiment, the compositions described herein are used in the prevention of infection of a subject (e.g., human subjects) by a bacterium. Bacteria infections that can be treated and/or prevented using the bioconjugates and/or compositions provided herein include those caused by *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species. In a specific embodiment, a bioconjugate described herein or a composition described herein is used to treat or prevent an infection by *Streptococcus* species.

Also provided herein are methods of inducing an immune response in a subject against a bacterium, comprising administering to the subject a bioconjugate described herein (or a composition described herein. In one embodiment, said subject has bacterial infection at the time of administration. In another embodiment, said subject does not have a bacterial infection at the time of administration. The bioconjugates and/or compositions provided herein can be used to induce an immune response against *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species. In a specific embodiment, a bioconjugate described herein or a composition described herein is used to induce an immune response against *Streptococcus* species.

Also provided herein are methods of inducing the production of opsonophagocytic antibodies in a subject against a bacterium, comprising administering to the subject a bioconjugate described herein (or a composition described herein. In one embodiment, said subject has bacterial infection at the time of administration. In another embodiment, said subject does not have a bacterial infection at the time of administration. The bioconjugates and/or compositions provided herein can be used to induce the production of opsonophagocytic antibodies against *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species. In a specific embodiment, a bioconjugate described herein or a composition described herein is used to induce the production of opsonophagocytic antibodies against *Streptococcus* species.

Combination Therapies

In certain embodiments, a bioconjugate described herein or a composition described herein is administered to a subject in combination with one or more other therapies (e.g., antibacterial or immunomodulatory therapies). The one or more other therapies may be beneficial in the treatment or prevention of a bacterial infection or may ameliorate a symptom or condition associated with a bacterial infection. In some embodiments, the one or more other therapies are pain relievers or anti-fever medications. In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part.

Any anti-bacterial agents known to one of skill in the art may be used in combination with a bioconjugate described herein or a composition described herein. Non-limiting examples of anti-bacterial agents include Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazone-sulbactam, Cefotaxime, Cefoxitin, Cefpirome, Cefpodoxime, Cefpodoxime-clavulanic acid, Cefpodoxime-sulbactam, Cefprozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Meziocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, and Voriconazole.

In certain embodiments, a combination therapy comprises administration of two or more bioconjugates described herein (see Section 5.4) and/or compositions described herein.

Dosage and Frequency of Administration

The amount of a bioconjugate described herein or a composition described herein which will be effective in the treatment and/or prevention of a bacterial infection will depend on the nature of the disease, and can be determined by standard clinical techniques. Administration of the bioconjugate and/or composition can be done via various routes known to the clinician, for instance subcutaneous, parenteral, intravenous, intramuscular, topical, oral, intradermal, transdermal, intranasal, etc. In one embodiment, administration is via intramuscular injection.

The precise dosage to be employed in the formulation will also depend on the route of administration, and the seriousness of the infection, and should be decided according to the judgment of the practitioner and each subject's circumstances. For example, effective dosages may also vary depending upon means of administration, target site, physiological state of the patient (including age, body weight, health), whether the patient is human or an animal, other medications administered, and whether treatment is prophylactic or therapeutic. Treatment dosages are optimally titrated to optimize safety and efficacy.

In certain embodiments, an in vitro assay is employed to help identify optimal dosage ranges. See Section 5.7. Effective doses may be extrapolated from dosage response curves derived from in vitro or animal model test systems.

In certain embodiments, exemplary dosages for bioconjugate based vaccines (e.g., compositions comprising bioconjugates) range from about 0.1 µg to 400 µg of carbohydrate per dose. In other embodiments, exemplary dosages for glycoconjugate based vaccines (e.g., compositions comprising bioconjugates) range from about 0.1 µg to 4000 µg of protein(s) per dose. In certain embodiments, an exemplary dosage for a glycoconjugate based vaccine (e.g., a composition comprising bioconjugates) comprises 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 µg of carbohydrate(s) per dose. In certain embodiments, an exemplary dosage for a glycoconjugate based vaccine (e.g., a composition comprising bioconjugates) comprises 50, 55, 60, 65, 70, 75, 80, 85, 90, 95, or 100 µg of protein(s) per dose. In certain exemplary embodiments, a dosage for administration to a human corresponds to 0.5 ml containing about 1-10, e.g. about 2-6, e.g. about 4 µg of polysaccharide for each of the glycoconjugates included.

In certain embodiments, a bioconjugate described herein or a composition described herein is administered to a subject once as a single dose. In certain embodiments, a bioconjugate described herein or a composition described herein is administered to a subject as a single dose followed by a second dose 3 to 6 weeks later. In accordance with these embodiments, booster inoculations may be administered to the subject at 6 to 12 month intervals following the second inoculation. In certain embodiments, the booster inoculations may utilize a different bioconjugate or composition. In some embodiments, the administration of the same bioconjugate or composition may be repeated and the administrations may be separated by at least 1 day, 2 days, 3 days, 5 days, 7 days, 10 days, 15 days, 30 days, 45 days, 2 months, 75 days, 3 months, or at least 6 months. In certain embodiments, a bioconjugate described herein or a composition described herein is administered to a subject as a single dose once per year.

In certain embodiments, a bioconjugate described herein or a composition described herein is administered to a subject as 2, 3, 4, 5 or more doses 2 weeks, 3 weeks, 4 weeks, 5 weeks or 6 weeks apart. In some embodiments, 2, 3, 4, 5 or more doses of a bioconjugate described herein or a composition described herein are administered to a subject 2, 3, 4, 5 or 6 weeks apart at a dosage of 0.1 µg to 0.5 mg, 0.1 µg to 0.4 mg, 0.1 µg to 0.3 mg, 0.1 µg to 0.2 mg, or 0.1 µg to 0.1 mg carbohydrate content. In certain embodiments, the bioconjugate or composition administered is the same each time. In certain embodiments, the bioconjugate or composition administered is different each time.

5.7 Assays

Assay for Assessing Ability of Bioconjugates to Induce an Immune Response

The ability of the bioconjugates/compositions described herein to generate an immune response in a subject can be assessed using any approach known to those of skill in the art or described herein. In some embodiments, the ability of a bioconjugate to generate an immune response in a subject can be assessed by immunizing a subject (e.g., a mouse) or set of subjects with a bioconjugate described herein and immunizing an additional subject (e.g., a mouse) or set of subjects with a control (PBS). The subjects or set of subjects can subsequently be challenged with a bacterium of interest and the ability of the bacterium of interest to cause disease in the subjects or set of subjects can be determined. Those skilled in the art will recognize that if the subject or set of subjects immunized with the control suffer(s) from disease subsequent to challenge with the bacterium of interest but the subject or set of subjects immunized with a bioconjugate(s) or composition thereof described herein suffer less from or do not suffer from disease, then the bioconjugate is able to generate an immune response in a subject. The ability of a bioconjugate(s) or composition thereof described herein to induce antiserum that cross-reacts with an O antigen from bacterium of interest can be tested by, e.g., an immunoassay, such as an ELISA.

In Vitro Bactericidal Assays

The ability of the bioconjugates described herein to generate an immune response in a subject can be assessed using a serum bactericidal assay (SBA) or opsonophagocytotic killing assay (OPK), which represents an established and accepted method that has been used to obtain approval of glycoconjugate-based vaccines. Such assays are well-known in the art and, briefly, comprise the steps of generating and isolating antibodies against a target of by administering to a subject (e.g., a mouse) a compound that elicits such antibodies. Subsequently, the bactericidal capacity of the antibodies can be assessed by, e.g., culturing the bacteria in question in the presence of said antibodies and complement and—depending on the assay—neutrophilic cells and assaying the ability of the antibodies to kill and/or neutralize the bacteria, e.g., using standard microbiological approaches.

EXAMPLES

Example 1: Synthesis of CP14 Bioconjugates in *E. coli*

This example describes production of bioconjugates comprising a carrier protein linked to a hybrid polysaccharide derived from the donor polysaccharide *S. pneumoniae* CP14. The hybrid polysaccharide comprises a hexose monosaccharide derivative at the reducing end of the first repeat unit, instead of a hexose monosaccharide, which is present in wild-type *S. pneumoniae* CP14. Applicant has identified that flippases and polymerases comprise relaxed specificity, thus allowing for the engineering of the hybrid polysaccharide in a heterologous host cell. The presence of the hexose monosaccharide derivative in place of the hexose monosaccharide allows for the hybrid polysaccharide to be transferred to a carrier protein by an oligosaccharyltransferase (PglB) to produce a bioconjugate in a host cell (*E. coli*). The approach described in this example can easily be adapted to any oligosaccharides or polysaccharides that comprise a hexose monosaccharide at the reducing end of the first repeat unit, thus allowing such oligosaccharides or polysaccharides to be linked to carrier proteins (to form bioconjugates) in a host cell.

Figure 1:
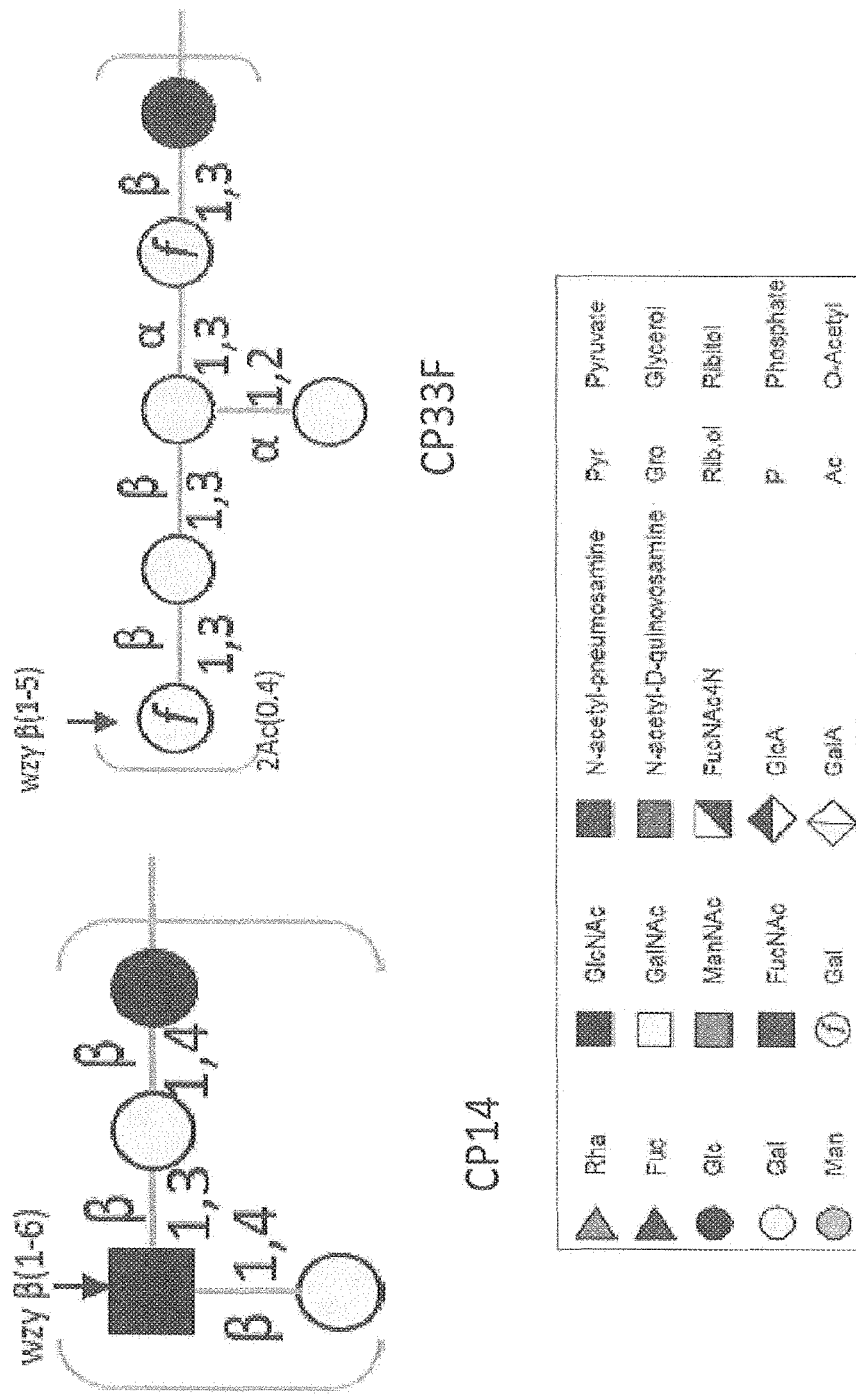
FIG. 1 depicts the structure of the repeating units of S. pneumoniae capsular polysaccharide (CP) 14 and CP33F.
Figure 2:
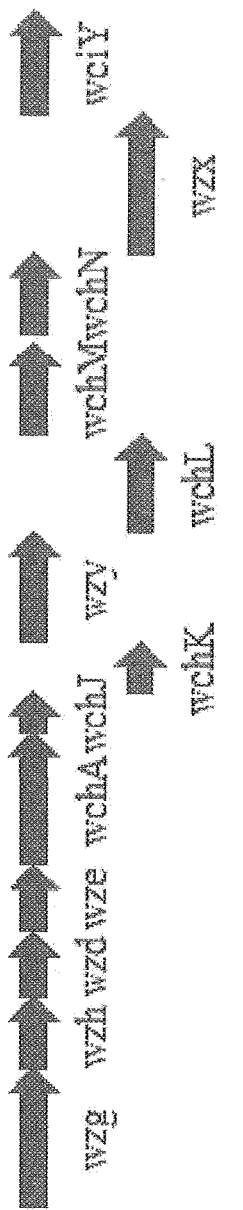
FIG. 2 depicts a schematic diagram of the gene organization of the S. pneumoniae CP14 wild type cluster and the putative function of each gene.
Figure 3:
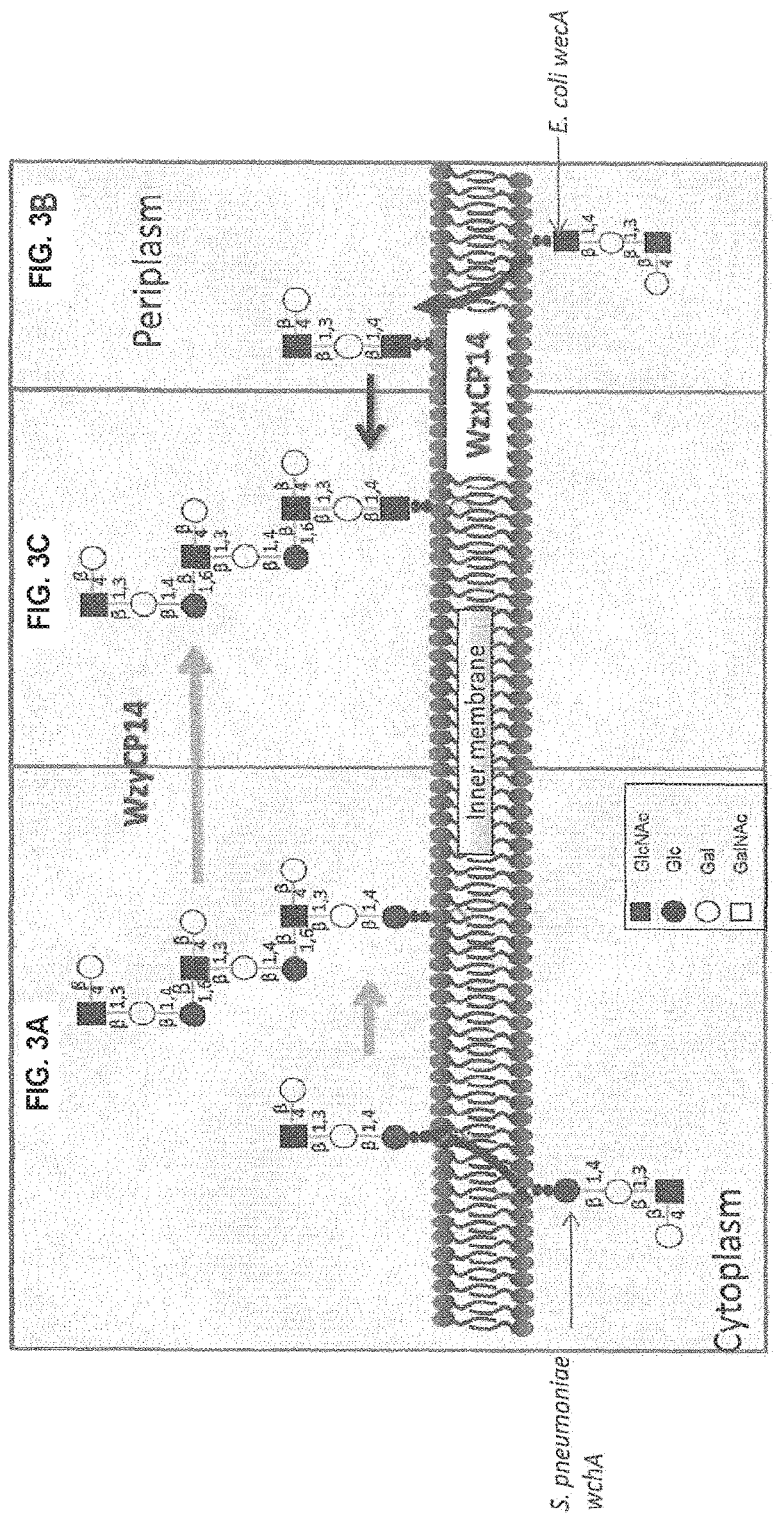
FIG. 3 depicts a a synthetic glycosylation pathway for production of a modified S. pneumoniae CP14 polymer that can efficiently be transferred by an oligosaccharyltransferase to a protein carrier. 3A: the wild type biosynthetic pathway of S. pneumoniae CP14. 3B: biosynthesis of an engineered subunit of CP14 that differs at its reducing end monosaccharide compared to the wild type subunit. 3C: polymerization of the wild type CP14 polysaccharide and assembly of wild type polysaccharide on a single engineered subunit.

The repeat unit structure of *S. pneumoniae* CP14 is shown in FIG. 1 and the CP14 gene cluster is depicted in FIG. 2 and. The repeat unit of CP14 is composed of b-D-Gal-1,4-b-D-GlcNAc-1,3-b-D-Gal-1,4-b-D-Glc-. FIG. 3 illustrates the principle of the glycoenginnering approach used in this Example, which produces hybrid CP14 that only differs from wild type CP14 in its reducing end monosaccharide.

The portion of the CP14 gene cluster containing the stretch from wchA to wciY (see FIG. 2) was cloned into the pDOC-C plasmid (Lee D J, Bingle L E, Heurlier K, Pallen M J, Penn C W, Busby S J, Hobman J L: Gene doctoring: a method for recombineering in laboratory and pathogenic *Escherichia coli* strains. BMC Microbiol 2009, 9:252) and subsequently integrated into *E. coli* strain W3310 (comprising a deletion of the waaL gene) in place of the colanic acid cluster, following the methods described in International Patent Application No. WO2014/072405, which is incorporated by reference herein in its entirety. The resultant strain, *E. coli* W3110 colanic acid::CP14 ΔwaaL, was used in certain experiments, as described below.

To produce the glycoengineered CP14 subunit (a repeat unit comprising a hexose monosaccharide derivative at the reducing end), a galactosyltransferase (WfeD) from *Shigella boyedii* was used. It has been reported that WfeD transfers Gal from UDP-Gal to -GlcNAc-P-P-Undecaprenyl. First, GlcNAc is assembled on UndP from UDP-GlcNAc by WecA (which exists in all Gram-negative bacteria that synthesize ECA and Gram-positive bacteria that make Teichoic acid) (Annu Rev Microbiol. 2013; 67:313-36; Glycobiology. 2011 February; 21(2):138-51.), to make a β (1,4) linkage (J Bacteriol. 2011 January; 193(2):449-59). The product of this reaction was the disaccharide Gal-GlcNAc-P-P-Undecaprenyl. Thereafter, WchL and WchM from the *S. pneumoniae* CP14 cluster, which add GlcNAc and Gal to β-D-Gal-1,4-β-D-GlcNAc-PP-Und, respectively, were used to produce a CP14 engineered subunit, β-D-Gal-1,4-β-D-GlcNAc-1,3-β-D-Gal-1,4-β-D-GlcNAc-PP-Und (FIG. 4D). The schematic of the synthetic plasmid produced based on the combination of above genes (pGVX1190) is shown in FIG. 4A.

The CP14 engineered subunit described above was produced in the cytoplasm of the *E. coli* host cell. However, for polysaccharide formation, the subunit needed to be translocated into the periplasm where the wild type polysaccharide (CP14) could be assembled on it. To test if the flippase of the CP14 biosynthetic pathway was able to translocate the engineered submit, the CP14 wzx gene (flippase) was added to plasmid pGVX1190 to generate pGVX1366 (FIG. 4B). Both plasmids were transformed into *E. coli* SΦ874 cells that lack the O antigen flippase. Silver staining of proteinase K digested samples from *E. coli* SΦ874 transformed with the plasmids showed a band corresponding to the CP14 engineered subunit assembled on the lipid A core only when the flippase of CP14 (Wzx) was present (FIG. 4C). This result demonstrated that the CP14 engineered subunit could be produced and that the flippase of CP14 (Wzx) was able to translocate it into the periplasm where the O antigen ligase of *E. coli*, WaaL, transfers it to a lipid A core.

Figure 5A:
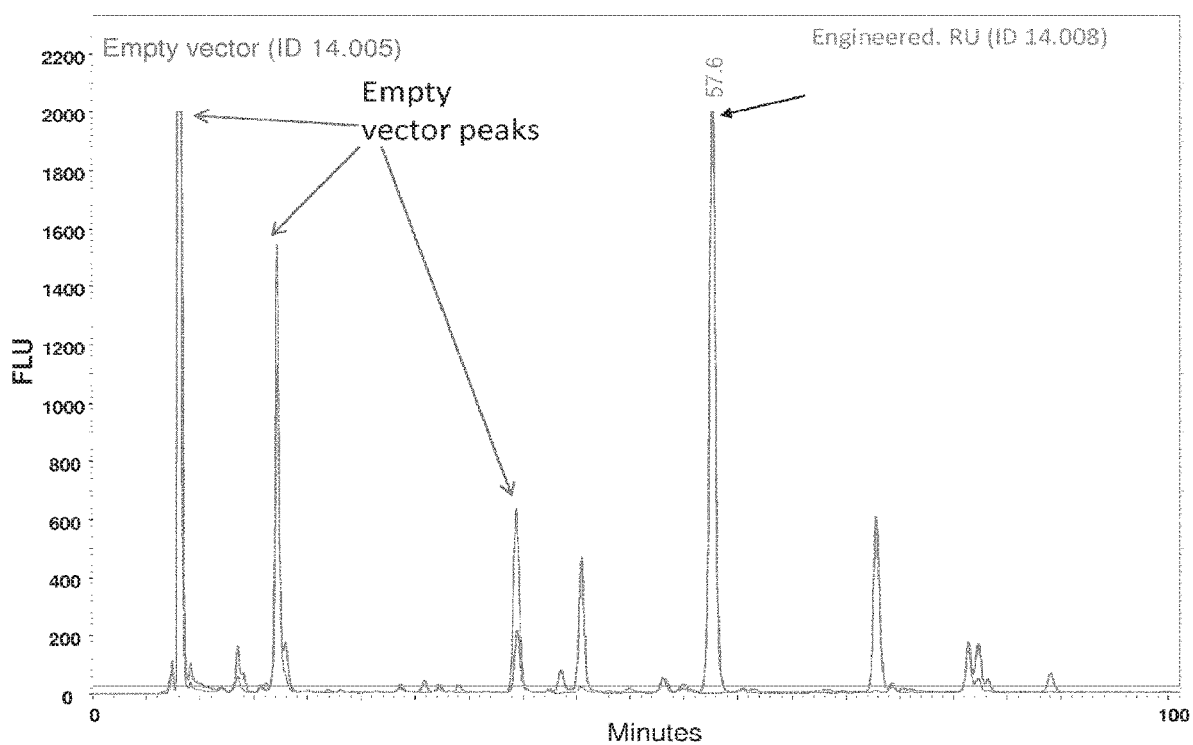
FIG. 5 describes analyses of an engineered CP14 subunit that was produced in E. coli. Lipid linked oligosaccharides (LLO) were extracted and labeled by 2AB and subjected to HPLC coupled with a florescence detector. 5A: HPLC chromatogram of CP14 engineered subunit LLO extracted from E. coli SΦ874 (ΔwaaL) transformed with plasmid pGVX1366 or its corresponding empty vector (peaks of empty vector are indicated). Arrow (at 57.6) indicates the peak corresponding to CP14 engineered subunit which was subjected to mass spectroscopy analysis. 5B, MS/MS analysis of the 57.5 min peak. Ion fragments matched with the expected structure of the engineered CP14 subunit.
Figure 5B:
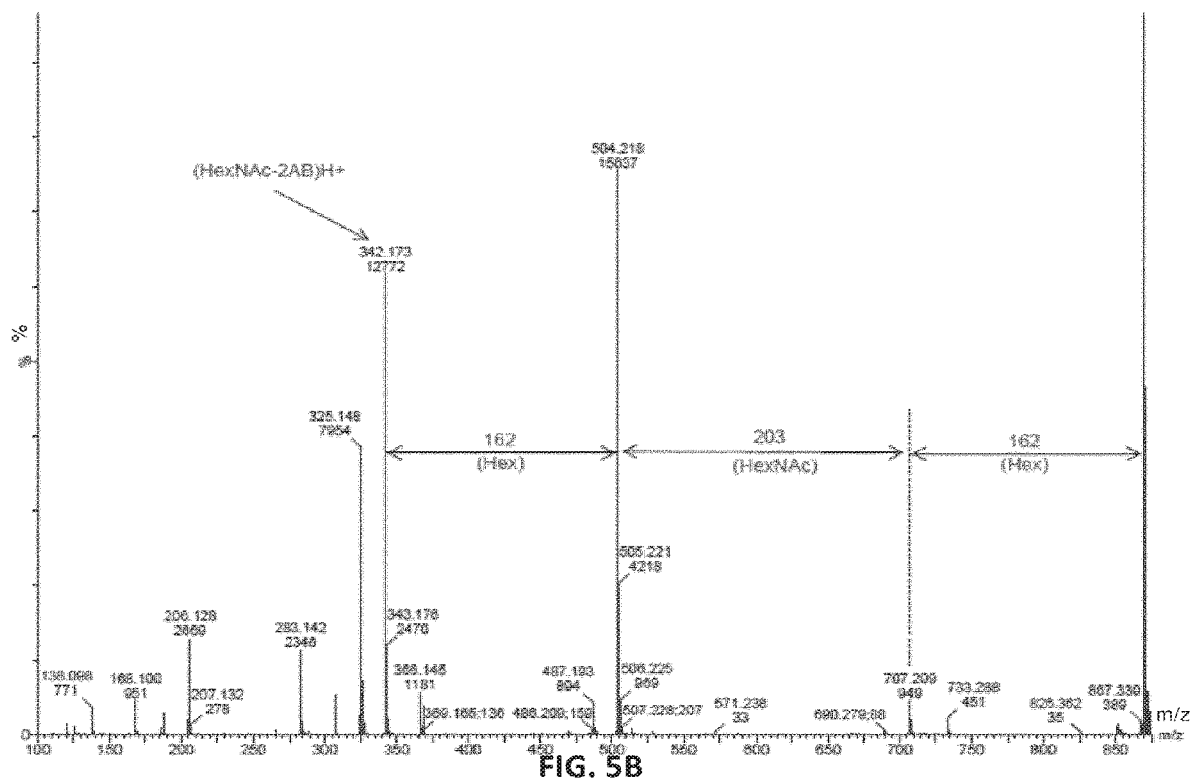

To confirm the structure of the CP14 engineered subunit, pGVX1366 or its corresponding empty vector, was transformed into *E. coli* SΦ874 ΔwaaL, cells were grown, harvested after induction, and LLO was purified and labeled by 2AB and subjected to HPLC (FIG. 5). A unique peak eluting at 57 minutes was collected and subjected to mass spectroscopy analysis (FIG. 5A). It was demonstrated that the monosaccharide composition of the oligosaccharide matched the proposed CP14 engineered subunit (FIG. 5B).

Figure 6A:
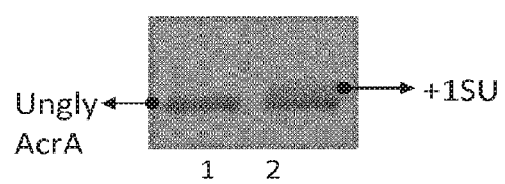
FIG. 6 shows that the engineered CP14 subunit is a substrate for the C. jejuni oligosaccharyl transferase PglB. Western blot analysis was performed on proteins extracted from E. coli SΦ874 (ΔwaaL) transformed with a plasmid for expression of PglB (pGVX970) and a plasmid for expression of AcrA (pGVX1; carrier protein) and a plasmid for production of CP14 (pGVX1366) or empty vector (pGVX8). After induction, cells were harvested and proteins were extracted from the periplasm and enriched by immobilized metal affinity chromatography (IMAC) and eluted by Tris buffer containing imidazole. 6A: purified samples were subjected to SDS-PAGE (4-12% gel) and electro blotted onto a nitrocellulose membrane developed by anti-His. Lane 1, unglycosylated AcrA; lane 2, glycosylated AcrA with a single CP14 engineered subunit. 6B: mass spectroscopy scan of intact unglycosylated AcrA and 6C: glycosylated AcrA. Mass of 39957.74 Da matches with unglycosylated AcrA and 39227.27 Da corresponds to glycosylated AcrA with one engineered CP14 subunit.
Figure 6B:
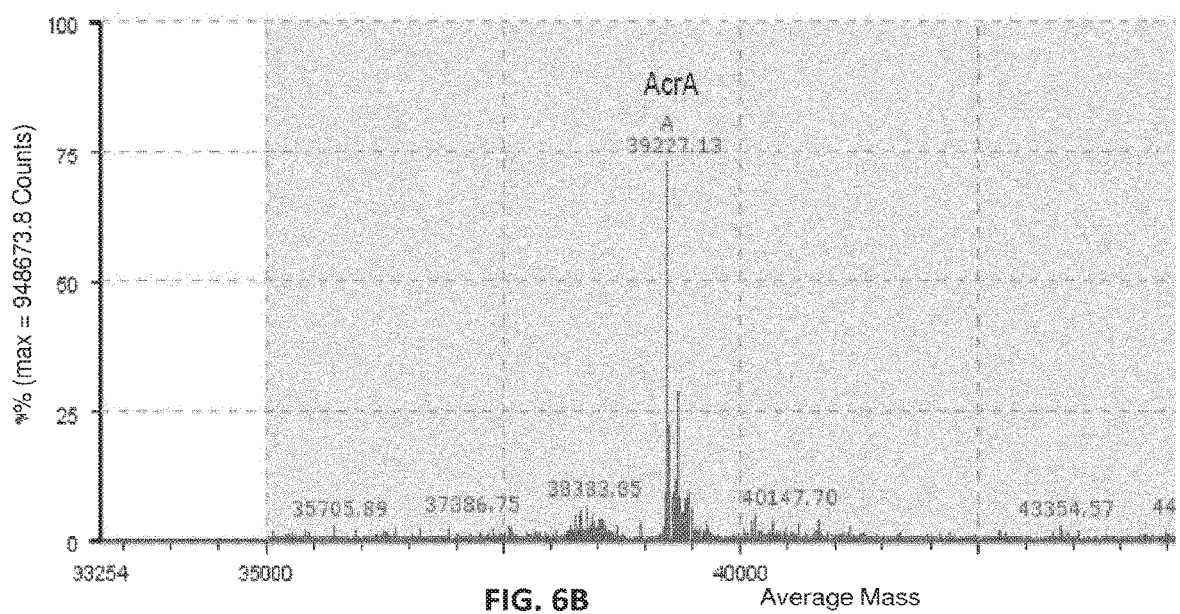
Figure 6C:
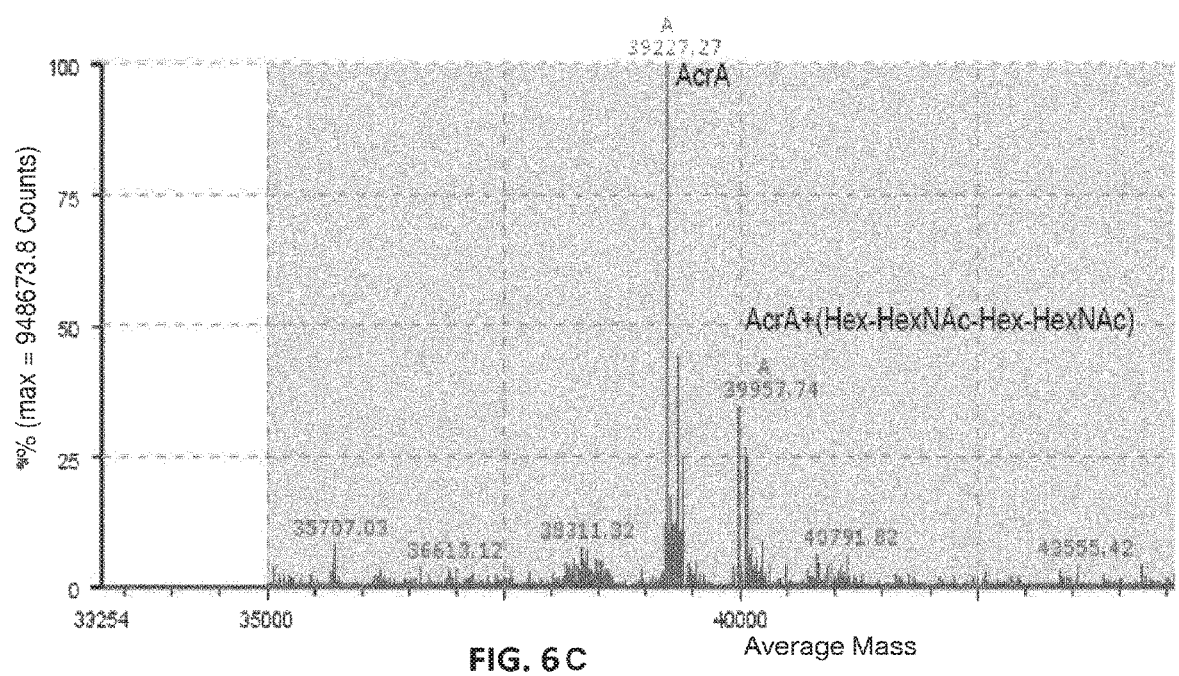

To confirm that the CP14 engineered subunit could be transferred by *C. jejuni* PglB, *E. coli* SΦ874 ΔwaaL cells were transformed with (i) pGVX970 (which comprises *C. jejuni* PglB), (ii) pGVX1 encoding AcrA (carrier protein), and (iii) pGVX1366 (see above) or its corresponding empty vector (pGVX81). After induction, proteins were extracted from the periplasm and enriched by IMAC and subjected to Western blot analysis (FIG. 6A). A band corresponding to glycosylated AcrA was observed only in cells transformed with plasmid pGVX1366 (FIG. 6A, lane 2) but not cells transformed with the empty vector (FIG. 6A, lane 1). The same purified proteins were analyzed by mass spectroscopy and it was confirmed that the CP14 engineered subunit was linked to AcrA (FIG. 6C). Thus, it was confirmed that the engineered (hybrid) CP14 is a substrate for PglB.

Figure 7:
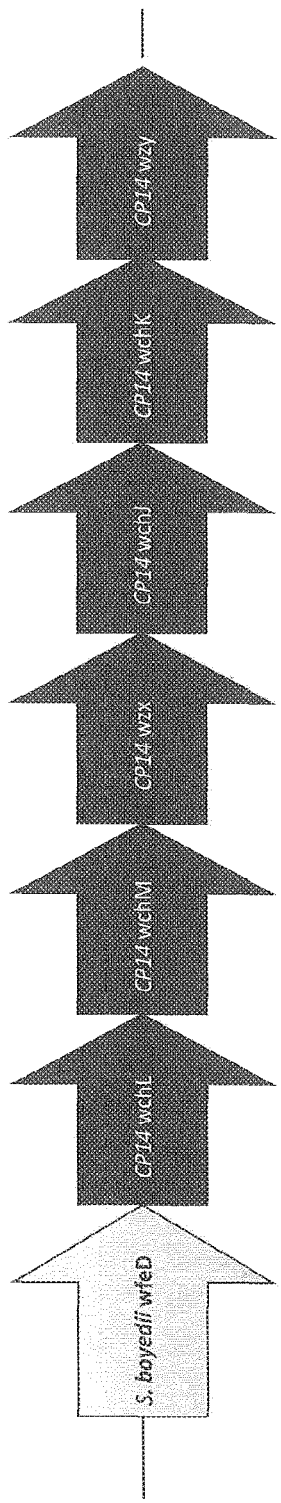
FIG. 7 depicts a schematic diagram of a synthetic gene cluster that has been synthesized for production of an engineered CP14 subunit (pGVX1433). Arrows indicate genes that have been assembled together for production of an engineered CP14 subunit in plasmid pGVX81. Grey arrow shows wfeD gene from Shigella boyedii which expresses galactoysltransferase that assembles Gal form UDP-Gal to GlcNAc-P-P-Undecaprenyl via β (1,4) linkage (J Bacteriol. 2011; 193(2):449-59). Black arrows indicate all of the necessary S. pneumoniae genes for production of a CP14 cluster except for the priming Glc transferase wchA (instead, endogenous E. coli wecA acts as the priming transferase that assembles GlcNAc on the undecaprenolpyrophosphate and therefore is not part of the plasmid).

To increase the productivity of wild type CP14 and enhance the polymerization of the engineered CP14 plasmid pGVX1366, it was further extended with CP14 wchJ-wchK (adding Gal to UndPP-Glc) and CP14 wzy. FIG. 7 shows gene organization of the synthetic plasmid, pGVX1433.

Figure 8A:
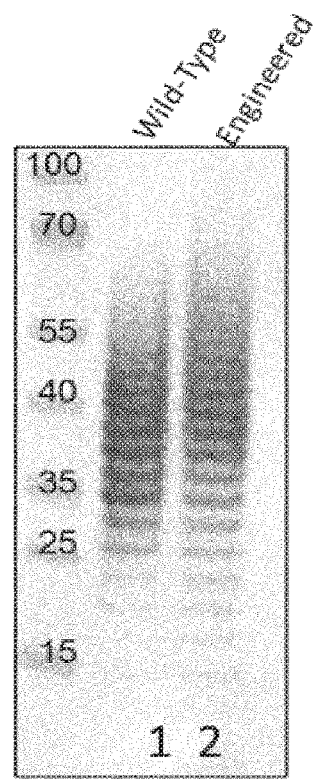
FIG. 8 depicts production of hybrid S. pneumoniae CP14 by combination of wildtype and heterologous pathways in an E. coli host cell. CP14 wild type cluster was integrated into colanic acid of E. coli W3110 ΔwaaL transformed with the CP14 engineering plasmid (pGVX1433) or empty vector (pGVX81). 8A: Western-blot analysis of proteinase K digested of whole cell E. coli W3110 Colanic acid::CP14 Δ waaL transformed with CP14 glycoengineering plasmid (lane 1) or empty plasmid (lane 2). Samples (LLO) were resolved in 4-12% SDS gel and blotted on a membrane. Serotyping anti-CP14 antibody was used as a primary antibody for developing CP14. 8B: LLO extracted and labeled by 2AB from E. coli W3110 (Colanic acid::CP14) transformed with CP14 glycoengineering plasmid (solid line) or empty plasmid (dotted line). The indicated peaks (by arrow)
Figure 8B:
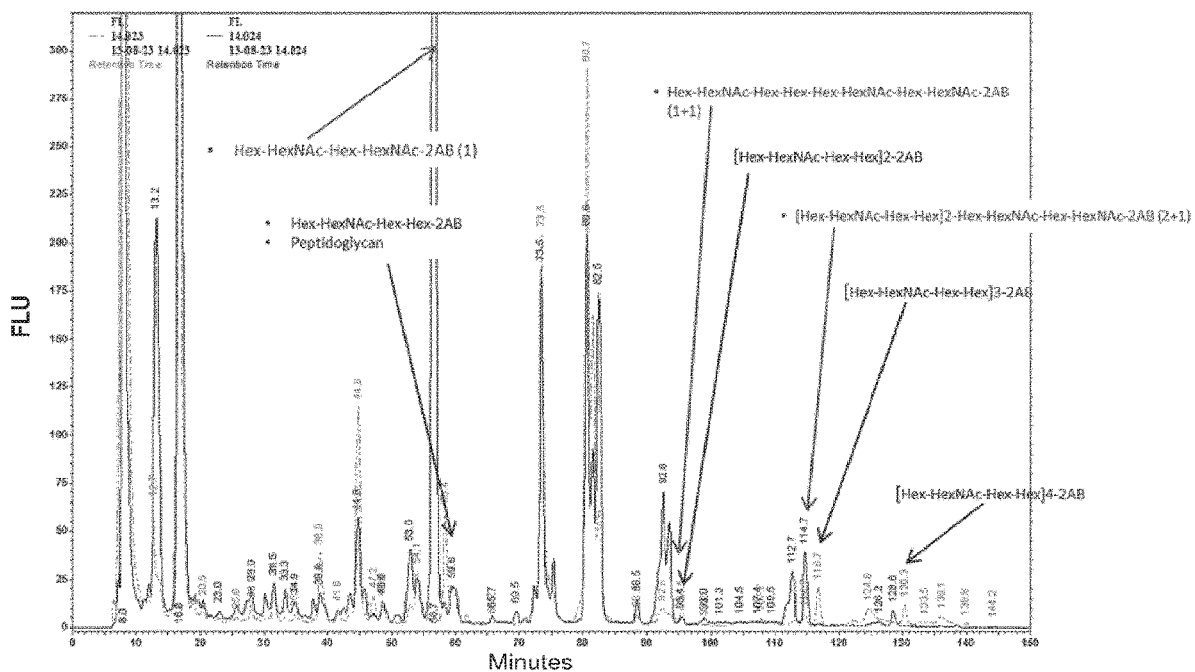

To demonstrate that hybrid CP14 polysaccharide could be produced in *E. coli* W3110 colanic acid::CP14 ΔwaaL cells (see International Patent Application No. WO2014/072405), host cells were transformed with an RcsA expressing plasmid (required for activation and production of wild type CP14) and engineered pGVX1433 or its corresponding empty vector (FIG. 8). After induction of the cells, whole cell extracts were digested with proteinase K and glycolipids were separated on SDS-PAGE and subjected to Western blot analysis using a serotyping CP14 antibody. Both *E. coli* strains transformed with CP14 engineered plasmid or its corresponding empty vector could produce LLO recognized by anti-CP14 antibody. This demonstrated that both cells could produce the correct CP14 polysaccharide structure (FIG. 8A). Cells were harvested after induction and LLO purified, labeled by 2AB and subjected to HPLC (FIG. 8B). It was shown that cells harboring the CP14 engineering plasmid produced polysaccharides that are identical to CP14 wild type except that it is attached to GlcNAc-2AB while in the presence of the empty vector the polysaccharide attached to Glc-2AB (as in CP14 wild type). This surprisingly demonstrated that the CP14 polymerase not only polymerizes the CP14 repeating unit but also assembles the wild type polymer on the engineered CP14 subunit which consequently terminates the polymerization reaction (as no engineered subunit could be detected in the middle of CP14 polysaccharide).

To demonstrate that only the engineered CP14 polymer could be efficiently transferred by PglB, *E. coli* W3110 (Colanic acid::CP14, ΔwaaL, ΔwecA-wzzE) and *E. coli* W3110 (CA:CP14 ΔwaaL) were transformed with RcsA plasmid (activator of CP14 synthesis), pGVX970 (expressing PglB), pGVX1 (expressing the protein carrier AcrA) and CP14 eng. Plasmid (pGVX1433) (FIG. 9). After induction, *E. coli* cells were harvested and whole cell proteinase K digested extracts (FIG. 9A) or protein extracted from the periplasm and enriched by IMAC were subjected to Western blot analysis using a typing CP14 antibody as a primary antibody (FIG. 9B). As shown in panel A, all strains produced LLO recognized by the anti-CP14 antibody (FIG. 9A lanes land 2); however, glycoprotein (CP14-AcrA) was only detected in strains expressing the CP14 engineering subunit in *E. coli* W3110 (Colanic Acid::CP14, ΔwaaL (FIG. 9A, lane 1) but not in *E. coli* W3110 (Colanic Acid::CP14, ΔwaaL, ΔwecA-wzzE) (FIG. 9A, lane 2). This strain lacks WecA (the priming transferase which adds GlcNAc to UndPP) and therefore cannot produce engineered CP14. This clearly demonstrates that CP14 that is assembled on an engineered CP14 subunit can be transferred by PglB to a protein carrier (AcrA), whereas the wild type CP14 polysaccharide cannot be efficiently transferred.

To demonstrate that the engineered CP14 polymer could be transferred by PglB to a different protein carrier, *E. coli* W3110 Colanic Acid::CP14, ΔwaaL cells were transformed with CP14 eng. plasmid (pGVX1433) and a plasmid for expression of RcsA, pGVX970, and pGVX538 (expressing the carrier protein EPA). All samples were harvested after induction and the protein was extracted from the periplasm and enriched by IMAC. Enriched protein samples were separated by SDS-PAGE (4-12% gel) and electro blotted onto a nitrocellulose membrane then incubated with an anti-His antibody (FIG. 10 panel A) or a typing CP14 antibody (FIG. 10 panel B). The reactive ladder-like bands were observed when anti-His or anti-CP14 antibody was used, indicating that the engineered CP14 could be conjugated to EPA. Furthermore the same cells were grown in a bioreactor and subjected to purification (FIG. 11). Using traditional ion exchange chromatography and lectin (*Ricinus communis* agglutinin) affinity chromatography, purified conjugate was obtained (FIG. 11C).

Example 2: Synthesis of CP33F Bioconjugates in *E. coli*

Example 1 demonstrates that oligosaccharides or polysaccharides that comprise a hexose monosaccharide at the reducing end of the first repeat unit can be modified by replacing the hexose monosaccharide with a hexose monosaccharide derivative, thus allowing such hybrid oligosaccharides or polysaccharides to be linked to carrier proteins (to form bioconjugates) in host cells. As described in Example 1, relaxed specificity of glycosylation machinery (flippases, polymerases) in heterlogous host cells is fundamental to production of the hybrid oligosaccharides or polysaccharides in the host cells. This example describes the engineering of another hybrid polysaccharide, S. pneumoniae CP33F, in a host cell and confirms that the hybrid polysaccharide is a substrate for PglB in the host cell.

The CP33F gene cluster is depicted in FIG. 12 and the repeating unit structure of S. pneumoniae CP33F is shown in FIG. 1. The repeat unit of CP33F is composed of β-D-Galf-1,3-β-D-Gal-1,3-α-D-Gal(α1,2-D-Gal)-1,3-β-D-Galf-1,3-D-Glc-.

The portion of the CP33F gene cluster containing the stretch from wchA to glF (see FIG. 12) was cloned into the pDOC-C plasmid (PLoS Genet. 2006 March; 2(3):e31.) and integrated into the E. coli W3110 colanic acid cluster as described in International Patent Application Publication No. WO2014/072405. E. coli W3110 colanic acid::CP33F that produces CP33F, under control of RcsA, was generated and used for the following experiments (FIG. 13A). In addition, to improve production of bioconjugates for next steps, ligase (waaL) of E. coli W3110 colanic acid::CP33F was replaced by C. jejuni pglB to generate strain E. coli W3110 colanic acid::CP33FwaaL:pglB. As it is shown in FIG. 13B, E. coli W3110 colanic acid::CP33F waaL:pglB produced comparable amounts of LLO to E. coli W3110 colanic acid::CP33F.

To synthesize a glycoengineered CP33F subunit (a repeat unit comprising a hexose monosaccharide derivative at the reducing end), two galactofuranosyltransferases, WbeY from E. coli O28 and WfdK from E. coli O167 were used. It was predicted from the structure of E. coli O28 and E. coli O167 LPS that both structures are composed of Galf attached via β (1,3) linkage to reducing GlcNAc (Carbohydr Res. (1996) 127-39, Eur. J. Biochem. 246 (1997) 565-573). Therefore it was predicted that WbeY and WfdK can transfer Galf to -GlcNAc-P-P-Undecprenyl. GlcNAc was assembled on UndP from UDP-GlcNAc by WecA (which exists in all Gram-negative bacteria that synthesize ECA and Gram-positive bacteria that makes Teichoic acid) (Annu Rev Microbiol. 2013; 67:313-36; Glycobiology. 2011 February; 21(2):138-51.), to make a β (1,3) linkage (J Bacteriol. 2011 January; 193(2):449-59). Thereafter, using the glycosyltransferases WciC, WciD, WciE and WciF from the S. pneumoniae CP33F gene cluster, synthesis of the CP33F engineered subunit (β-D-Galf-1,3-β-D-Gal-1,3-α-D-Gal (α1,2-D-Gal)-1,3-β-D-Galf-1,3-D-GlcNAc-PP-Undd) was completed (FIG. 14B). The schematic gene organization of the synthetic plasmid for production of the engineered CP33F subunit is illustrated in FIG. 14A (pGVX2342). This plasmid produces the CP33F engineered subunit in the cytoplasm, from which it is translocated into the periplasm by the flippase of CP33F where the wild type polysaccharide can be assembled on it by action of CP33F polymerase (wzy). Plasmid pGVX2342 also contains CP33F polymerase (wzy) and E. coli O16 galE and glf to enhance productivity of wild type polymerase well as engineered subunit (FIG. 14A).

To demonstrate that the polymerase (wzx) of CP33F has relaxed glycan specificity and can translocate the engineered CP33F repeating unit from the cytoplasm into the periplasm. E. coli W3110 was transformed with plasmid pGVX2342 (FIG. 14) or a corresponding plasmid containing all of the necessary genes for production of CP33F except the CP33F flippase (wzx) (pGVX2098). After induction, cells were harvested and subjected to proteinase K digestion. Digested cells were run on SDS-PAGE 4-12% and subjected to silver staining or electro-blotted on nitrocellulose and subjected to Western blot analysis using a typing CP33F antibody. As seen in FIG. 15A, an extra band on the lipid A core was only detected in E. coli cells transformed with plasmid pGVX2342 (FIG. 15A, lane 2) and not pGVX2098, which lacks the CP33F flippase (FIG. 15A, lane 1). This band was also detected by Western blot using anti-CP33F antibody (FIG. 15B, lane 2) demonstrating that the CP33F engineered repeating unit was produced and translocated into the periplasm of E. coli where the O antigen ligase (WaaL) transferred it to the lipid A core. Interestingly this experiment demonstrates that the CP33F engineered subunit can be recognized by an antibody that has been raised against the wild type CP33F and that they share similar immunogenic epitopes.

To verify the structure of the CP33F engineered subunit, pGVX2342 or its corresponding empty vector was transformed into E. coli SΦ874 ΔwaaL cells. After induction, cells were harvested and LLO was purified and labeled by 2AB and subjected to HPLC (FIG. 16). HPLC chromatogram (FIG. 16, panel A) shows a unique peak eluting at 72 minutes. This peak was collected and subjected to mass spectroscopy analysis and it was demonstrated that monosaccharide composition of the oligosaccharide matched the proposed CP33F engineered subunit (FIG. 16, panel B).

To demonstrate that the CP33F engineered subunit could be transferred by C. jejuni PglB, E. coli SΦ874 ΔwaaL cells were transformed with pGVX970 (encoding C. jejuni PglB), pGVX1 (encoding AcrA protein carrier) and pGVX2305 (encoding the engineering CP33F subunit) or its corresponding empty vector (pGVX1387). After induction, proteins were extracted from the periplasm and enriched by IMAC and subjected to Western blot analysis (FIG. 17). A band corresponding to glycosylated AcrA was only observed when plasmid pGVX1366 (FIG. 17A, lane 2) was present and not the empty vector (FIG. 17A, lane 1). Also, Western-blot analysis of the same purified proteins using a typing anti-CP33F antibody visualized a band from protein samples extracted from E. coli cells harboring the CP33F engineering plasmid (FIG. 17B, lane 2) and not the corresponding empty vector FIG. 17B, lane 1). This demonstrated that only the CP33F engineered subunit could be efficiently transferred by PglB to a protein carrier.

To demonstrate that the engineered CP33F polymer could be transferred by PglB and that the wild type CP33F polysaccharide is not a PglB substrate, E. coli W3110 (colanic acid::CP33FwaaL::pglB ΔwecA-wzzE) cells were transformed with RcsA plasmid (activator of CP33F synthesis), pGVX970 (expressing PglB), pGVX2310 expressing EPA (protein carrier), and the CP33F engineering plasmid (pGVX2342) or its corresponding empty vector (FIG. 18). After induction, E. coli cells were harvested and Western-blot analysis was performed for whole cell proteinase K digested extracts (FIG. 18A) or protein was extracted from the periplasm and enriched by IMAC (FIGS. 18B and C). Western blot analysis using a typing CP33F antibody as a primary antibody for analysis of proteinase K digested extracts showed that all strains produced LLO (ladder-like pattern) (FIG. 18A). However, glycoprotein (CP33F-EPA) was only detected in the strain harboring the CP33F engineering plasmid (FIGS. 18B and C; lanes 3 and 4) and not the empty vector (FIGS. 18B and C; lanes 1 and 2). This clearly demonstrates that CP33F is transferred by PglB to a protein carrier when it is assembled on engineered CP33F subunit (that is, when engineered as a hybrid polysaccharide that comprises a hexose monosaccharide derivative in place of a hexose monosaccharide at the reducing end of the first repeat unit).

Example 3: Synthesis of CP14 Conjugates in *E. coli* using a Different Modification Approach Examples 1 and 2 describe how to modify host cell backgrounds so as to render the host cells capable of producing hybrid oligosaccharides or polysaccharides that comprise a hexose monosaccharide derivative in place of a hexose monosaccharide at the reducing end of the first repeat unit. Examples 1 and 2 also demonstrate that, surprisingly, relaxed specificity of certain glycosylation machinery (flippases, polymerases) allows for production of such hybrid oligosaccharides or polysaccharides in heterologous host cells. This Example demonstrates an alternative approach for making hybrid oligosaccharides or polysaccharides that also are substrates for PglB in host cells. In particular, this Example demonstrates that by adding a hexose monosaccharide derivative to a donor oligosaccharide or polysaccharide that comprises a hexose monosaccharide at the reducing end of the first repeat unit, a hybrid oligosaccharide or polysaccharide can be produced that is a substrate for PglB. Further, this Example demonstrates that, surprisingly, the hybrid oligosaccharides or polysaccharides produced according to this Example are extremely efficient substrates for PglB. Finally, this Example demonstrates that bioconjugates comprising the hybrid oligosaccharides or polysaccharides produced according to this Example are functional and immunogenic in vivo.

Genes of the wild type gene cluster of from *S. pneumoniae* CP14 (see FIG. 19A) were cloned and integrated into *E. coli* the chromosome in place of the *E. coli* W3110 colanic acid cluster as described in International Patent Application No. WO 2014/072405. The resultant genetically modified *E. coli* produces wild type CP14 (the structure of one repeating unit (RU) of wild type CP14 is presented in FIG. 19B).

Next, a synthetic gene cluster (see FIG. 20) was produced that was capable of producing a modified oligosaccharide that is similar to the wild type (i.e. CP14) repeating unit except that it contains an additional monosaccharide at the reducing end, wherein the additional monosaccharide was a hexose monosaccharide derivative. Generally, the production of this oligosaccharide was achieved by combining several glycosyltransferases that have known functions. The specific steps were: first, GlcNAc was assembled on UndP in the *E. coli* host cell from UDP-GlcNAc by WecA (see above). Then, the Z3206 epimerase from *E. coli* O157 converted GlcNAcUndPP to GalNAcUndPP. Next, wciQ from *E. coli* O21 added glucose (Glc) via a b(1,3) linkage to GlcNAcUndPP to form Glc b(1,3) GlcNAc. Next, *E. coli* O21 wciP addsd Gal via b(1,4) linkages to the disaccharide to form a trisaccharide, Gal b(1,4) Glc b(1,3) GalNAcUndPP. Finally, wchL (GlcNAc transferase) and wchM (Galctosyltransferase) from *S. pneumoniae* CP14 completed assembly of the repeat unit (see FIG. 20). The resulting hybrid repeat unit comprised the following: (i) a hexose monosaccharide derivative at the reducing end and (ii) the first repeat unit of from *S. pneumoniae* CP14.

The engineered (hybrid) subunit was able to be translocated from the cytoplasm of the host cell to the periplasm of the host cell by the flippase from *C. jejuni* (PglK) (this flippase was introduced into the *E. coli* host cell using standard recombination techniques). Once translocated by the flippase, wild type CP14 polysaccharide was polymerized on top of the engineered (hybrid) subunit by the *S. pneumonia* polymerase present in the *E. coli* host cell, again demonstrating, surpringly, relaxed specificity of polymerase that was essential to generation of the hybrid CP14 polysaccharide. See FIG. 21.

Next, it was determined that that PglB was able to transfer the engineered CP14 polymer to the carrier protein EPA (see FIG. 22), resulting in the production of hybrid CP-14-EPA bioconjugates that could be purified (see FIG. 23). Surprisingly, it was determined that the modified host cells described in this Example were able to produce very high yields of hybrid CP-14-EPA bioconjugates. In fact, the yields of hybrid CP-14-EPA bioconjugates produced using the method of this Example were 70-fold greater than the yields of CP-14-EPA bioconjugates produced in Example 1.

Next, the functionality and immunogenicity of the hybrid CP-14-EPA bioconjugates was assessed. New Zealand white female rabbits were immunized with purified hybrid CP-14-EPA bioconjugate or, as a control, Prevnar 13. See FIG. 24. As shown in FIG. 25, the hybrid CP-14-EPA bioconjugates produced according to this Example remained functional and were highly immunogenic.

Example 4: Synthesis of CP15A Bioconjugates in *E. coli*

Example 1 demonstrates that oligosaccharides or polysaccharides that comprise a hexose monosaccharide at the reducing end of the first repeat unit can be modified by replacing the hexose monosaccharide with a hexose monosaccharide derivative, thus allowing such hybrid oligosaccharides or polysaccharides to be linked to carrier proteins (to form bioconjugates) in host cells. As described in Example 1, relaxed specificity of glycosylation machinery (polymerases) in heterlogous host cells is fundamental to production of the hybrid oligosaccharides or polysaccharides in the host cells. This example describes the engineering of another hybrid polysaccharide, *S. pneumoniae* CP15A, in a host cell and confirms that the hybrid polysaccharide is a substrate for PglB in the host cell.

The CP15A gene cluster is depicted in FIG. 27 and the repeating unit structure of *S. pneumoniae* CP15A is shown in FIG. 28. The repeat unit of CP15A is composed of α-D-Gal-1,2-β-D-Gal-1,4-[Gro-2-P-3]-β-D-GlcNAc-1,3-β-D-Gal-1,4-D-Glc- The ligase (waaL) of *E. coli* W3110 was replaced by *C. jejuni* pglB to generate strain *E. coli* W3110 waaL::pglB (StGVXN8011). As a next step, the portion of the CP15A gene cluster containing the stretch from wchA to gtp3 (see FIG. 27) was cloned into the pDOC plasmid (PLoS Genet. 2006 March; 2(3):e31.) and integrated into the *E. coli* W3110 waaL::pglB (StGVXN8011) colanic acid cluster as described in International Patent Application Publication No. WO2014/072405 to produce StGVXN9510. *E. coli* W3110 colanic acid::CP15A waaL::pglB that produces CP15A, under control of RcsA, was generated and used for the following experiments (FIG. 30).

To synthesize a glycoengineered CP15A subunit (a repeat unit comprising a hexose monosaccharide derivative at the reducing end), a glucosyltransferase WclQ and a galactosyltransferases WclP from *E. coli* O21, a N-acetylglucosamine transferase WchL and a galactosyltransferase WchM from *S. pneumoniae* CP14, an epimerase Z3206 from *E. coli* O157, a galactosyltransferase WchN from *S. pneumoniae* CP15A and a flippase PglK from *C. jejuni* were used (FIG. 29A). GlcNAc was assembled on UndP from UDP-GlcNAc by WecA (which exists in all Gram-negative bacteria that synthesize ECA and Gram-positive bacteria that makes Teichoic acid) (Annu Rev Microbiol. 2013; 67:313-36; Glycobiology. 2011 February; 21(2):138-51.), to make a β (1,3) linkage (J Bacteriol. 2011 January; 193(2):449-59) and was converted to Und-PP-GalNAc by epimerase Z3206. Thereafter, using the glycosyltransferases WclQ and WclP (Journal of Microbiological Methods. 2008; 75(2):329-334) a glucose and a galactose is added as a $2^{nd}$ and $3^{rd}$ sugar moiety, respectively. In the following, WchL, and WchM from S. pneumoniae CP14 add a N-glucosamine moiety and a galactose moiety, respectively and WchN from S. pneumoniae CP15A adds a galactose as a terminal moiety to complete the engineered subunit α-D-Gal-1,2-β-D-Gal-1,4-β-D-GlcNAc-1,3-β-D-Gal-1,4-β-D-Glc-1,3-D-GalNAc- was completed (FIG. 29B). The schematic gene organization of the synthetic plasmid for production of the engineered CP15A subunit is illustrated in FIG. 29A (pGVX3058). This plasmid produces the CP15A engineered subunit in the cytoplasm, from which it is translocated into the periplasm by the flippase PglK from C. jejuni where the wild type polysaccharide can be assembled on it by action of CP15A polymerase (wzy).

To demonstrate that the engineered CP15A subunit could be a substrate for CP15A polymerase (wzy) and to be incorporated into wild type CP15A polymer and transferred by PglB onto a carrier protein, E. coli W3110 (colanic acid::CP15A waaL::pglB) cells were transformed with RcsA plasmid (activator of CP15A synthesis), pGVX2703 expressing carrier protein AcrA, pGVX3058 expressing CP15A engineering plasmid or its corresponding empty vector (FIG. 30). After induction, E. coli cells were harvested and Western-blot analysis was performed for whole cell proteinase K digested extracts (FIG. 30A) or protein was extracted from the periplasm and enriched by IMAC (FIGS. 30B and 30C). Western blot analysis using a typing CP15A antibody as a primary antibody for analysis of proteinase K digested extracts showed that all strains produced LLO (ladder-like pattern) (FIG. 30A line 1 and 2). However, glycoprotein (CP15A-AcrA) was only detected in the strain harboring the CP15A engineering plasmid (FIGS. 30B and 30C; lanes 2) and not the empty vector (FIGS. 30B and 30C; lanes 1). This clearly demonstrates that CP15A is transferred by PglB to a protein carrier when it is assembled on engineered CP15A subunit (that is, when engineered as a hybrid polysaccharide that comprises a hexose monosaccharide derivative in place of a hexose monosaccharide at the reducing end of the first repeat unit).

Equivalents

The methods, host cells, and compositions disclosed herein are not to be limited in scope by the specific embodiments described herein. Indeed, various modifications of the methods, host cells, and compositions in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed is:

1. A E. coli strain W3110 comprising a deletion of the waaL, wherein said E. coli strain comprises an expression vector comprising nucleic acids for expression in the host cell:
   a) nucleic acids that encode (i) glycosyltransferases that produce an oligosaccharide or polysaccharide repeat unit, wherein said repeat unit does not comprise a hexose at the reducing end, and wherein said oligosaccharide or polysaccharide repeat unit is derived from a donor oligosaccharide or polysaccharide repeat unit that comprises a hexose at the reducing end, and (ii) heterologous glycosyltransferases sufficient for synthesis of the donor oligosaccharide or polysaccharide repeat unit wherein the donor oligosaccharide or polysaccharide is that of S. pneumoniae; and
   b) a nucleic acid that encodes a carrier protein comprising an N-glycosylation consensus sequence; and
   c) a nucleic acid that encodes an oligosaccharyl transferase;
   d) a nucleic acid that encodes a wzy polymerase, wherein the polymerase catalyzes the production of a hybrid oligosaccharide or polysaccharide, wherein the hybrid oligosaccharide or polysaccharide (i) comprises a hexose monosaccharide derivative at the reducing end of the first repeat unit and (ii) comprises hexose monosaccharides at the reducing end of all other repeat units;
   e) nucleic acid that encodes a heterologous flippase of the donor polysaccharide or oligosaccharide gene cluster;
   f) nucleic acid that encodes RcsA; and
   g) nucleic acid that encodes an epimerase (in the instant the hybrid oligosaccharide or polysaccharide comprises a hexose monosaccharide derivative at the reducing end of the first repeat unit in addition to the hexose monosaccharide normally present at the reducing end of the first repeat unit of the donor oligosaccharide or polysaccharide).

2. The host cell of claim 1, wherein said host cell comprises (a) (i) a glycosyltransferase that assembles a hexose monosaccharide derivative onto undecaprenyl pyrophosphate (UND-PP) and (ii) one or more glycosyltransferases capable of adding a monosaccharide to the hexose monosaccharide derivative assembled on UND-PP; or (b) (i) a glycosyltransferase that assembles a hexose monosaccharide derivative onto undecaprenyl pyrophosphate (UND-PP) and (ii) glycosyltransferases that assemble the donor oligosaccharide or polysaccharide repeat unit onto the hexose monosaccharide derivative.

3. The host cell of claim 2, wherein said hexose monosaccharide derivative is any monosaccharide in which C-2 position is modified with an acetamido group.

4. The host cell of claim 3, wherein said hexose monosaccharide derivative is N-acetylglucosamine (GlcNAc), N-acetylgalactosamine (GalNAc), 2,4-Diacetamido-2,4,6-trideoxyhexose (DATDH), N-acetylfucosamine (FucNAc), N-acetylquinovosamine (QuiNAc).

5. The host cell of claim 2, wherein said glycosyltransferase that assembles a hexose monosaccharide derivative onto UND-PP is wecA.

6. The host cell of claim 2, wherein said one or more glycosyltransferases capable of adding a monosaccharide to the hexose monosaccharide derivative is the wfeD galactosyltransferase from Shigella boyedii; or the wbeY galactofuranosyltransferase from E. coli O28; or the wfdK galactofuranosyltransferase from E. coli O167; or are the wbeY galactofuranosyltransferase from E. coli O28 and the wfdK galactofuranosyltransferase from E. coli O167.

7. The host cell of claim 1, wherein said glycosyltransferases sufficient for synthesis of the repeat units of the donor oligosaccharide or polysaccharide comprise (i) wchL and/or wchM from *S. pneumoniae* CP14, and/or (ii) wciC, wciD, wciE, and/or wciF from *S. pneumoniae* CP33F.

8. The host cell of claim 2, wherein the glycosyltransferases that assemble the donor oligosaccharide or polysaccharide repeat unit onto the hexose monosaccharide derivative comprise a glycosyltransferase that is capable of adding the hexose monosaccharide present at the reducing end of the first repeat unit of the donor oligosaccharide or polysaccharide to the hexose monosaccharide derivative.

9. The host cell of claim 8, wherein said glycosyltransferase is a wciP galactosyltransferase.

10. The host cell of claim 2, wherein the glycosyltransferases that assemble the donor oligosaccharide or polysaccharide repeat unit onto the hexose monosaccharide derivative comprise a glycosyltransferase that is capable of adding the monosaccharide that is adjacent to the hexose monosaccharide present at the reducing end of the first repeat unit of the donor oligosaccharide or polysaccharide to the hexose monosaccharide present at the reducing end of the first repeat unit of the donor oligosaccharide or polysaccharide.

11. The host cell of claim 10, wherein said glycosyltransferase is a wciQ glucosytransferase.

12. The host cell of claim 2, wherein said host cell further comprises an enzyme capable of modifying a monosaccharide.

13. The host cell of claim 1, wherein said host cell comprises (a) a nucleic acid that encodes a wzy capsular polysaccharide polymerase or an wzy 0 antigen polymerase and/or (b) a nucleic acid that encodes a wzx flippase.

14. The host cell of claim 13, wherein said polymerase of (a) and/or (b) is encoded from a gene cluster *Streptococcus pneumoniae* Capsular Polysaccharide (CP) CP1, CP2, CP3, CP4, CPS, CP6 (A and B), CP7 (A,B, C), CP8, CP9 (A, L,N, V), CP10 (A,B,C,F), CP11 (A, B,C,D,F), CP12(A,B,F), CP13, CP14, CP15(A,B,C,F), CP16(A,F), CP17(A,F), CP18 (A,B,C,F), CP19(A,B,C,F), CP20, CP21, CP22(A,F), CP23 (A,B,F), CP24(A,B,F), CP25(A,F), CP26, CP27, CP28(A, F), CP29, CP31, CP32(A,F), CP33(A,B,C,D,F), CP34, CP35(A,B,C,D,F), CP36, CP37, CP38, CP39, CP40, CP41 (A,F), CP42, CP43, CP44, CP45, CP46, CP47(A,F), or CP48.

15. The host cell of claim 1, wherein said donor polysaccharide is the *Streptococcus pneumoniae* capsular polysaccharide (CP) CP2, CP3, CP6 (A, B), CP7 (A, B), CP8, CP9 (A, L, N, V), r[CP1MCP10 (A, F), CP11 JA, B, C, F), CP13, CP14, CP15 (A, B, C, F), CP17 (A, F), CP18 (A, B, C, F), CP19 (A, B, C, F), CP20, CP22 (F), CP23 (F), CP27, CP29, CP31, CP32 (A, F), CP33 (B, F), CP34, CP35 (A, B), or CP37.

16. The host cell claim 1, wherein said oligosaccharyl transferase is the pglB gene of *Campylobacter jejuni*.

17. A method of producing a bioconjugate comprising a carrier protein N-linked to an oligosaccharide or polysaccharide that does not comprise a hexose at the reducing end of the first repeat unit, said method comprising (i) culturing the host cell of claim 1 under conditions suitable for the production of proteins and (ii) isolating said bioconjugate.

* * * * *